(12) United States Patent  
Huang

(10) Patent No.: US 8,809,357 B2
(45) Date of Patent: Aug. 19, 2014

(54) COMPOUNDS AND DERIVATIZATIONS OF DNAS AND RNAS ON THE NUCLEOBASES OF PYRIMIDINES FOR FUNCTION, STRUCTURE AND THERAPEUTICS

(76) Inventor: Zhen Huang, Marietta, GA (US)

( * ) Notice: Subject to any disclaimer, the term of this patent is extended or adjusted under 35 U.S.C. 154(b) by 0 days.

(21) Appl. No.: 13/321,544

(22) PCT Filed: May 20, 2010

(86) PCT No.: PCT/US2010/035631
§ 371 (c)(1),
(2), (4) Date: Nov. 19, 2011

(87) PCT Pub. No.: WO2010/135564
PCT Pub. Date: Nov. 25, 2010

(65) Prior Publication Data
US 2012/0070825 A1    Mar. 22, 2012

Related U.S. Application Data

(60) Provisional application No. 61/180,028, filed on May 20, 2009.

(51) Int. Cl.
*A01N 43/54*    (2006.01)
*A61K 31/505*   (2006.01)

(52) U.S. Cl.
USPC .......................... 514/274; 544/243; 544/318

(58) Field of Classification Search
USPC .................................. 544/244, 318; 514/274
See application file for complete search history.

(56) References Cited

PUBLICATIONS

V. Thiviyanathan et al., 366 Biochemical and Biophysical Research Communications, 752-757 (2008).*
International Preliminary Report on Patentability, PCT/US2010/035631 (Nov. 22, 2011).*
Schinazi et al., 29 Journal of Medicinal Chemistry, 1293-1295 (1986).*
A. Hassan, 11 Organic Letters, 2503-3506 (2009).*
Oxford Dictionary of Chemistry 169 (John Daintith ed., 6th ed., 2008).*
S. Mirozoeva et al. J. Med. Chem. 45, 563-566 (2002).*
E.A. Kümmerle et al., 949 Journal of Molecular Structure: Theochem, 23-27 (2010).*

* cited by examiner

*Primary Examiner* — Deepak Rao
*Assistant Examiner* — Alexander R Pagano
(74) *Attorney, Agent, or Firm* — Arnall Golden Gregory LLP

(57) ABSTRACT

The present invention relates to compounds of formula (I), a derivative, or a tautomer thereof, or a pharmaceutically acceptable salt of said compound or said tautomer; methods of preparation of the same; and methods of counducting drug discovery and research by applying the same in an investigation.

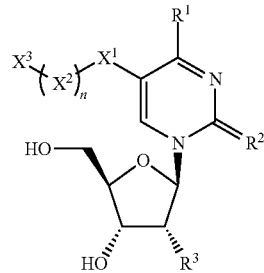

5 Claims, 61 Drawing Sheets (a) TBDMS-Cl, Im, DMF, 4 h, room temperature (RT); (b) i) NaH, THF, 15 min, RT; ii) n-BuLi, THF, 10 min., -78 °C; iii) Ph$_2$Te$_2$, 1 h, -78 °C; (c) TBAF, THF, 4 h, RT; (d) i-Pr$_2$NP(Cl)CH$_2$CH$_2$CN, DIEA, CH$_2$Cl$_2$, 1 h, RT; (e) the solid-phase synthesis.

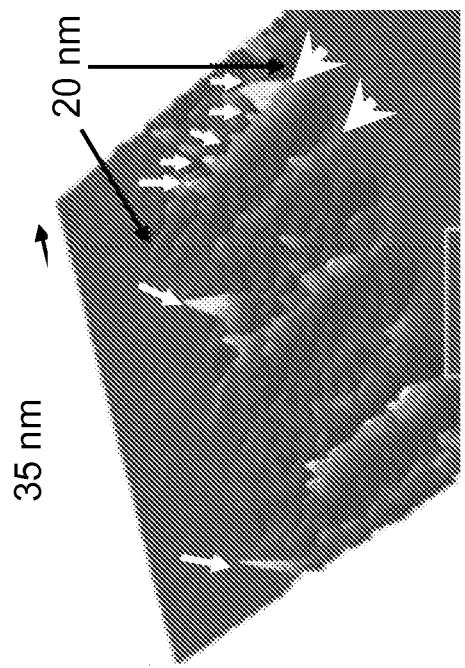
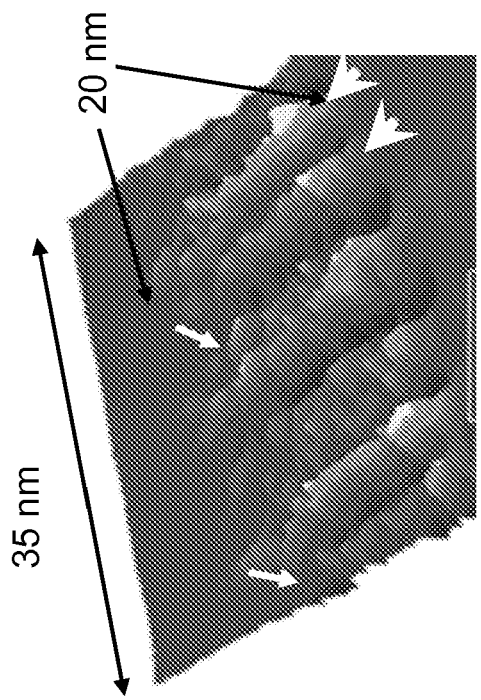
FIG. 55A
FIG. 55B

US 8,809,357 B2

COMPOUNDS AND DERIVATIZATIONS OF DNAS AND RNAS ON THE NUCLEOBASES OF PYRIMIDINES FOR FUNCTION, STRUCTURE AND THERAPEUTICS

CROSS-REFERENCE TO RELATED APPLICATIONS

This application is a U.S. National Stage Application under 35 U.S.C. §371 of International Application No. PCT/US2010/035631 filed May 20, 2010, which claims benefit of U.S. Provisional Application No. 61/1080,028, filed May 20, 2009, the contents of which are entirely incorporated herein by reference.

STATEMENT REGARDING FEDERALLY SPONSORED RESEARCH

This invention was made with government support under Grant Nos CBE-0750235 and MCB-0517092 awarded by the National Science Foundation. The U.S. government has certain rights in the invention. This invention was made with support of the Georgia Cancer Coalition and the Board of Regents of the University System of Georgia under that certain agreement in Atlanta, Ga. dated Oct. 1, 2002 and entitled "Agreement Re: Distinguished Cancer Clinicians and Scientists Program. The Board of Regents and the State of Georgia have certain rights in the invention.

REFERENCE TO SEQUENCE LISTING

The Sequence Listing submitted Nov. 19, 2011 as a text file named "SEQUENCE_LISTING.txt," created on Nov. 15, 2011, and having a size of 1.13 kilobytes is hereby incorporated by reference pursuant to 37 C.F.R. §1.52(e)(5).

BACKGROUND

Nucleic acids play important role in many biological functions, particularly in genetic information storage, gene expression and protein synthesis [Watson, J. D. & Crick, F. H. (1953) *Nature* 171, 737-8; Storz, G. (2002) *Science* 296, 1260-1263]. DNA is hydrolytically more stable than RNA due to the absence of the 2'-OH. The other major chemical difference between DNA and RNA is the presence of the 5-methyl group in DNA thymine comparing to RNA uracil. Since both thymine (5-methyl uracil) and uracil can form the same type of base pair with adenine (T-A and U-A pairs), it is essential to understand the fundamental functions of the C5 methyl group on thymine. Interestingly, the C5-methylated uracil (thymine) is also observed in many natural RNAs, such as ribosomal RNAs and tRNAs [Becker, H. F., Motorin, Y., Florentz, C., Giege, R. & Grosjean, H. (1998) *Nucleic Acids Res* 26, 3991-7; Sprinzl, M. & Vassilenko, K. S. (2005) *Nucleic Acids Res* 33, D139-40; McCloskey, J. A. & Rozenski, J. (2005) *Nucleic Acids Res* 33, D135-8]. In addition, comparing with uracil in RNA, thymine in DNA contributes to better stacking interaction [Wang, S. & Kool, E. T. (1995) *Biochemistry* 34, 4125-32] in part by providing $CH_3 \cdots \pi$ interaction with a 5'-preceding purine or pyrimidine moiety [Umezawa, Y. & Nishio, M. (2002) *Nucleic Acids Res* 30, 2183-92; Chatterjee, S., Pathmasiri, W. & Chattopadhyaya, J. (2005) *Org Biomol Chem* 3, 3911-5]. Furthermore, methylated cytosine at the C5 and N4 as well as methylated adenine at the NO in DNA form epigenetic marks and allow modulation of DNA-protein interactions [Suzuki, M. M. & Bird, A. (2008) *Nat Rev Genet* 9, 465-76; Ng, L. J., Cropley, J. E., Pickett, H. A., Reddel, R. R. & Suter, C. M. (2009) *Nucleic Acids Res*; Petrovich, M. & Veprintsev, D. B. (2009) *J Mol Biol* 386, 72-80; Manlius, M. G. & Casadesus, J. (2009) *FEMS Microbiol Rev*], which gives methylated DNA biological advantages in regulation, replication, transcription, and nuclease resistance [Low, D. A. & Casadesus, J. (2008) *Curr Opin Microbiol* 11, 106-12]. From the RNA molecular evolution point of view [Gesteland, R. F. C., T. R.; Atkins, J. F., Eds. (2006) *The RNA World: The Nature of Modern RNA Suggests a Prebiotic RNA*, ed. 3, (Cold Spring Harbor Laboratory Press Cold Spring Harbor, N.Y.)], therefore, the 5-methyl group of thymine in DNA, compared with 5-hydrogen of uracil in RNA, may be considered as the constant DNA methylation.

Interestingly, structure studies of DNA duplexes and DNA-protein complexes indicate a largely varied distance (from 7.4 to 3.4 Å) between the 5-methyl group of a thymine in DNA and the closest non-bridging oxygen (pro-Sp oxygen) of its 5'-phosphate moiety (15-24), suggesting a possible dynamic interaction between this constant methyl group and the phosphate backbone under certain circumstances. This interaction (the hydrogen bonding between the methyl and phosphate groups) might facilitate the duplex unwinding and double strand separation, since DNA duplex conformational changes are involved in many biological processes, such as DNA polymerization, DNA replication and transcription regulations.

Recently atoms with weak electron-negativity (e.g. Carbon) have gained more importance and acceptance as hydrogen-bond donors (such as C—H), although atoms with strong electron-negativity (e.g. oxygen and nitrogen) are traditionally considered in hydrogen bonding as hydrogen-bond donors (such as O—H and N—H). The interactions between donor C—H and hydrogen-bond acceptors (electron donors) [Singh, S. K., Babu, M. M. & Balaram, P. (2003) *Proteins* 51, 167-71; Uldry, A. C., Griffin, J. M., Yates, J. R., Perez-Torralba, M., Maria, M. D., Webber, A. L., Beaumont, M. L., Samoson, A., Claramunt, R. M., Pickard, C. J. & Brown, S. P. (2008) *J Am Chem Soc* 130, 945-54; Scheiner, S., Kar, T. & Gu, Y. (2001) *J Biol Chem* 276, 9832-7; Anbarasu, A., Anand, S. & Sethumadhavan, R. (2007) *Biosystems* 90, 792-801], such as C—H $\cdots$ O=C hydrogen bond in proteins [Singh, S. K., Babu, M. M. & Balaram, P. (2003) *Proteins* 51, 167-71], C—H $\cdots$ O=C in uracil crystal [Uldry, A. C., Griffin, J. M., Yates, J. R., Perez-Torralba, M., Maria, M. D., Webber, A. L., Beaumont, M. L., Samoson, A., Claramunt, R. M., Pickard, C. J. & Brown, S. P. (2008) *J Am Chem Soc* 130, 945-54] and C—H $\cdots$ Cl in a guest-host system [Li, Y. & Flood, A. H. (2008) *Angew Chem Int Ed Engl* 47, 2649-52], and other non-conventional interactions (such as H $\cdots \pi$C interaction in RNA) [Sarkhel, S., Rich, A. & Egli, M. (2003) *J Am Chem Soc* 125, 8998-9] have played critical roles in molecular recognition, catalysis, and DNA duplex stability within chemical and biological systems [Wang, S. & Kool, E. T. (1995) *Biochemistry* 34, 4125-32; Gesteland, R. F. C., T. R.; Atkins, J. F., Eds. (2006) *The RNA World: The Nature of Modern RNA Suggests a Prebiotic RNA*, ed. 3, (Cold Spring Harbor Laboratory Press Cold Spring Harbor, N.Y.); Singh, S. K., Babu, M. M. & Balaram, P. (2003) *Proteins* 51, 167-71; Uldry, A. C., Griffin, J. M., Yates, J. K, Perez-Torralba, M., Maria, M. D., Webber, A. L., Beaumont, M. L., Samoson, A., Claramunt, R. M., Pickard, C. J. & Brown, S. P. (2008) *J Am Chem Soc* 130, 945-54; Scheiner, S., Kar, T. & Gu, Y. (2001) *J Biol Chem* 276, 9832-7; Anbarasu, A., Anand, S. & Sethumadhavan, R. (2007) *Biosystems* 90, 792-801; Li, Y. & Flood, A. H. (2008) *Angew Chem Int Ed Engl* 47, 2649-52; Sarkhel, S., Rich, A. & Egli, M. (2003) *J Am Chem Soc* 125, 8998-9; Tewari, A. K. &

Dubey, R. (2008) *Bioorg Med Chem* 16, 126-43]. In addition, the 5-CH$_3$ group of thymidine in DNA can stack on a 5'-proceeding purine or pyrimidine via a CH$_2$—H···π (or CH$_3$···π) interaction [Umezawa, Y. & Nishio, M. (2002) *Nucleic Acids Res* 30, 2183-92; Chatterjee, S., Pathmasiri, W. & Chattopadhyaya, J. (2005) *Org Biomol Chem* 3, 3911-5], where the nucleobase functions as a weak hydrogen-bond acceptor, thereby further contributing to the duplex stability.

Tellurium is a non-metal element with a much larger atomic size (atomic radius: 1.40 Å) [L. Moroder, *J. Pept. Sci.* 2005, 11, 187-214] in the same elemental family of oxygen (0.73 Å), sulfur (1.02 Å) and selenium (1.16 Å) [J. Sheng, Z. Huang, *Int. J. Mol. Sci.* 2008, 9, 258-271], and has higher metallic property and stronger electron delocalizability. An electron-rich tellurium atom will likely donate electron and facilitate electron delocalization when it is introduced into DNA duplexes via nucleobases, which are relatively electron-deficient.

The nucleobases play the most critical roles in duplex recognition of nucleic acids. Well-behaved base-pair recognition and sequence-dependent specificity of DNAs and RNAs have stimulated extensive research investigations, such as DNA nano-structure construction and self-assembling [a) J: Zheng, J. J. Birktoft, Y. Chen, T. Wang, R. Sha, P. E. Constantinou, S. L. Ginell, C. Mao, N. C. Seeman, *Nature* 2009, 461, 74-77. b) E. S. Andersen, M. Dong, M. M. Nielsen, K. Jahn, R. Subramani, W. Mamdouh, M. M. Golas, B. Sander, H. Stark, C. L. Oliveira, J. S. Pedersen, V. Birkedal, F. Besenbacher, K. V. Gothelf, J. Kjems, *Nature* 2009, 459, 73-76. c) P. W. Rothemund, *Nature* 2006, 440, 297-302. d) X. Xue, F. Wang, X. Liu, *J. Am. Chem. Soc.* 2008, 130, 3244-3245], disease and pathogen detection at single molecule level [A. Singer, M. Wanunu, W. Morrison, H. Kuhn, M. Frank-Kamenetskii, A. Meller, *Nano. Lett.* 2010, 10, 738-742], oligonucleotide drug discovery [K. Tiemann, J. J. Rossi, *EMBO Mot. Med.* 2009, 1, 142-151], and nanoelectronic device design based on DNA conductivity and charge migration [a) Y. C. Huang, D. Sen, *J. Am. Chem. Soc.* 2010, 132, 2663-2671. b) I. Kratochvilova, K. Kral, M. Buncek, A. Viskova, S. Nespurek, A. Kochalska, T. Todorciuc, M. Weiter, B. Schneider, *Biophys. Chem.* 2008, 138, 3-10. c) T. Ito, S. E. Rokita, *Angew. Chem. Int. Ed.* 2004, 43, 1839-1842. d) R. N. Barnett, C. L. Cleveland, A. Joy, U. Landman, G. B. Schuster, *Science* 2001, 294, 567-571. e) D. Porath, A. Bezryadin, S. de Vries, C. Dekker, *Nature* 2000, 403, 635-638. f) H. W. Fink, C. Schonenberger, *Nature* 1999, 398, 407-410]. Moreover, chemical modifications of nucleobases have been widely used to selectively tailor the biochemical and biophysical properties of DNAs and RNAs and to probe their biochemical and biological mechanisms, including base-pairing specificity, polymerase recognition, and DNA damaging and repairing [a) Z. Yang, F. Chen, S. G. Chamberlin, S. A. Benner, *Angew. Chem. Int. Ed.* 2010, 49, 177-180. b) M. Egli, P. S. Pallan, *Chem. Biodivers.* 2010, 7, 60-89. c) A. E. Hassan, J. Sheng, W. Zhang, Z. Huang, *J. Am. Chem. Soc.* 2010, 132, 2120-2121. d) J. C. Delaney, J. Gao, H. Liu, N. Shrivastav, J. M. Essigmann, E. T. Kool, *Angew. Chem. Int. Ed. Engl.* 2009, 48, 4524-4527. e) M. Ljungman, *Chem. Rev.* 2009, 109, 2929-2950.1) A. M. Sismour, S. A. Benner, *Nucleic Acids Res.* 2005, 33, 5640-5646. g) T. W. Kim, J. C. Delaney, J. M. Essigmann, E. T. Kool, *Proc. Natl. Acad. Sci. USA* 2005, 102, 15803-15808]. Furthermore, the conductivity of DNAs has been studied extensively via nucleobase modification, metallization and conjugating with conductive nanoparticles or polymers through scanning tunneling microscopy (STM) imaging [I. Kratochvilova, I C Kral, M. Buncek, A. Viskova, S. Nespurek, A. Kochalska, T. Todorciuc, M. Weiter, B. Schneider, *Biophys. Chem.* 2008, 138.3-10; a) E. Braun, Y. Eichen, U. Sivan, G. Ben-Yoseph, *Nature* 1998, 391, 775-778. b) J. L. Coffer, S. R. Bigham, X. Li, R. F. Pinizzotto, Y. G. Rho, R. M. Pirtle, I. L. Pirtle, *Appl. Phys. Lett.* 1996, 69, 3851-3853. c) Y. F. Ma, J. M. Zhang, G. J. Zhang, H. X. He, *J. Am. Chem. Soc.* 2004, 126, 7097-7101. d) X. Guo, A. A. Gorodetsky, J. Hone, J. K. Barton, C. Nuckolls, *Nat. Nanotechnol.* 2008, 3, 163-167. e) B. Elias, F. Shao, J. K. Barton, *J. Am. Chem. Soc.* 2008, 130, 1152-1153].

Therefore, there is a need existing for the identification of new exo-5 position and/or 2-position modifications on the nucleobases of thymidine, ribothymidine, uridine, 2'-deoxyuridine, cytidine, 2'-deoxycytidine, and their derivatives in DNAs, RNAs and modified nucleic acids.

SUMMARY

Disclosed are compound of formula (I), or a tautomer thereof, or a pharmaceutically acceptable salt of said compound or said tautomer:

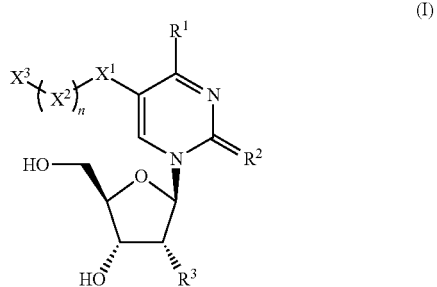

wherein:

R$_1$ is selected from the group consisting of is hydroxyl, thiol, alkylthiol, arylthiol, selenol, allylseleno, arylseleno, tellurol, alkyltelluro, aryltelluro, amino, alkylamino, arylamino and acylamino;

R$_2$ is selected from the group consisting of oxygen, sulfur, selenium, tellurium, amino, alkylamino, arylamino and acylamino;

R$_3$ is a hydrogen or a hydroxyl group;

X$_1$ is selected from the group consisting of oxygen, sulfur, selenium, tellurium, amino, alkylamino, arylamino, acylamino, carbon and hydrogen;

X$_2$ is linear or branched alkyl, or aryl;

X$_3$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, acylamino and acylamino; and N is a subscript selected from 0 to 20.

Also disclosed are methods of preparing compound of formula (I), or a tautomer thereof, or a pharmaceutically acceptable salt of said compound or said tautomer. Further disclosed are method of conducting drug discovery and research comprises applying the compound of formula (I), or a tautomer thereof, or a pharmaceutically acceptable salt of said compound or said tautomer in an investigation.

BRIEF DESCRIPTION OF THE DRAWINGS

The accompanying drawings, which are incorporated in and constitute a part of this specification, illustrate several forms and together with the description illustrate the disclosed compounds and methods.

FIG. 55. The STM images of the Te-modified DNA duplex [5'-ATGG($^{Te}$T)-GCTC-3' and 5'-(GAGCACCAT)$_6$-3'] on highly oriented pyrolytic graphite (HOPG). (A) Topographic image; (B) Current image.

DETAILED DESCRIPTION

Before the present compounds, compositions, articles, devices, and/or methods are disclosed and described, it is to be understood that they are not limited to specific synthetic methods or specific treatment methods unless otherwise specified, or to particular reagents unless otherwise specified, as such may, of course, vary. It is also to be understood that the terminology used herein is for the purpose of describing particular forms only and is not intended to be limiting.

Disclosed are new exo-5 position and/or 2-position modifications on the nucleobases of thymidine, ribothymidine, uridine, 2'-deoxyuridine, cytidine, 2'-deoxycytidine, and their derivatives in DNAs, RNAs and modified nucleic acids. Further disclosed are methods of synthesizing the novel thymidine, ribothymidine, uridine, 2'-deoxyuridine, cytidine, 2'-deoxycytidine and their derivatives containing exo-5-Se and/or 2-Se, the corresponding phosphoramidites and the Se-DNAs, Se-RNAs and the Se-modified nucleic acids. Also disclosed are methods of using the novel compounds for drug discovery and to design DNAs and RNAs that resist backbone digestion by nucleases, and research of siRNAs, microRNAs, antisense DNAs, and other oligonucleotides with nuclease resistance.

Figure 1A:
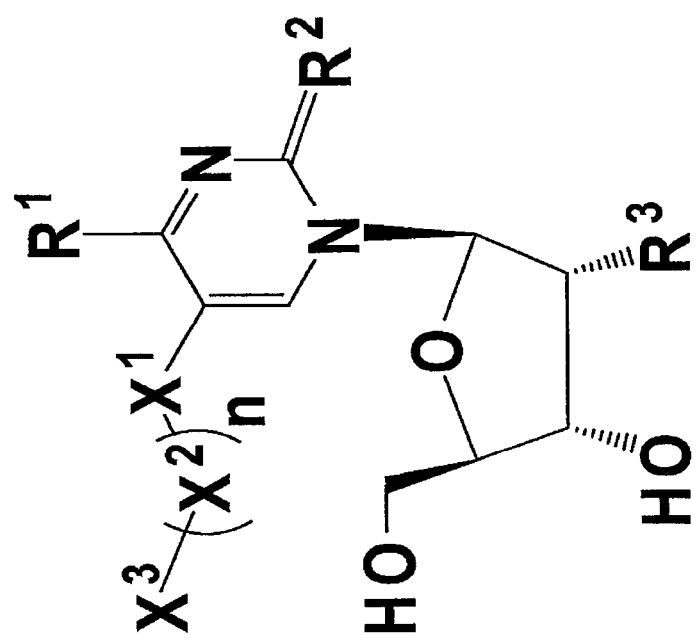
FIG. 1A. A representation of the chemical structure of the 5-Se-thymidine, 5-Se-uridine and 5-Se-cytidine analogs according to some forms of the disclosure.
Figure 1B:
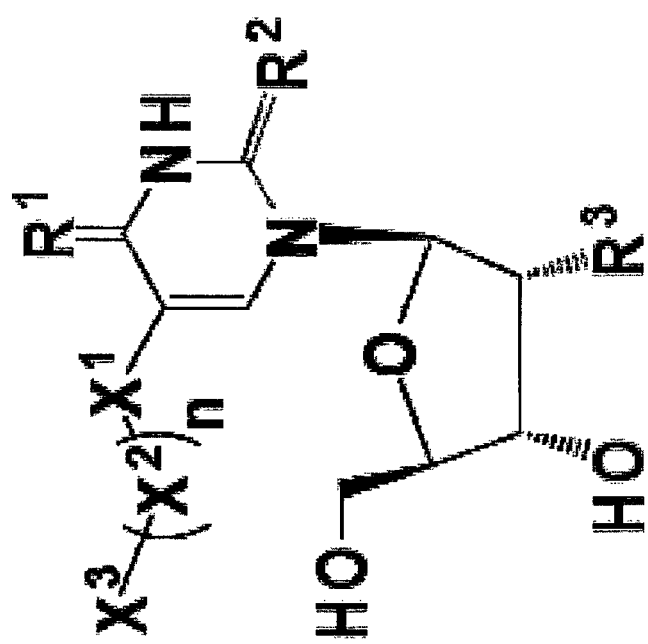
FIG. 1B. A representation of chemical structure of the 5-Se-thymidine and 5-Se-uridine, after tautomerization, according to some forms of the disclosure.
Figure 2A:
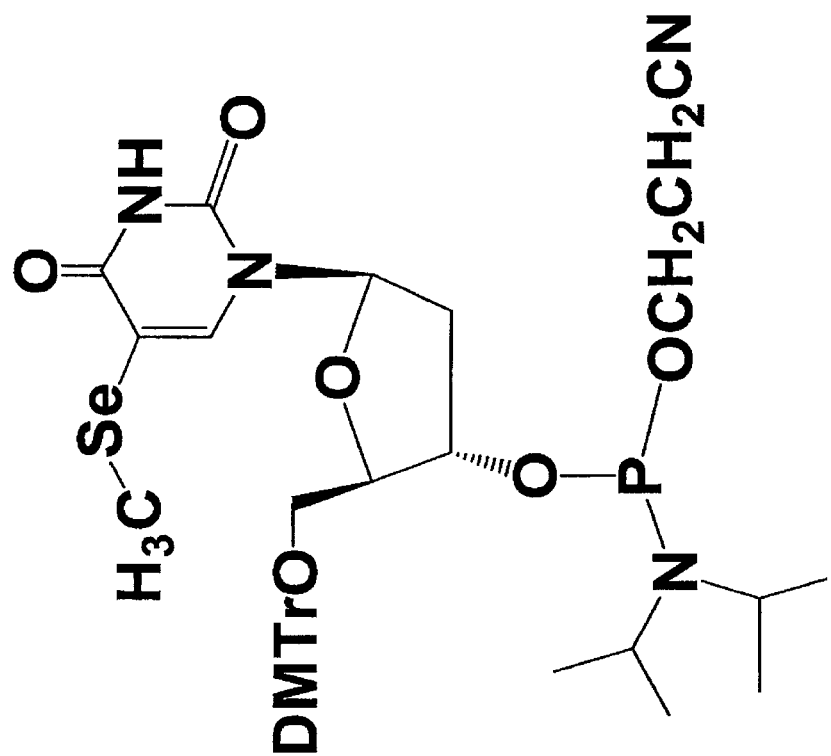
FIG. 2A. A representation of 5-Se-T phosphoramidite according to one embodiment of the disclosure.
Figure 2B:
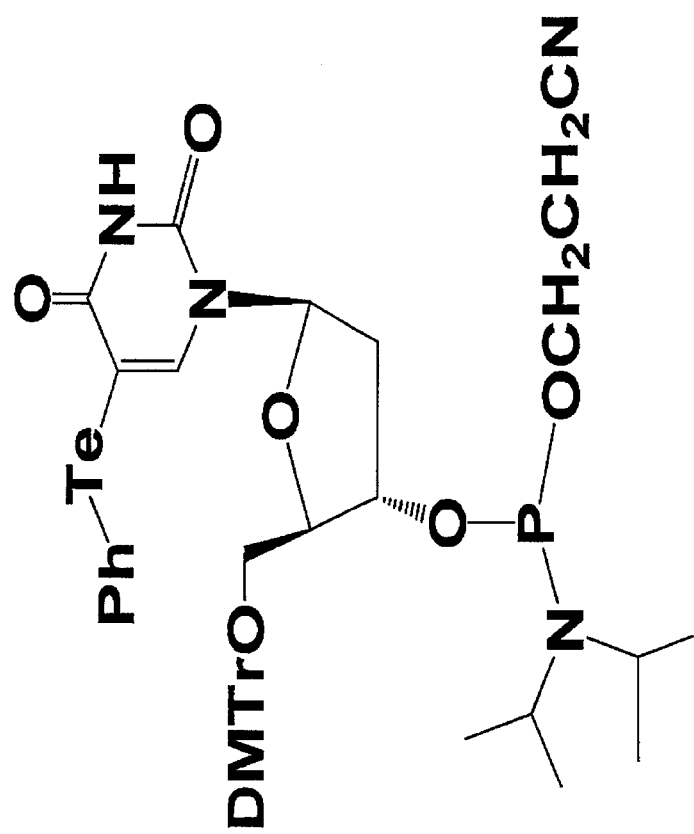
FIG. 2B. A representation of 5-Te-T phosphoramidite according to one embodiment of the disclosure.
Figure 3A:
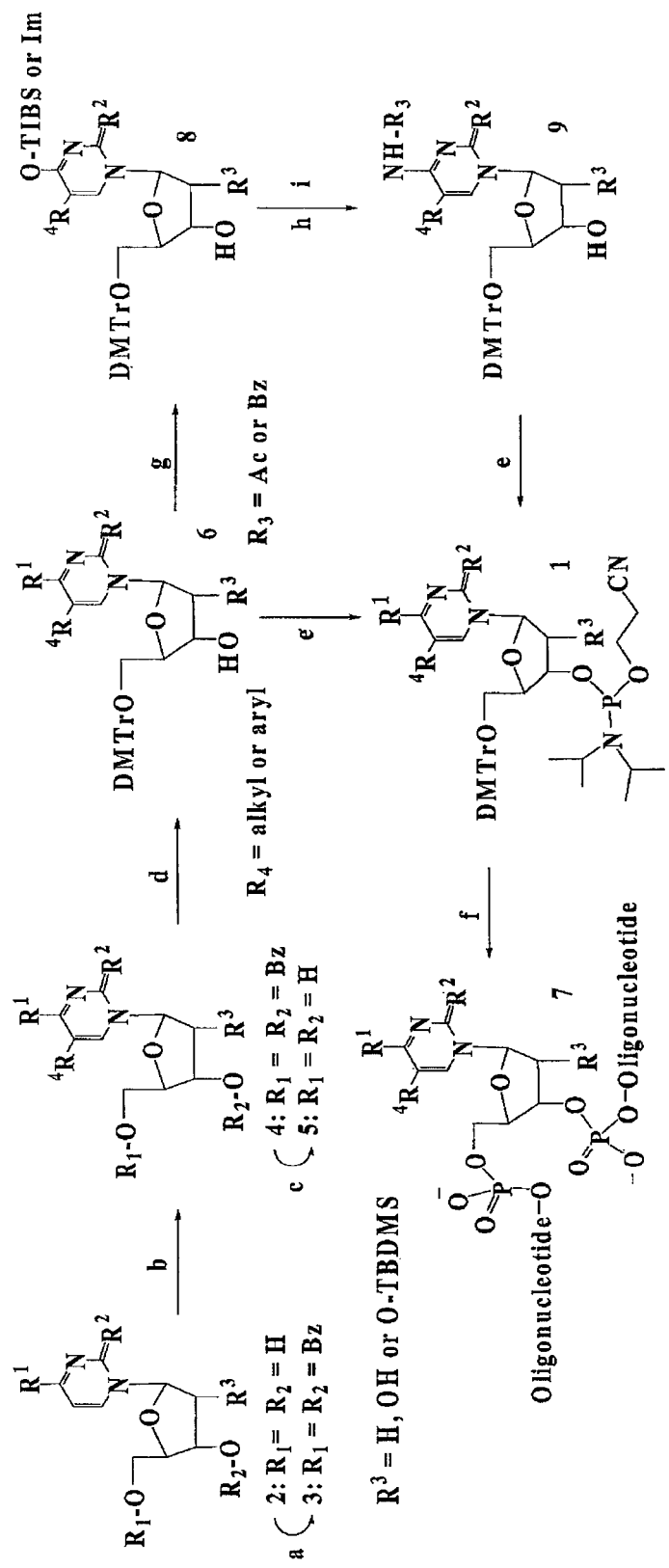
FIG. 3A. A representation of the synthesis of the compound of formula (I).
Figure 24:
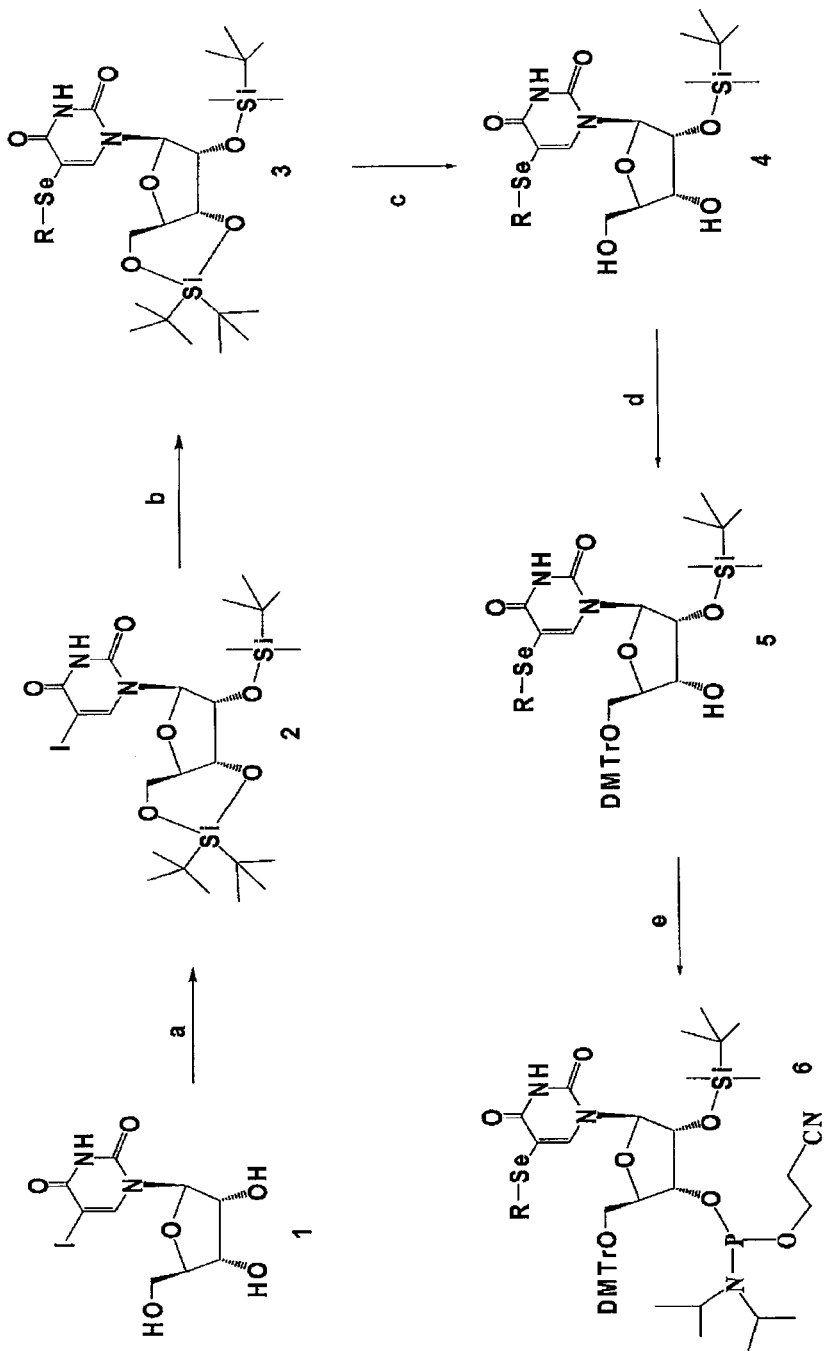
FIG. 24. Representation of the synthesis of 5-Se uridine and ribothymidine derivatives according to forms of the disclosure.

Disclosed is 5-Me-Se-thymidine phosphoramidite, shown as FIG. 2. Also disclosed is a method of synthesis of 5-Me-Se-thymidine or other phosphoramidites as shown in FIG. 3A. Also disclosed are compounds comprising 5-Me-Se-thymidine phosphoramidite incorporated into DNAs. Also disclosed is a method of using a modified DNA for the biophysical and structural studies of the DNAs containing the Te, Se, S or O-extended 5-CH$_3$. Also disclosed is a new site-specific insertion of a selenium atom at the 5-exo-positions of uridine and cytidine in both the 2'-deoxy and 2'-ribo series, for example, the 5-Se-ribouridine synthesis is shown in FIG. 24. Similarly to FIGS. 3 and 24, the synthesis of the 5-Se-ribocytidine and 5-Se-2'-deoxycytidine analogs can be achieved by using the 4-amino-protected ribocytidine and 2'-deoxycytidine derivatives as the starting materials. The synthesis shown in FIG. 24 can be accomplished using the following conditions and reagents: a) i) (tert-Bu)$_2$SiTf$_2$, DMF; ii) Im., TBDMS-Cl; b) NaH, THF, rt, 30 min, n-BuLi, –78° C., 30 min., RSeSeR, 1 h; c) HF.Pyridine, CH$_2$Cl$_2$, 0° C., 30 min., d) DMTr-Cl, DMAP, Pyridine; e) i-Pr$_2$NP(Cl)OCH$_2$CH$_2$CN, i-Pr$_2$NEt, CH$_2$Cl$_2$.

Disclosed are cytidine and uracil analogs and methods of synthesizing cytidine and uracil analogs comprising synthesizing the thymidine analog shown as (6) in FIG. 3A using the method of synthesis in FIG. 3A, and converting that thymidine analog to the corresponding cytidine or uracil analog. Also disclosed is that the obtained novel compounds can be used to investigate the DNA duplex flexibility, methylation function, and base-stacking interaction in a DNA duplex. For example, considering the variable distance (from 7.4 to 3.4 Å) between the thymine 5-CH$_3$ and 5'-phosphate pro-Sp oxygen in a DNA duplex, it can be envisioned that a negatively-charged phosphate group, which is a better hydrogen bond acceptor compared with an electron-deficient nucleobase, would be able to form a hydrogen bond interaction with the 5-CH$_3$ group of thymine in DNA under a certain spatial orientation or conformational circumstance. This hydrogen-bond switch between the CH$_3$···π and CH$_3$···PO$_4^-$ interactions, if it exists, could be involved in vital biological processes, such as the DNA duplex bending (curvature), conformational dynamics, unwinding, and separation of DNA double strands in DNA replication and RNA transcription. Compounds disclosed therein extend the 5-$CH_3$ group.

As discussed before, an electron-rich tellurium atom will likely donate electron and facilitate electron delocalization when it is introduced into DNA duplexes via nucleobases, which are relatively electron-deficient. Thus, in order to tailor and probe the impact of electron donation on base pairing, duplex recognition and electronic property of DNA, herein disclosed is the first synthesis of a tellurium-nucleobase derivatized nucleoside, the Te-phosphoramidite and Te-DNAs, following the success in synthesizing the 2'-tellurium-derivatized nucleosides [J. Sheng, A. E. Hassan, Z. Huang, *J. Org. Chem.* 2008, 73, 3725-3729.]and nucleotides [7. Sheng, A. E. Hassan, Z. Huang, *Chem-Eur. J.* 2009, 15, 10210-10216]. The biophysical and X-ray crystal structure studies of the Te-derivatized DNAs indicate that the Te-derivatized and native structures are virtually identical, and that the Te-modified T and native A pair as well as the native T and A nucleobases. Furthermore, the STM imaging study revealed that the Te-DNAs show strong characteristic current peaks on graphite surface, suggesting a high conductivity. The present findings also reveal the compatibility between the electron donation and base-pair-stability, suggesting a novel strategy to facilitate DNA conductivity without perturbing the local and over-all structures.

Disclosed is the successful synthesis of the first Te-nucleobase-modified nucleoside, phosphoramidite, and DNA oligonucleotides. The biophysical and structural studies indicate that the Te-modified T and A pair as well as native T and A, and that the Te-derivatized and native DNA duplex structures are virtually identical, which suggest that the electron donation to the nucleobase does not significantly alter the base pairing and duplex recognition. Comparing with the Ph-S modification causing the duplex destabilization, the Te modification and its electron delocalization contribute to the duplex stability. Furthermore, the STM studies suggest that the Te-DNA with higher conductivity may have great potentials in designing conductive nano-materials and molecular electronics. The investigations provide novel insight into nucleobase modification and recognition, which is the basis for probing and tailoring novel properties (such as conductivity) of nucleic acids. Furthermore, this Te-atom-specific modification and probing open a novel research avenue for nucleic acids, including crystal structure and function studies, STM imaging, and nano-electronic materials.

Materials

A. Compounds

Disclosed are compound of formula (I), or a tautomer thereof, or a pharmaceutically acceptable salt of said compound or said tautomer,

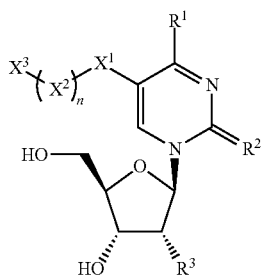

(I)

wherein:

$R_1$ is selected from the group consisting of is hydroxyl, thiol, alkylthiol, arylthiol, selenol, alkylseleno, arylseleno, tellurol, alkyltelluro, aryltelluro, amino, alkylamino, arylamino and acylamino;

$R_2$ is selected from the group consisting of oxygen, sulfur, selenium, tellurium, amino, alkylamino, arylamino and acylamino;

$R_3$ is a hydrogen or a hydroxyl group;

$X_1$ is selected from the group consisting of oxygen, sulfur, selenium, tellurium, amino, alkylamino, arylamino, acylamino, carbon and hydrogen;

$X_2$ is linear or branched alkyl, or aryl;

$X_3$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino; and N is a subscript selected from 0 to 20.

In some forms, the compound of formula (I) can be a compound wherein:

$R_1$ is seleno, alkylseleno, arylseleno, tellurol, alkyltelluro, or aryltelluro;

$R_2$ is selected from the group consisting of oxygen, sulfur, selenium, tellurium, amino, alkylamino, arylamino and acylamino;

$R_3$ is a hydrogen, or hydroxyl group;

$X_1$ is selected from the group consisting of oxygen, sulfur, selenium, tellurium, amino, alkylamino, arylamino, acylamino, carbon and hydrogen;

$X_2$ is linear or branched alkyl, or aryl;

$X_3$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino; and N is a subscript selected from 0 to 20.

In some other forms, the compound of formula (I) can be a compound wherein:

$R_1$ is selected from the group consisting of hydroxyl, thiol, alkylthiol, arylthiol, selenol, alkylseleno, arylseleno, tellurol, alkyltelluro, aryltelluro, amino, alkylamino, arylamino and acylamino;

$R_2$ is selenium or tellurium;

$R_3$ is a hydrogen, or hydroxyl group;

$X_1$ is selected from the group consisting of oxygen, sulfur, selenium, tellurium, amino, alkylamino, arylamino, acylamino, carbon and hydrogen;

$X_2$ is linear or branched alkyl, or aryl;

$X_3$ is selected from the group consisting of hydrogen, halogen, alkyl, aryl, hydroxyl, thiol, amino, alkyloxyl, aryloxyl, acyloxyl, allylthiol, arylthiol, alkylseleno, arylseleno, alkyltelluro, aryltelluro, alkylamino, arylamino and acylamino; and N is a subscript selected from 0 to 20.

In some other forms, the compound of formula (I) can be a compound wherein:

$R_1$ is selected from the group consisting of hydroxyl, thiol, alkylthiol, arylthiol, selenol, alkylseleno, arylseleno, tellurol, alkyltelluro, aryltelluro, amino, alkylamino, arylamino and acylamino;

$R_2$ is selected from the group consisting of oxygen, sulfur, selenium, tellurium, amino, alkylamino, arylamino and acylamino;

$R_3$ is a hydrogen, or hydroxyl group;

$X_1$ is selenium or tellurium;

$X_2$ is linear or branched alkyl, or aryl;

$X_3$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino; and N is a subscript selected from 0 to 20.

In some forms, the compound of formula (I) can tautomerize to form a tautomer of the compound of formula (I) where said tautomer has a formula (II):

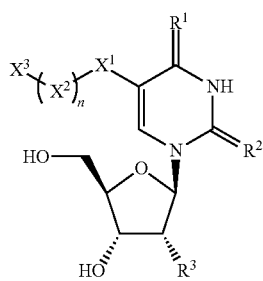

(II)

wherein:

$R_1$ is selected from the group consisting of is oxygen, sulfur, selenium, tellurium, amino, alkylamino, arylamino and acylamino;

$R_2$ is selected from the group consisting of oxygen, sulfur, selenium, tellurium, amino, alkylamino, arylamino and acylamino;

$R_3$ is a hydrogen or a hydroxyl group;

$X_1$ is selected from the group consisting of oxygen, sulfur, selenium, tellurium, amino, alkylamino, arylamino, acylamino, carbon and hydrogen;

$X_2$ is linear or branched alkyl, or aryl;

$X_3$ is selected from the group consisting of hydrogen, halogen, alkyl, aryl, hydroxyl, thiol, amino, alkyloxyl, aryloxyl, acyloxyl, alkylthiol, arylthiol, allylseleno, arylseleno, alkyltelluro, aryltelluro, alkylamino, arylamino and acylamino; and N is a subscript selected from 0 to 20.

In some forms, the compound of formula (I) can be a compound wherein said compound comprises a nucleobase which is selected from thymidine, ribothymidine, uridine, 2'-deoxyuridine, cytidine and 2'-deoxycytidine. In some other forms, a derivative of the compound of formula (I) can be a compound of formula (III):

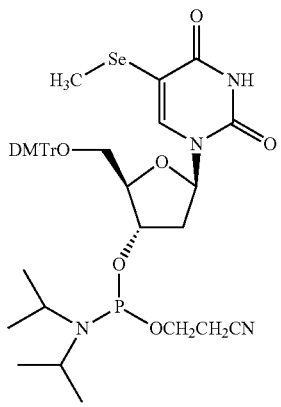

(III)

wherein DMTr represents dimethoxytrityl.

In some other forms, a derivative of the compound of formula (I) can be a compound of formula (IV):

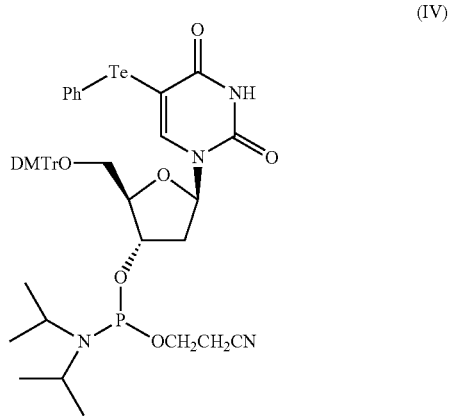

(IV)

wherein DMTr represents dimethoxytrityl.

In some other forms, a derivative of the compound of formula (I) can be an oligonucleotide, DNA, or RNA. For the above derivative; the compound of formula (III and IV) is used as building blocks to construct the oligonucleotides, DNAs, or RNAs.

1. Isomers

When an asymmetric center is present in a compound of formula I or a derivative of the compound of formula I, hereinafter referred to as the disclosed compounds, the compound may exist in the form of optical isomers (enantiomers). In some forms, the disclosed compounds and compositions can comprise enantiomers and mixtures, including racemic mixtures of the compounds of formula I. In some forms, for compounds of formula I that contain more than one asymmetric center, the disclosed compounds and compostions can comprise diastereomeric forms (individual diastereomers and mixtures thereof) of compounds. When a compound of formula I contains an alkenyl group or moiety, geometric isomers may arise.

2. Tautomeric Forms

The disclosed compounds comprise the tautomeric forms of compounds of formula I. Where structural isomers are interconvertible via a low energy barrier, tautomeric isomerism ('tautomerism') can occur. This can take the form of proton tautomerism in compounds of formula I containing, for example, an imino, keto, or oxime group, or so-called valence tautomerism in compounds which contain an aromatic moiety. It follows that a single compound may exhibit more than one type of isomerism. The various ratios of the tautomers in solid and liquid form are dependent on the various substituents on the molecule as well as the particular crystallization technique used to isolate a compound.

3. Salts

The disclosed compounds can be used in the form of salts derived from inorganic or organic acids. Depending on the particular compound, a salt of the compound can be advantageous due to one or more of the salt's physical properties, such as enhanced pharmaceutical stability in differing temperatures and humidities, or a desirable solubility in water or oil. In some instances, a salt of a compound can also be used as an aid in the isolation, purification, and/or resolution of the compound.

Where a salt is intended to be administered to a patient (as opposed to, for example, being used in an in vitro context), the salt preferably is pharmaceutically acceptable. The term "pharmaceutically acceptable salt" refers to a salt prepared by combining a compound, such as the disclosed compounds, with an acid whose anion, or a base whose cation, is generally considered suitable for human consumption. Pharmaceutically acceptable salts are particularly. useful as products of the disclosed methods because of their greater aqueous solubility relative to the parent compound. For use in medicine, the salts of the disclosed compounds are non-toxic "pharmaceutically acceptable salts." Salts encompassed within the term "pharmaceutically acceptable salts" refer to non-toxic salts of the disclosed compounds which are generally prepared by reacting the free base with a suitable organic or inorganic acid.

Suitable pharmaceutically acceptable acid addition salts of the disclosed compounds, when possible include those derived from inorganic acids, such as hydrochloric, hydrobromic, hydrofluoric, boric, fluoroboric, phosphoric, metaphosphoric, nitric, carbonic, sulfonic, and sulfuric acids, and organic acids such as acetic, benzenesulfonic, benzoic, citric, ethanesulfonic, fumaric, gluconic, glycolic, isothionic, lactic, lactobionic, maleic, malic, methanesulfonic, trifluoromethanesulfonic, succinic, toluenesulfonic, tartaric, and trifluoroacetic acids. Suitable organic acids generally include, for example, aliphatic, cycloaliphatic, aromatic, araliphatic, heterocyclylic, carboxylic, and sulfonic classes of organic kids.

Specific examples of suitable organic acids include acetate, trifluoroacetate, formate, propionate, succinate, glycolate, gluconate, digluconate, lactate, malate, tartaric acid, citrate, ascorbate, glucuronate, maleate, fumarate, pyruvate, aspartate, glutamate, benzoate, anthranilic acid, mesylate, stearate, salicylate, p-hydroxybenzoate, phenylacetate, mandelate, embonate (pamoate), methanesulfonate, ethanesulfonate, benzenesulfonate, pantothenate, toluenesulfonate, 2-hydroxyethanesulfonate, sufanilate, cyclohexylaminosulfonate, algenic acid, β-hydroxybutyric acid, galactarate, galacturonate, adipate, alginate, butyrate, camphorate, camphorsulfonate, cyclopentanepropionate, dodecylsulfate, glycoheptanoate, glycerophosphate, heptanoate, hexanoate, nicotinate, 2-naphthalesulfonate, oxalate, palmoate, pectinate, 3-phenylpropionate, picrate, pivalate, thiocyanate, tosylate, and undecanoate.

Furthermore, where the disclosed compounds carry an acidic moiety, suitable pharmaceutically acceptable salts thereof can include alkali metal salts, e.g., sodium or potassium salts; alkaline earth metal salts, e.g., calcium or magnesium salts; and salts formed with suitable organic ligands, e.g., quaternary ammonium salts. In some forms, base salts are formed from bases which form non-toxic salts, including aluminum, arginine, benzathine, choline, diethylamine, diolamine, glycine, lysine, meglumine, olamine, tromethamine and zinc salts.

Organic salts can be made from secondary, tertiary or quaternary amine salts, such as tromethamine, diethylamine, N,N'-dibenzylethylenediamine, chloroprocaine, choline, diethanolamine, ethylenediamine, meglumine (N-methylglucamine), and procaine. Basic nitrogen-containing groups can be quaternized with agents such as lower alkyl(C1-C6) halides (e.g., methyl, ethyl, propyl, and butyl chlorides, bromides, and iodides), dialkyl sulfates (e.g., dimethyl, diethyl, dibuytl, and diamyl sulfates), long chain halides (e.g., decyl, lauryl, myristyl, and stearyl chlorides, bromides, and iodides), arylalkyl halides (e.g., benzyl and phenethyl bromides), and others. In some forms, hemisalts of acids and bases can also be formed, for example, hemisulphate and hemicalcium salts. The disclosed compounds can exist in both unsolvated and solvated forms. A "solvate" as used herein is a nonaqueous solution or dispersoid in which there is a noncovalent or easily dispersible combination between solvent and solute, or dispersion means and disperse phase.

4. Prodrugs

Also disclosed are so-called "prodrugs" of the disclosed compounds. Thus, certain derivatives of the disclosed compounds which have little or no pharmacological activity themselves can, when administered into or onto the body, be converted into the disclosed compounds having the desired activity, for example, by hydrolytic cleavage. Such derivatives are referred to as "prodrugs." Further information on the use of prodrugs can be found in "Pro-drugs as Novel Delivery Systems, Vol. 14, ACS Symposium Series (T Higuchi and W Stella) and "Bioreversible Carriers in Drug Design," Pergamon Press, 1987 (ed. E B Roche, American Pharmaceutical Association). Prodrugs as disclosed herein can, for example, be produced by replacing appropriate functionalities present in the compounds of formula I with certain moieties known to those skilled in the art as "pro-moieties" as described, for example, in "Design of Prodrugs" by H. Bundgaard (Elsevier, 1985).

5. Isotopes

Also disclosed are isotopically labelled compounds, which are identical to those compounds recited in formula I, but for the fact that one or more atoms are replaced by an atom having an atomic mass or mass number different from the atomic mass or mass number usually found in nature. Examples of isotopes that can be incorporated into disclosed compounds include isotopes of hydrogen, carbon, nitrogen, oxygen, phosphorous, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$, and $^{36}Cl$, respectively. Disclosed compounds, prodrugs thereof and pharmaceutically acceptable salts of said compounds or of said prodrugs which contain the aforementioned isotopes and/or other isotopes of other atoms are contemplated. Certain isotopically labelled disclosed compounds, for example those into which radioactive isotopes such as $^{3}H$ and $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labelled compounds of formula I (and other disclosed compounds) and prodrugs thereof can generally be prepared by carrying out the procedures disclosed in the Schemes and/or in the Examples and Preparations below, by substituting a readily available isotopically labelled reagent for a non-isotopically labelled reagent.

6. General Synthetic Schemes

The compounds of the formula I (and other disclosed compounds), or the derivatives of the compounds of formula I, or the pharmaceutically acceptable salts of the compounds and derivatives of the compounds of formula I, can be prepared by the methods as illustrated by general reaction schemes shown below, by examples described in the "Examples" section, together with synthetic methods known in the art of organic chemistry, or modifications and derivatisations that are familiar to those of ordinary skill in the art. The starting materials used herein are commercially available or can be prepared by routine methods known in the art (such as those methods disclosed in standard reference books such as the COMPENDIUM OF ORGANIC SYNTHETIC METHODS, Vol. I-VI (published by Wiley-Interscience)). Preferred methods include, but are not limited to, those described below. During any of the following synthetic sequences it may be necessary and/or desirable to protect sensitive or reactive groups on any of the molecules concerned. This can be achieved by means of conventional protecting groups, such as those described in T.

W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference. Isolation and purification of the products is accomplished by standard procedures, which are known to a chemist of ordinary skill.

A general reaction scheme for the preparation of the compound of formula I or the derivative of such compound is illustrated in scheme 1:

nucleophilic addition and elimination in Scheme 3; compound 4 is deprotected to provide compound 5; compound 5 is converted to compound 6 via tritylation; compound 6 is converted to compound 1 via phosphitylation; alternatively, compound 6 is converted to compound 8 and compound 9 in sequence by transforming a camonyl group to an amino group, and compound 9 is converted to compound 1 via phosphitylation; and compound 1 is converted to compound 7 via solid phase synthesis

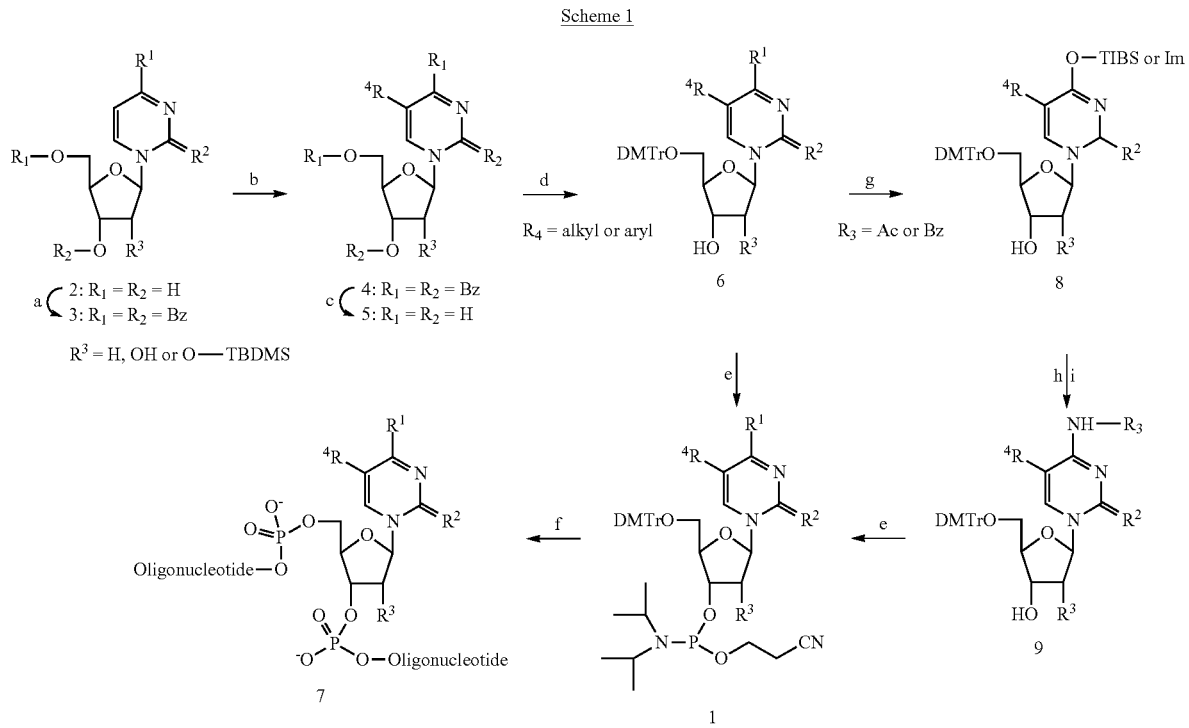

Scheme 1 where compound 2 is protected via benzoylation to provide compound 3; compound 3 is converted to compound 4 in Scheme 1, via electrophilic addition and elimination in the presence of an electrophile activator in Scheme 2, or via Another general reaction scheme for the preparation of the compound of formula I or the derivative of such compound is illustrated in scheme 2:

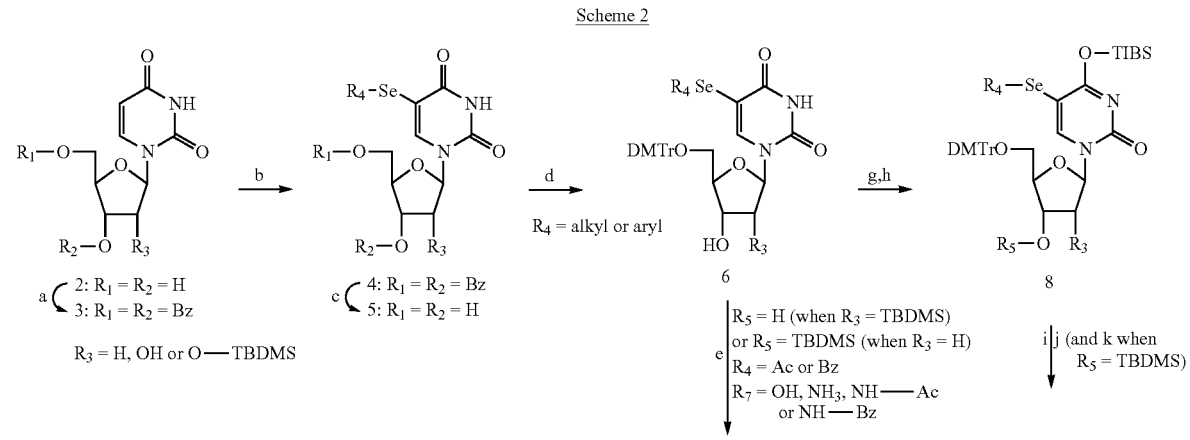

Scheme 2

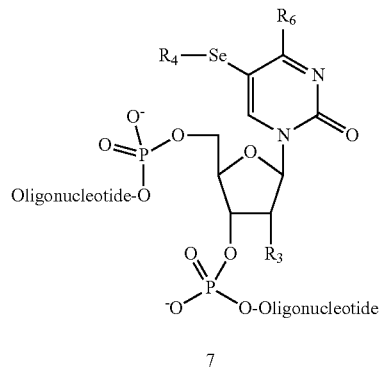
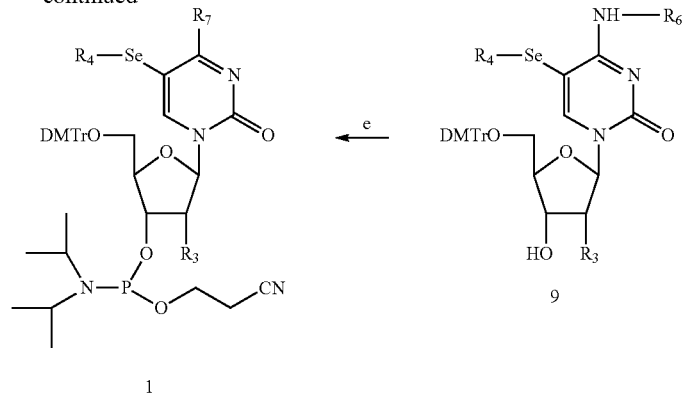

in which selenium is introduced to the 5 position of uracil.

Another general reaction scheme for the preparation of the compound of formula I or the derivative of such compound according to the above schemes 1 and 2 is wherein 2'-deoxyuridine (2) is protected via benzoylation to provide 3',5'-di-O-benzoyl-2'-deoxyuridine (3); 3',5'-di-O-benzoyl-2'-deoxyuridine is treated with $CH_3SeSeCH_3$ in the presence of $Mn(OAc)_3$ to provide 3',5'-Di-O-benzoyl-5-seleno-thymidine (4); 3',5'-Di-O-benzoyl-5-seleno-thymidine is deprotected to provide 2'-deoxy-5-methyl-selenyluridine (5); 2'-deoxy-5-methyl-selenyluridine is treated with 4,4-dimethoxytrityl chloride to provide 5'-O-(4,4'-dimethoxytrityl)-5-seleno-thymidine (6); and 5'-O-(4,4'-dimethoxytrityl)-5-seleno-thymidine is treated with 2-cyanoethyl-N,N,N,N-tetraisopropyl phosphane to provide 3'-O-(2-cyanoethyl-N,N-diisopropylamino)-phosphoramidite-5'-O-(4,4'-dimethoxytrityl-5-seleno-thymidine (1).

Another general reaction scheme for the preparation of the compound of formula I or the derivative of such compound is illustrated in scheme 3:

Scheme 3

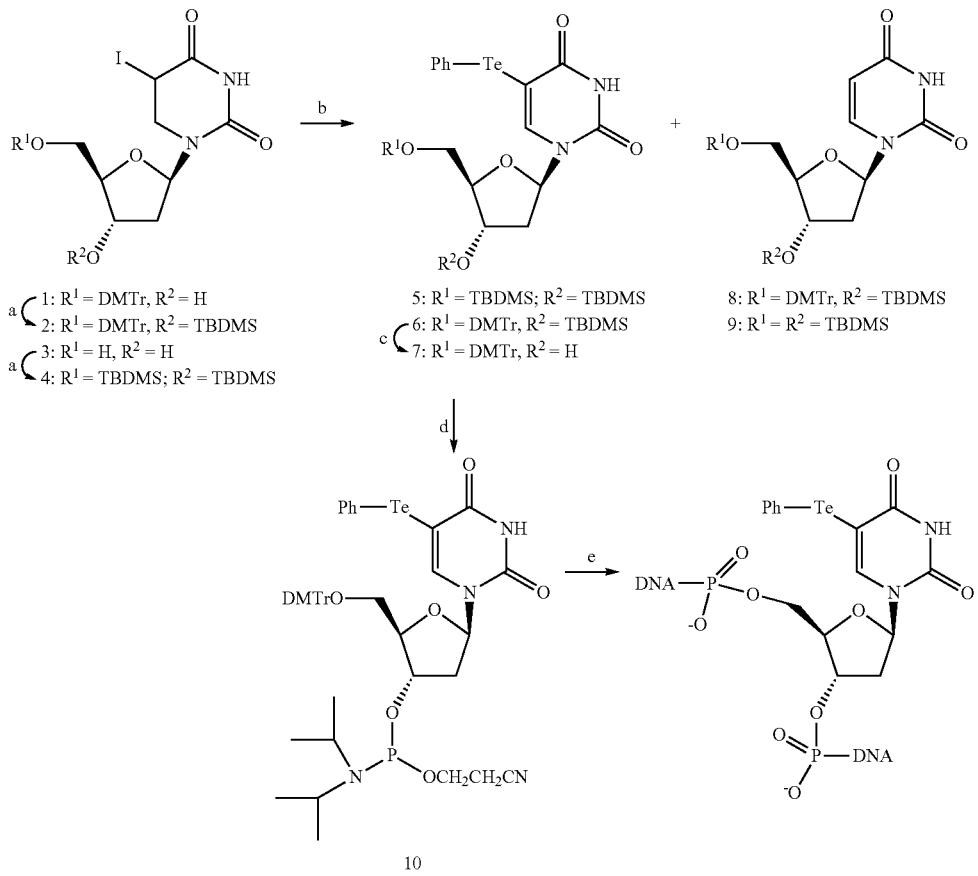

in which 5-iodo-2'-deoxyuridine derivative 1 or 3 is protected by TBDMS, and the resulting compound is treated by NaH and followed by n-BuLi and (PhTe)$_2$ treatment to provide 5-phenyltelluro derivative 6; then desilylation of compound 6 provides compound 7; and compound 7 is transformed into the 5-phenyltelluro thymdine ($^{Te}$T) phosphoramidite 10; and compound 10 is converted to Te-DNAs via solid phase synthesis.

Another general reaction scheme for the preparation of the compound of formula I or the derivative of such compound, according to the above scheme 3 is wherein reactions conditions applied in reactions steps (a) to (e) are: (a) TBDMS-Cl, Im., DMF, 4 h, room temperature (RT); (b) i) NaH, THF, 15 min, RT; ii), n-BuLi, THF, 10 min., −78° C.; iii) Ph$_2$Te$_2$, 1 h, −78° C.; (c) TBAF, THF, 4 h, RT; (d) i-Pr$_2$NP(Cl)CH$_2$CH$_2$CN, DIEA, CH$_2$Cl$_2$, 1 h, RT; (e) the solid-phase synthesis.

Methods

The above-described compounds, derivatives of the compounds, or the pharmaceutically acceptable salt of the compounds and the derivatives are useful for conducting drug discovery and research. Accordingly, in some forms, disclosed are methods of conducting drug discovery and research wherein said methods comprises applying the compound of formula I, and/or the derivative of the compound in an investigation. In some other forms, the investigation involves studying DNA duplex flexibility, methylation function, or base-stacking interaction in a DNA duplex. In some other forms, the investigation involves studying one or more biological processes selected from a group consisting of DNA duplex bending (curvature), conformational dynamics, unwinding, separation of DNA double strands in DNA replication and RNA transcription. In some other forms, the investigation involves designing DNAs and/or RNAs which resist backbone digestion by nucleases. In some other forms, the investigation involves conducting research on the DNAs and/or RNAs. The DNAs and/or RNAs is selected from the group consisting of siRNAs, microRNAs, antisense DNAs, and other oligonucleotides with nuclease resistance.

A. Definitions

1. A, an, the

As used in the specification and the appended claims, the singular forms "a," "an" and "the" include plural referents unless the context clearly dictates otherwise. Thus, for example, reference to "a pharmaceutical carrier" includes mixtures of two or more such carriers, and the like.

2. Cell

The term "cell" as used herein also refers to individual cells, cell lines, or cultures derived from such cells. A "culture" refers to a composition comprising isolated cells of the same or a different type. The term co-culture is used to designate when more than one type of cell are cultured together in the same dish with either full or partial contact with each other.

3. Complex

The term complex as used herein refers to the association of a compound with an ion channel or enzyme for which the compound has a binding affinity.

4. Compound

For the purposes of the present disclosure the terms "compound," "analog," and "composition of matter" stand equally well for the chemical entities described herein, including all enantiomeric forms, diastereomeric forms, salts, and the like, and the terms "compound," "analog," and "composition of matter" are used interchangeably throughout the present specification.

5. Comprise

Throughout the description and claims of this specification, the word "comprise" and variations of the word, such as "comprising" and "comprises," means "including but not limited to," and is not intended to exclude, for example, other additives, components, integers or steps.

6. Components

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. Thus, if a class of molecules A, B, and C are disclosed as well as a class of molecules D, E, and F and an example of a combination molecule, A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific form or combination of forms of the disclosed methods.

7. Chemistry

The term "alkyl" refers to a linear or branched-chain saturated hydrocarbyl substituent (i.e., a substituent obtained from a hydrocarbon by removal of a hydrogen) containing from one to twenty carbon atoms; in some forms from one to twelve carbon atoms; in some forms, from one to ten carbon atoms; in some forms, from one to six carbon atoms; and in some forms, from one to four carbon atoms. Examples of such substituents include methyl, ethyl, propyl (including n-propyl and isopropyl), butyl (including n-butyl, isobutyl, sec-butyl and tert-butyl), pentyl, iso-amyl, hexyl and the like.

The term "alkenyl" refers to a linear or branched-chain hydrocarbyl substituent containing one or more double bonds and from two to twenty carbon atoms; in some forms, from two to twelve carbon atoms; in some forms, from two to six carbon atoms; and in some forms, from two to four carbon atoms. Examples of alkenyl include ethenyl (also known as vinyl), allyl, propenyl (including 1-propenyl and 2-propenyl) and butenyl (including 1-butenyl, 2-butenyl and 3-butenyl). The term "alkenyl" embraces substituents having "cis" and "trans" orientations, or alternatively, "E" and "Z" orientations.

The term "benzyl" refers to methyl radical substituted with phenyl, i.e., the following structure

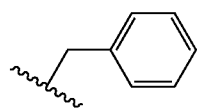 [SMILES: *Cc1ccccc1]

The term "cycloalkyl" refers to a saturated carbocyclic substituent having three to fourteen carbon atoms. In some forms, a cycloalkyl substituent has three to ten carbon atoms. Examples of cycloalkyl include cyclopropyl, cyclobutyl, cyclopentyl and cyclohexyl.

The term "cycloalkyl" also includes substituents that are fused to a $C_6$-$C_{10}$ aromatic ring or to a 5-10-membered heteroaromatic ring, wherein a group having such a fused cycloalkyl group as a substituent is bound to a carbon atom of the cycloalkyl group. When such a fused cycloalkyl group is substituted with one or more substituents, the one or more substituents, unless otherwise specified, are each bound to a carbon atom of the cycloalkyl group. The fused $C_6$-$C_{10}$ aromatic ring or to a 5-10-membered heteroaromatic ring can be optionally substituted with halogen, $C_1$-$C_6$ alkyl, $C_3$-$C_{10}$ cycloalkyl, or =O.

The term "cycloalkenyl" refers to a partially unsaturated carbocyclic substituent having three to fourteen carbon atoms, typically three to ten carbon atoms. Examples of cycloalkenyl include cyclobutenyl, cyclopentenyl, and cyclohexenyl.

A cycloalkyl or cycloalkenyl can be a single ring, which typically contains from 3 to 6 ring atoms. Examples include cyclopropyl, cyclobutyl, cyclopentyl, cyclopentenyl, cyclopentadienyl, cyclohexyl, cyclohexenyl, cyclohexadienyl, and phenyl. Alternatively, 2 or 3 rings can be fused together, such as bicyclodecanyl and decalinyl.

The term "aryl" refers to an aromatic substituent containing one ring or two or three fused rings. The aryl substituent can have six to eighteen carbon atoms. As an example, the aryl substituent can have six to fourteen carbon atoms. The term "aryl" can refer to substituents such as phenyl, naphthyl and anthracenyl. The term "aryl" also includes substituents such as phenyl, naphthyl and anthracenyl that are fused to a $C_4$-$C_{10}$ carbocyclic ring, such as a $C_5$ or a $C_6$ carbocyclic ring, or to a 4-10-membered heterocyclic ring, wherein a group having such a fused aryl group as a substituent is bound to an aromatic carbon of the aryl group. When such a fused aryl group is substituted with one more substituents, the one or more substituents, unless otherwise specified, are each bound to an aromatic carbon of the fused aryl group. The fused $C_4$-$C_{10}$ carbocyclic or 4-10-membered heterocyclic ring can be optionally substituted with halogen, $C_1$-$C_6$ alkyl, $C_3$-$C_{10}$ cycloalkyl, or =O. Examples of aryl groups include accordingly phenyl, naphthalenyl, tetrahydronaphthalenyl (also known as "tetralinyl"), indenyl, isoindenyl, indanyl, anthracenyl, phenanthrenyl, benzonaphthenyl (also known as "phenalenyl"), and fluorenyl.

The term "hydrogen" refers to hydrogen substituent, and can be depicted as —H.

The term "hydroxy" refers to —OH. When used in combination with another term(s), the prefix "hydroxy" indicates that the substituent to which the prefix is attached is substituted with one or more hydroxy substituents. Compounds bearing a carbon to which one or more hydroxy substituents include, for example, alcohols, enols and phenol.

The term "hydroxyalkyl" refers to an alkyl that is substituted with at least one hydroxy substituent. Examples of hydroxyalkyl include hydroxymethyl, hydroxyethyl, hydroxypropyl and hydroxybutyl.

The term "nitro" means —$NO_2$.

The term "cyano" (also referred to as "nitrile")—CN, which also can be depicted: 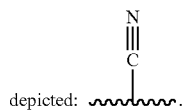

The term "carbonyl" means —C(O)—, which also can be depicted as:

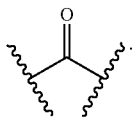

The term "amino" refers to —$NH_2$.

The term "alkylamino" refers to an amino group, wherein at least one alkyl chain is bonded to the amino nitrogen in place of a hydrogen atom. Examples of alkylamino substituents include monoalkylamino such as methylamino (exemplified by the formula —NH($CH_3$)), which can also be depicted:

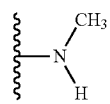

and dialkylamino such as dimethylamino, exemplified by the formula —N($CH_3$)$_2$, which can also be depicted:

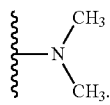

The term "aminocarbonyl" means —C(O)—$NH_2$, which also can be depicted as:

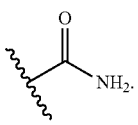

The term "halogen" refers to fluorine (which can be depicted as —F), chlorine (which can be depicted as —Cl), bromine (which can be depicted as —Br), or iodine (which can be depicted as —I). In some forms, the halogen is chlorine. In some forms, the halogen is a fluorine.

The prefix "halo" indicates that the substituent to which the prefix is attached is substituted with one or more independently selected halogen substituents. For example, haloalkyl refers to an alkyl that is substituted with at least one halogen substituent. Where more than one hydrogen is replaced with halogens, the halogens can be identical or different. Examples of haloalkyls include chloromethyl, dichloromethyl, difluorochloromethyl, dichlorofluoromethyl, trichloromethyl, 1-bromoethyl, fluoromethyl, difluoromethyl, trifluoromethyl, 2,2,2-trifluoroethyl, difluoroethyl, pentafluoroethyl, difluompropyl, dichloropropyl, and heptafluoropropyl. Illustrating further, "haloalkoxy" refers to an alkoxy that is substituted with at least one halogen substituent Examples of haloalkoky substituents include chloromethoxy, 1-bromoethoxy, fluoromethoxy, difluommethoxy, trifluoromethoxy (also known as "perfluoromethyloxy"), and 2,2,2-trifluoroethoxy. It should be recognized that if a substituent is substituted by more than one halogen substituent, those halogen substituents can be identical or different (unless otherwise stated).

The term "oxo" refers to =O.

The term "oxy" refers to an ether substituent, and can be depicted as —O—.

The term "alkoxy" refers to an alkyl linked to an oxygen, which can also be represented as —O—R, wherein the R represents the alkyl group. Examples of alkoxy include methoxy, ethoxy, propoxy and butoxy.

The term "alkylthio" means —S-alkyl. For example, "methylthio" is —S—$CH_3$. Other examples of alkylthio include ethylthio, propylthio, butylthio, and hexylthio.

The term "alkylcarbonyl" means —C(O)-alkyl. For example, "ethylcarbonyl" can be depicted as:

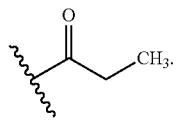 [SMILES: *C(=O)CC]

Examples of other alkylcarbonyl include methylcarbonyl, propylcarbonyl, butylcarbonyl, pentylcabonyl, and hexylcarbonyl.

The term "aminoalkylcarbonyl" means —C(O)-alkyl-$NH_2$. For example, "aminomethylcarbonyl" can be depicted as:

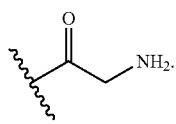

The term "alkoxycarbonyl" means —C(O)—O-alkyl. For example, "ethoxycarbonyl" can be depicted as:

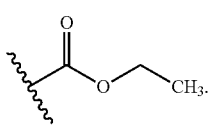 [SMILES: *C(=O)OCC]

Examples of other alkoxycarbonyl include methoxycarbonyl, ethoxycarbonyl, propoxycarbonyl, butoxycarbonyl, pentoxycarbonyl, and hexyloxycarbonyl. In some forms, where the carbon atom of the carbonyl is attached to a carbon atom of a second alkyl, the resulting functional group is an ester.

The terms "thio" and "thia" mean a divalent sulfur atom and such a substituent can be depicted as —S—. For example, a thioether is represented as "alkyl-thio-alkyl" or, alternatively, alkyl-S-alkyl.

The term "thiol" refers to a sulfhydryl substituent, and can be depicted as —SH.

The term "thione" refers to =S.

The term "sulfonyl" refers to —$S(O)_2$—, which also can be depicted as:

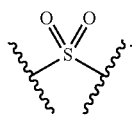

Thus, for example, "alkyl-sulfonyl-alkyl" refers to alkyl-S$(O)_2$-alkyl. Examples of alkylsulfonyl include methylsulfonyl, ethylsulfonyl, and propylsulfonyl.

The term "aminosulfonyl" means —$S(O)_2$—$NH_2$, which also can be depicted as:

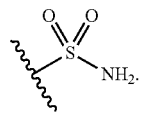

The term "sulfinyl" or "sulfoxido" means —S(O)—, which also can be depicted as:

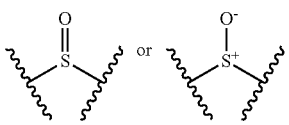

Thus, for example, "alkylsulfinylalkyl" or "alkylsulfoxidoalkyl" refers to alkyl-S(O)-alkyl. Exemplary alkylsulfinyl groups include methylsulfinyl, ethylsulfinyl, butylsulfinyl, and hexylsulfinyl.

8. Control

The terms "control" or "control levels" or "control cells" are defined as the standard by which a change is measured, for example, the controls are not subjected to the experiment, but are instead subjected to a defined set of parameters, or the controls are based on pre- or post-treatment levels. They can either be run in parallel with or before or after a test run, or they can be a pre-determined standard.

9. Higher

The terms "higher," "increases," "elevates," or "elevation" or like terms or variants of these terms, refer to increases above basal levels, e.g., as compared a control. The terms "low," "lower," "reduces," "decreases" or "reduction" or variation of these terms, refer to decreases below basal levels, e.g., as compared. to a control. For example, basal levels are normal in vivo levels prior to, or in the absence of, or addition of an agent such as an agonist or antagonist to activity. For example, decreases or increases can be used to describe the binding of a molecule to a receptor. In this context, decreasers would describe a situation of where the binding could be defined as having a Kd of $10^{-9}$ M, if this interaction decreased, meaning the binding lessened, the Kd could decrease to $10^{-6}$ M. It is understood that wherever one of these words is used it is also disclosed that it could be 1%, 5%, 10%, 20%, 50%, 100%, 500%, or 1000% increased or decreased from a control.

10. Inhibit

By "inhibit" or other forms of inhibit means to hinder or restrain a particular characteristic. It is understood that this is typically in relation to some standard or expected value, in other words it is relative, but that it is not always necessary for the standard or relative value to be referred to. For example, "inhibits phosphorylation" means hindering or restraining the amount of phosphorylation that takes place relative to a standard or a control.

11. Maintaining

The word "maintaining" or like words refers to continuing a state. In the context of a treatment, maintaining can be refer to less than 20%, 15%, 10%, 9%, 8%, 7%, 6%, 5%, 4%, 3%, 2%, 1%, or 0.1% change from a control, such a basal level, often a level in the absence of a treatment or in the presence of treatment with a placebo or standard.

12. Material

Material is the tangible part of something (chemical, biochemical, biological, or mixed) that goes into the makeup of a physical object.

13. Modulate

The term modulate or like terms refers to its standard meaning of increasing or decreasing.

14. Substance

A substance or like terms is any physical object. A material is a substance. Molecules, ligands, markers, cells, proteins, and DNA can be considered substances. A machine or an article would be considered to be made of substances, rather than considered a substance themselves.

15. Molecule

As used herein, the terms "molecule" or like terms refers to a biological or biochemical or chemical entity that exists in the form of a chemical molecule or molecule with a definite molecular weight. A molecule or like terms is a chemical, biochemical or biological molecule, regardless of its size.

Many molecules are of the type referred to as organic molecules (molecules containing carbon atoms, among others, connected by covalent bonds), although some molecules do not contain carbon (including simple molecular gases such as molecular oxygen and more complex molecules such as some sulfur-based polymers). The general term "molecule" includes numerous descriptive classes or groups of molecules, such as proteins, nucleic acids, carbohydrates, steroids, organic pharmaceuticals, small molecule, receptors, antibodies, and lipids. When appropriate, one or more of these more descriptive terms (many of which, such as "protein," themselves describe overlapping groups of molecules) will be used herein because of application of the method to a subgroup of molecules, without detracting from the intent to have such molecules be representative of both the general class "molecules" and the named subclass, such as proteins. Unless specifically indicated, the word "molecule" would include the specific molecule and salts thereof, such as pharmaceutically acceptable salts.

16. Optionally

"Optional" or "optionally" means that the subsequently described event or circumstance may or may not occur, and that the description includes instances where said event or circumstance occurs and instances where it does not.

17. Prevent

By "prevent" or other forms of prevent means to stop a particular characteristic or condition. Prevent does not require comparison to a control as it is typically more absolute than, for example, reduce or inhibit. As used herein, something could be reduced but not inhibited or prevented, but something that is reduced could also be inhibited or prevented. Similarly, something could be reduced and inhibited, but not prevented. It is understood that where reduce, inhibit or prevent are used, unless specifically indicated otherwise, the use of the other two words is also expressly disclosed. Thus, if inhibits phosphorylation is disclosed, then reduces and prevents phosphorylation are also disclosed.

18. Ranges

Ranges can be expressed herein as from "about" one particular value, and/or to "about" another particular value. When such a range is expressed, some forms includes from the one particular value and/or to the other particular value. Similarly, when values are expressed as approximations, by use of the antecedent "about," it will be understood that the particular value forms some forms. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to" the value, "greater than or equal to the value" and possible ranges between values are also disclosed, as appropriately understood by the skilled artisan. For example, if the value "10" is disclosed the "less than or equal to 10" as well as "greater than or equal to 10" is also disclosed. It is also understood that the throughout the application, data are provided in a number of different formats, and that this data, represents endpoints and starting points, and ranges for any combination of the data points. For example, if a particular datum point "10" and a particular datum point 15 are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

19. Reduce

By "reduce" or other forms of reduce means lowering of an event or characteristic. It is understood that this is typically in relation to some standard or expected value, in other words it is relative, but that it is not always necessary for the standard or relative value to be referred to. For example, "reduces phosphorylation" means lowering the amount of phosphorylation that takes place relative to a standard or a control.

20. References

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon.

21. Specifically Interacts

Specifically interacts or like terms means that the interaction is beyond a background interaction. The background interaction can be determined by for example looking at the interaction with serum albumin.

22. Subject

As used throughout, by a "subject" is meant an individual. Thus, the "subject" can include, for example, domesticated animals, such as cats, dogs, etc., livestock (e.g., cattle, horses, pigs, sheep, goats, etc.), laboratory animals (e.g., mouse, rabbit, rat, guinea pig, etc.) mammals, non-human mammals, primates, non-human primates, rodents, birds, reptiles, amphibians, fish, and any other animal. The subject can be a mammal such as a primate or a human. The subject can also be a non-human.

23. Tissue

Tissue or like terms refers to a collection of cells. Typically a tissue is obtained from a subject.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary and are not intended to limit the disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

A. Materials and General Procedures.

Most reagent and chemicals were purchased from Sigma, Fluka or Aldrich. The THF, dichloromethane and acetonitrile solvents were distilled under argon. Before reaction, the solid starting materials were dried under high vacuum. All the reactions were performed under argon. Solvent mixtures are indicated as volume/volume ratios. Thin layer chromatography (TLC) was run on analytical Merck 60 $F_{254}$ plates (0.25 mm thick; $R_f$ values in the text are for the title products) and visualized under UV-light. Flash column chromatography was performed using Fluka silica gel 60 (mesh size 0.040-0.063 mm) using a silica gel: crude compound weight ratio of ca. 30:1. $^1$H, and $^{13}$C spectra were performed using Bruker-400 (400 MHz). Chemical shifts were in ppm relative to tetramethylsilane and coupling constants are in Hz. The phosphoramidite used in solid-phase synthesis was from Glen Research. Anhydrous and air-sensitive solvents and reagents were used and stored in between uses in a Vacuum Atmospheres Company (VAC) M040-2 glove box that was pressurized with nitrogen boil-off gas from a liquid nitrogen tank or in a VAC CS-40 glove box freezer at −20° C. Solvents were dried and redistilled using standard methods. Distilled solvents and reagents were transferred under nitrogen gas to the glove box immediately after distillation using an evacuated Schlenk tube or flask containing activated molecular sieves. All starting materials for anhydrous reactions were dried prior to use on a vacuum line (1-4×10$^{-4}$ torr). Reactions were monitored with glass-backed TLC plates pre-coated with silica gel 60 $F_{254}$ (EMD Chemicals). Flash column chromatography was carried out using Fluka silica gel (60 Å pore, 230-400 mesh) that was packed in glass columns and pressurized with nitrogen. NMR Spectra were recorded on a Varian Unity +300 or Brucker Avance 400 spectrometer, using either CDCl$_3$ or DMSO-d$_6$ as solvents. Chemical shifts for $^1$H NMR were referenced relative to tetramethylsilane (0.00 ppm), CDCl$_3$ (7.24 ppm) or DMSO (2.50 ppm). Chemical shifts for $^{13}$C NMR were referenced relative to CDCl$_3$ (77.23 ppm) or DMSO (39.50 ppm). $^{13}$C NMR signals were assigned using $^{13}$C-APT technique. High resolution (HR) MS were either obtained with electrospray ionization (ESI) on a Q-TOFTM Waters Micromass at Georgia State University.

B. Preparation of Compounds of Formula (I)

The following are examples of preparation of compounds of formula (I), or derivatives of the compound of formula (I). These examples are intended to be purely exemplary and are not intended to limit the disclosure.

1. Example No. 1

Figure 3B:
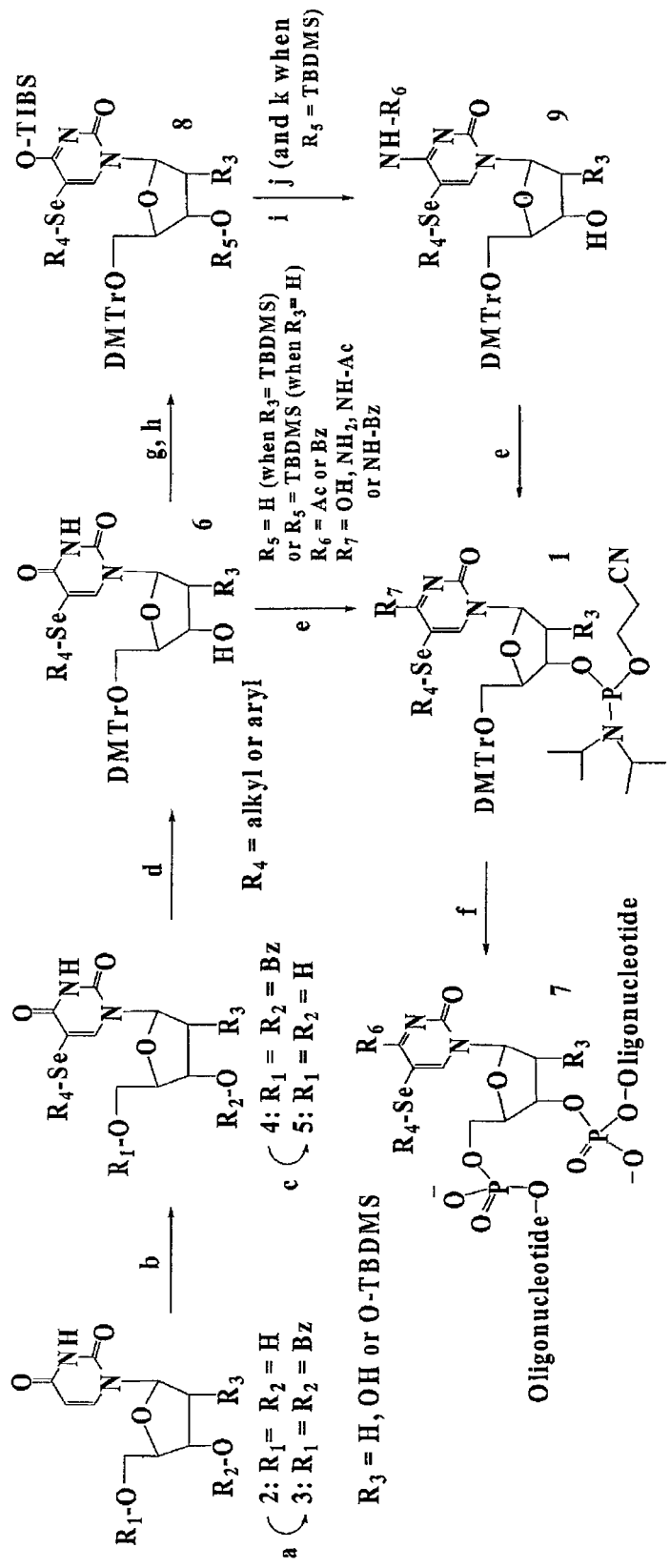
FIG. 3B. A representation of the synthesis of 5-Se-T phosphoramidite (1) and oligonucleotides (7) containing 5-Se-T according to one embodiment of the disclosure.

5-Se-T phosphoramidite (1) and oligonucleotides (7) containing 5-Se-T were synthesized using the method of synthesis shown in FIGS. 3A and 3B. Conditions and reagents for steps of a-f in this synthesis are: (a) Bz-Cl, Py, 0° C., 1 h, 95%; (b) RSe-SeR (CH$_3$SeSeCH$_3$ for the 5-Se-thymidine synthesis), Mn(OAc)$_3$, AcOH, 90° C., 36 h, 56%; (c) NaOCH$_3$, MeOH, 2 h, 93%; (d) DMTr-Cl, Py; 3 h, 82%; (e) i-Pr$_2$NP (Cl)CH$_2$CH$_2$CN, s-benzylthiotetrazole, DIEA, CH$_2$Cl$_2$, 81%; f) solid phase synthesis.

2. Example No. 2

Synthesis of the 5-Se-T Nucleoside, Phosphoramidite and Modified DNAs

Figure 3C:
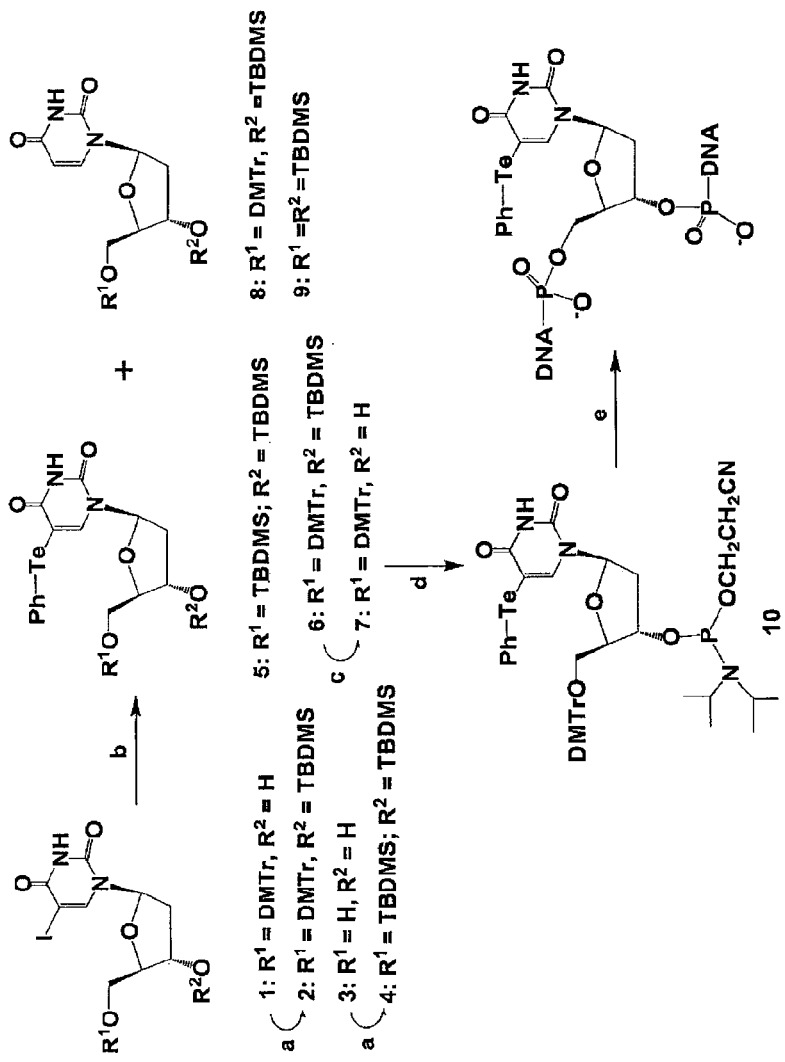
FIG. 3C; A representation of the synthesis of 5-phenyltelluro-2'-deoxyuridine, its phosphoramidite, and the Te-DNAs.
Figure 25:
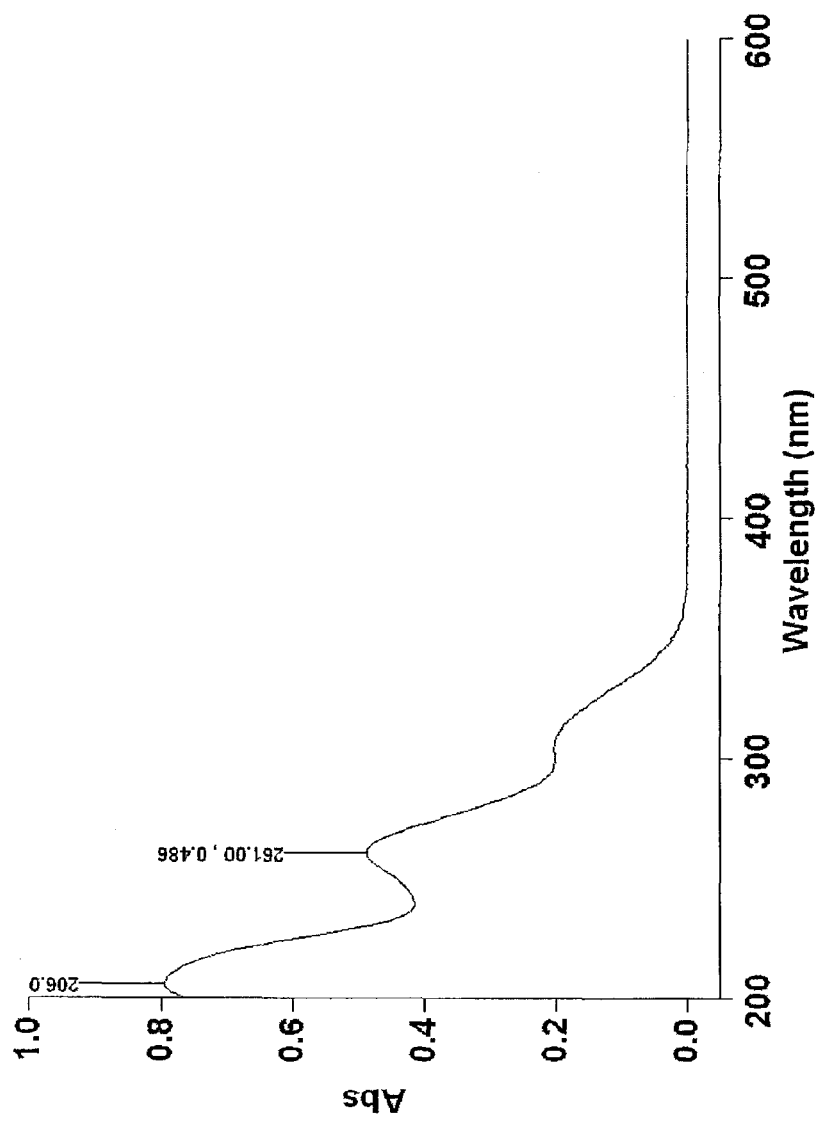
FIG. 25. UV spectrum of 5-seleno-thymidine according to an embodiment of the disclosure.

As shown in FIG. 3, synthesis of the 5-Se-thymidine phosphoramidite (1) started from 2'-deoxyuridine (2), which was protected via benzoylation to give (3), followed by the methylselenylation. Though the arylselenylation at the 5-position of pyrimidines was reported over a decade ago [Lee, C. H. & Kim, Y. H. (1991) *Tetrahedron Letters* 32, 2401-2404], the incorporation of alkylselenyl substitutions (such as CH$_3$—Se) at the 5-position of pyrimidines remained as a challenge. As shown in FIG. 3B, a new electrophilic addition and elimination strategy was developed to incorporate a methylselenyl group at the 5-position of 2'-deoxyuridine by using a very weak oxidant dimethyldiselenide [(CH$_3$Se)$_2$] in the presence of an electrophilic activator (FIG. 3B). This methylselenylation was achieved by treatment of (3) with (CH$_3$Se)$_2$ in the presence of Mn(OAc)$_3$ (an electrophile activator) under an elevated temperature, to give 5-Se-thymidine derivative (4). Deprotection of (4) with NaOCH$_3$ in MeOH gave (5) in a quantitative yield. As shown in FIG. 25, UV spectrum of (5) shows $\lambda_{max}$ absorption at 309 nm, red-shifted by 44 nm when compared with thymidine. This large red-shift is caused by the electron-donating effect of 5-SeCH$_3$ on the nucleobase π-system. Following tritylation of (5), phosphitylation of (6) under standard conditions [Salon, J., Sheng, J., Jiang, J., Chen, G., Caton-Williams, J. & Huang, Z. (2007) *J Am Chem Soc* 129, 4862-3] gave the phosphoramidite (1) in high yield.

Figure 4:
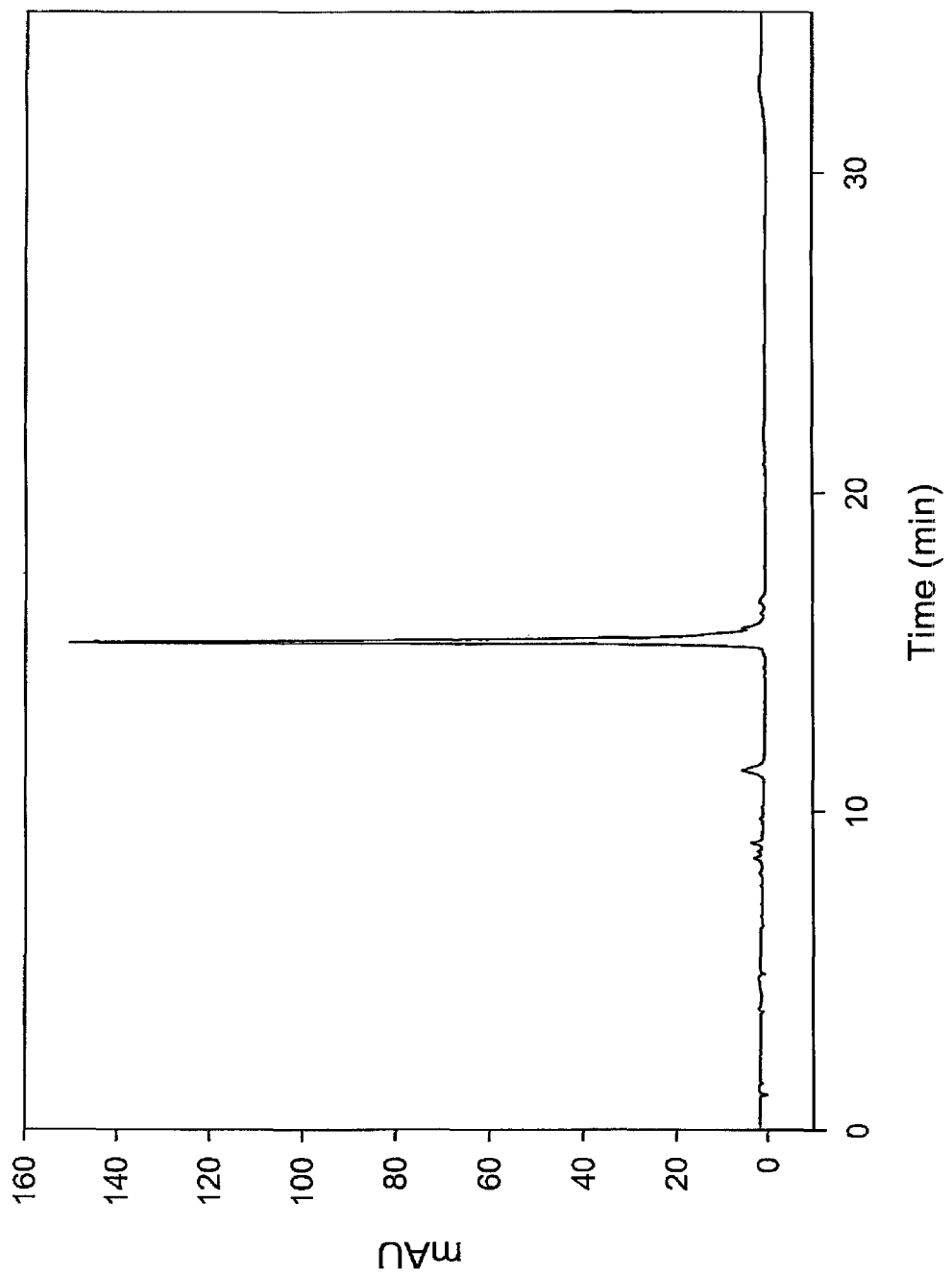
FIG. 4. HPLC analysis of the corresponding Se-modified, 5'-DMTr-T-T$^{5-Se}$T-T-3' according to one embodiment of the disclosure.

5-Se-thymidine (5-Se-T) phosphoraraidite (1) was found compatible with the conditions of the solid-phase synthesis, including the coupling reaction, acetylation capping, I$_2$ oxidation, trichloroacetic acid and concentrated ammonia treatments. The stability of the 5-Se-T moiety allows to successfully synthesize the Se-oligonucleotides using the normal phosphoramidites. A typical HPLC profile of the synthesized crude Se-DNAs is shown in FIG. 4. The HPLC analysis was performed on a Zorbax SB-C18 column (4.6×250), eluted (1 mL/min) with a linear gradient from buffer A (20 mM triethylammonium acetate, pH 7.1) to 100% buffer B (50% acetonitrile, 20 mM triethylammonium acetate, pH 7.1) in 30 min.

Figure 5:
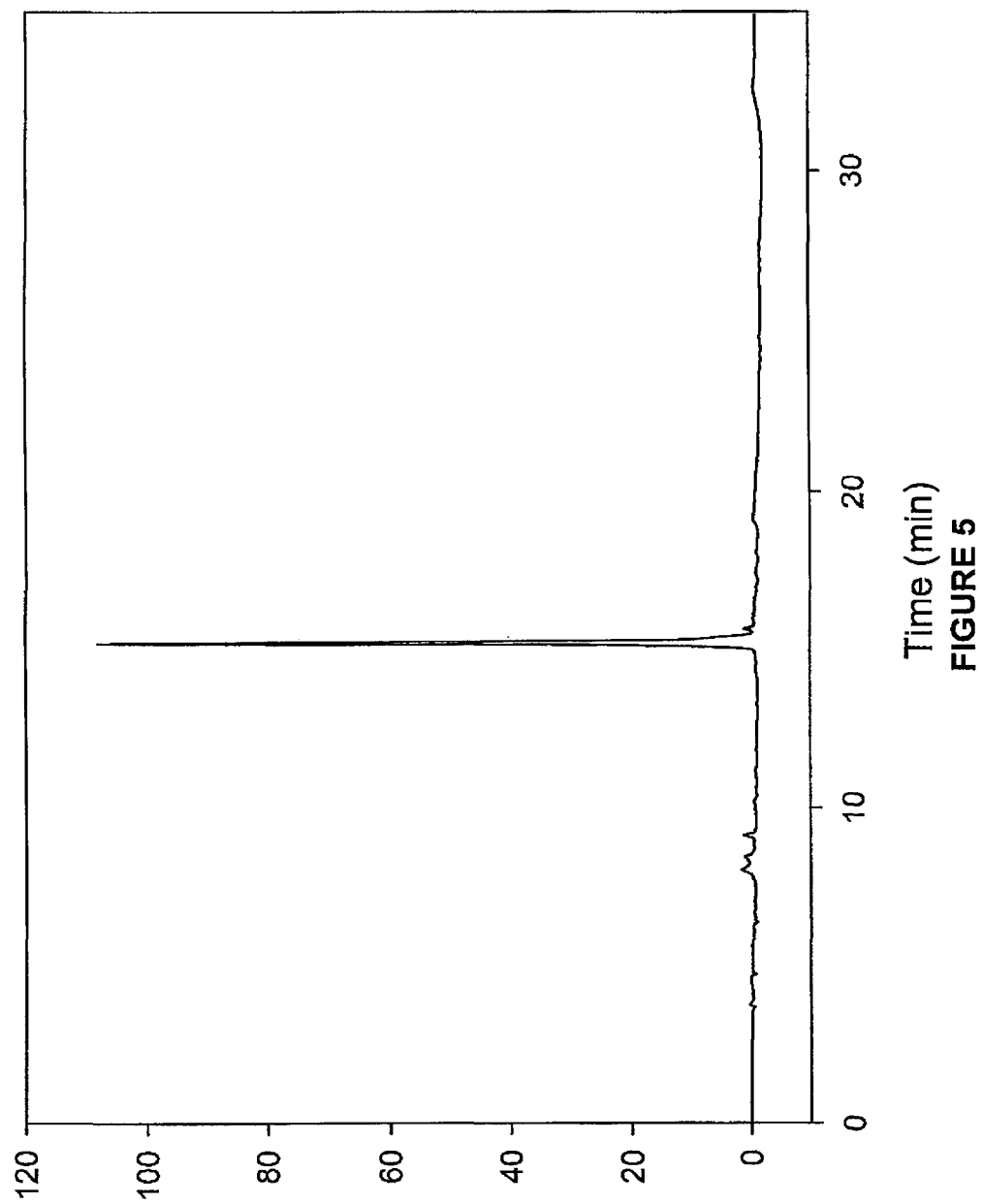
FIG. 5. HPLC analysis of the synthesized crude 5'-DMTr-TTTT-3' according to one embodiment of the disclosure.
Figure 6:
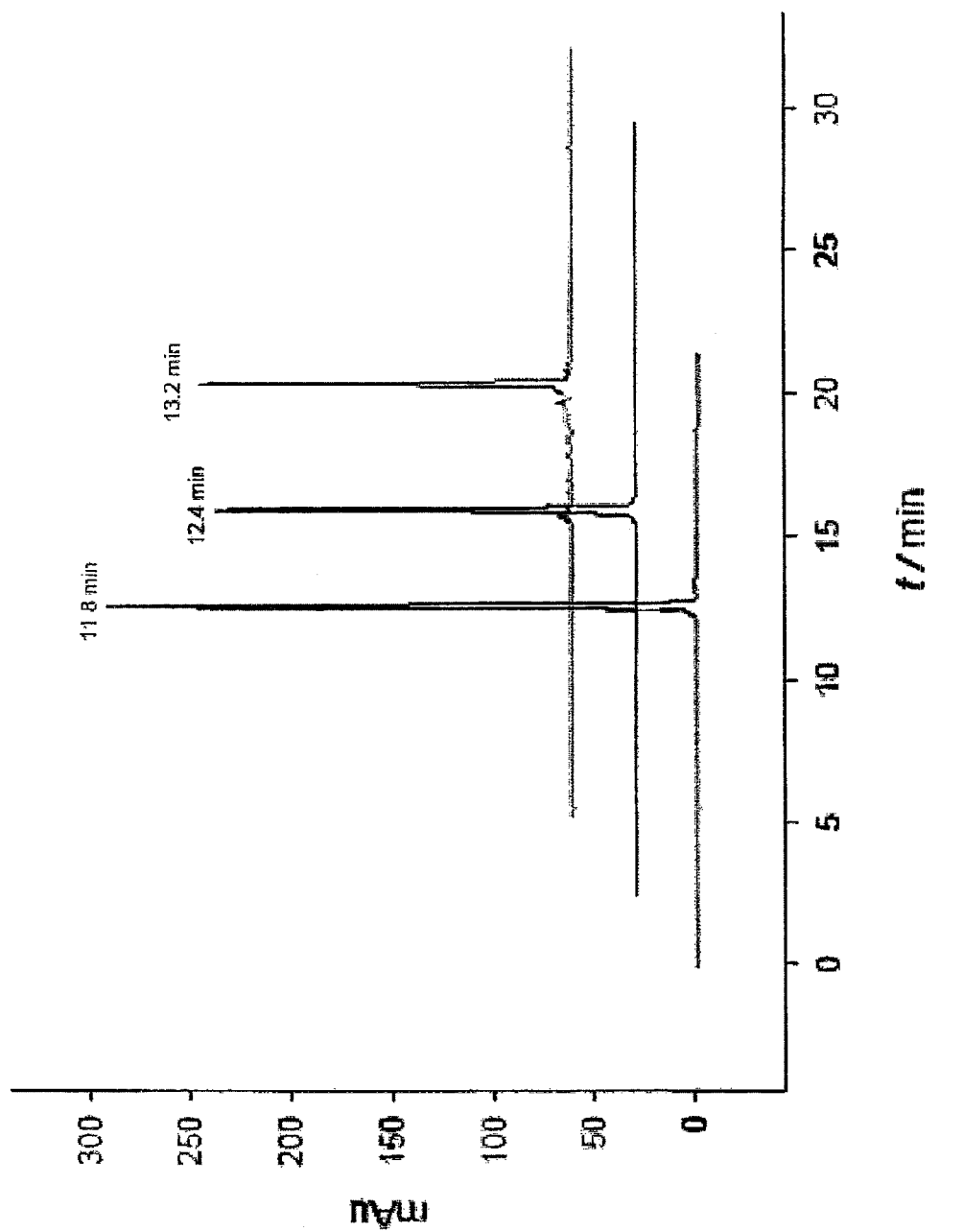
FIG. 6: HPLC analysis of the native and modified DNAs (DNAs modified according to forms of the disclosure).
Figure 7:
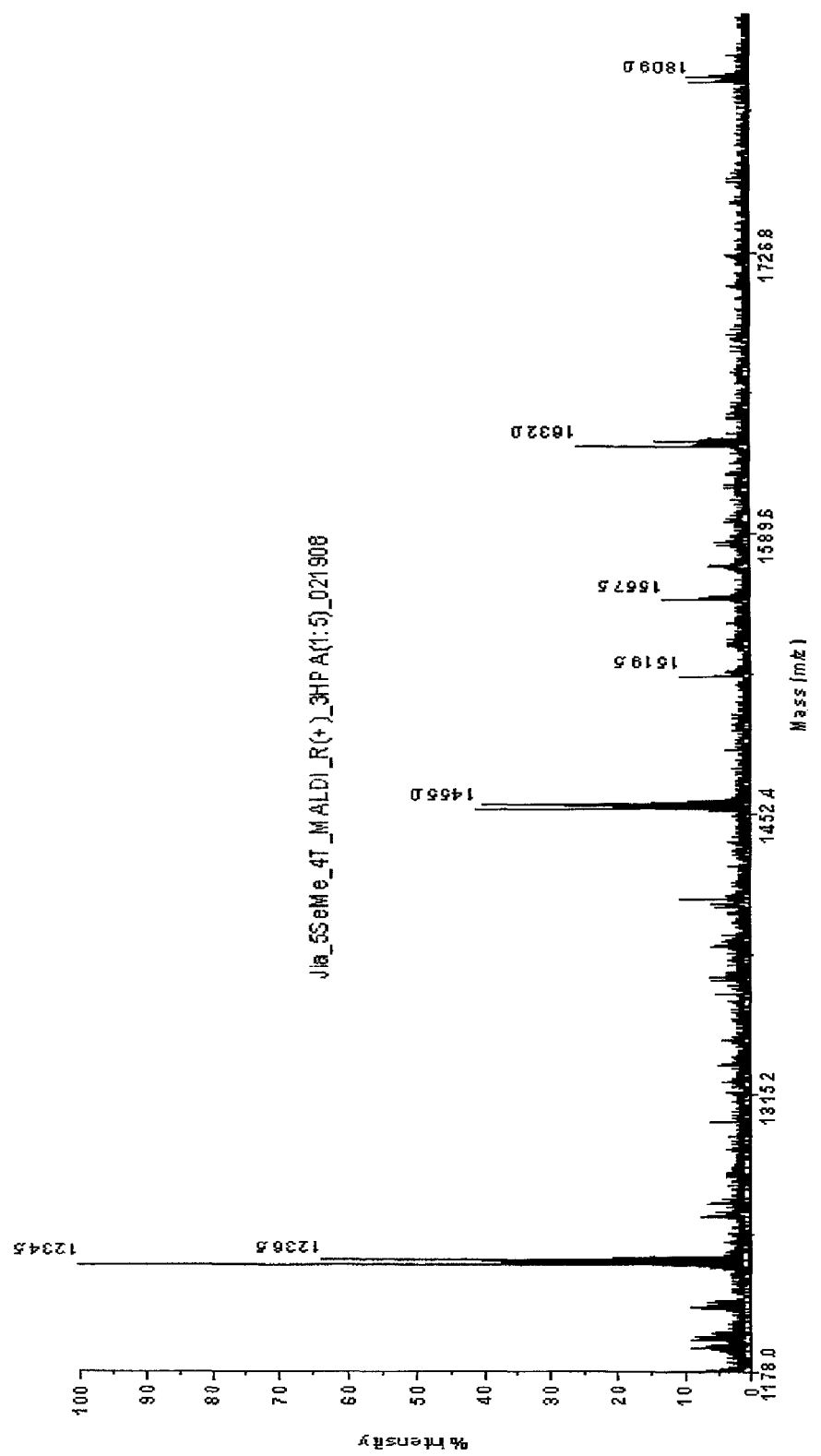
FIG. 7. MALDI-MS analysis of 5'-TT$^{5-Se}$TT-3': Molecular Formula, $C_{40}H_{53}N_8O_{26}P_3Se$; [M]$^+$: 1234.5 (calc. 1234.1) according to one embodiment of the disclosure.
Figure 8:
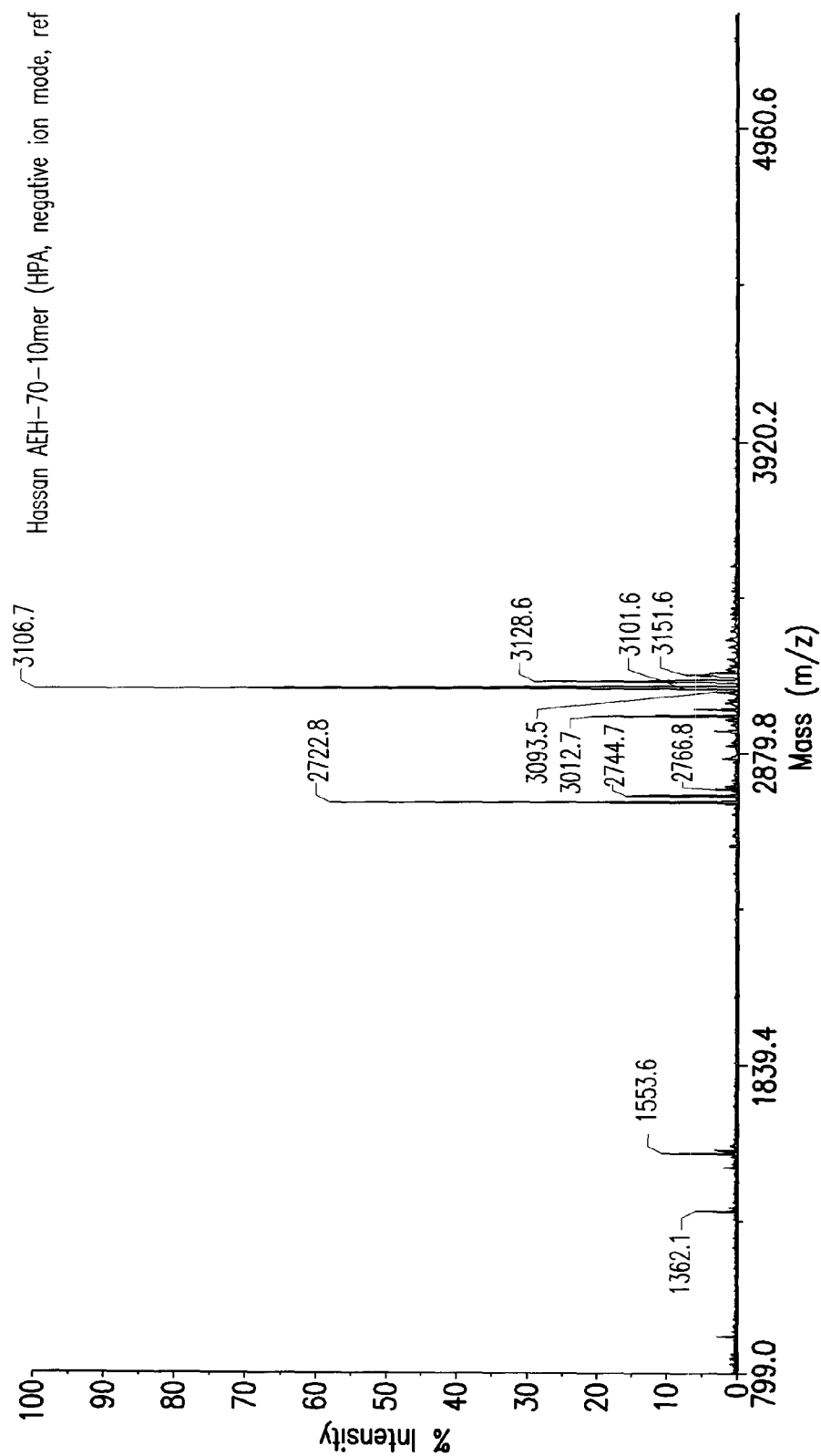
FIG. 8. MALDI-MS spectrum of 5'-GCG-$^{5-Se}$T-ATACGC-3': Molecular formula: $C_{97}H_{123}N_{38}O_{58}P_9Se$; [M–H$^+$]$^-$: 3106.7 (calc. 3105.5) according to one embodiment of the disclosure.
Figure 9:
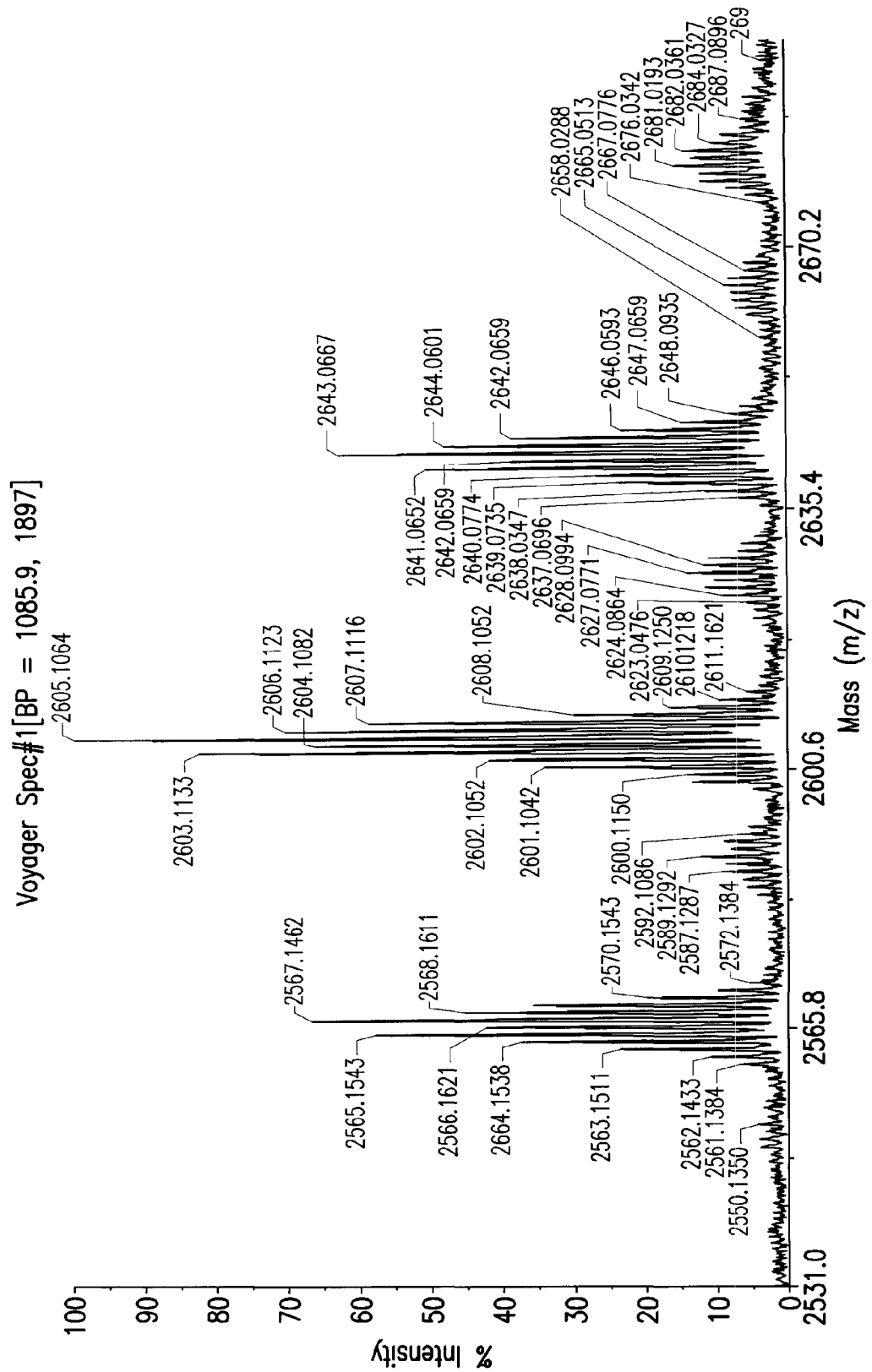
FIG. 9. MALDI-MS spectrum analysis of the double modified 5'-G-dU$_{2'-Se}$-G-$^{5-Se}$T-ACAC-3': Molecular Formula: $C_{78}H_{99}N_{30}O_{46}P_7Se_2$; [M+K$^+$-2H$^+$]$^-$: 2605.1 (calc. 2605.2) according to one embodiment of the disclosure.
Figure 10:
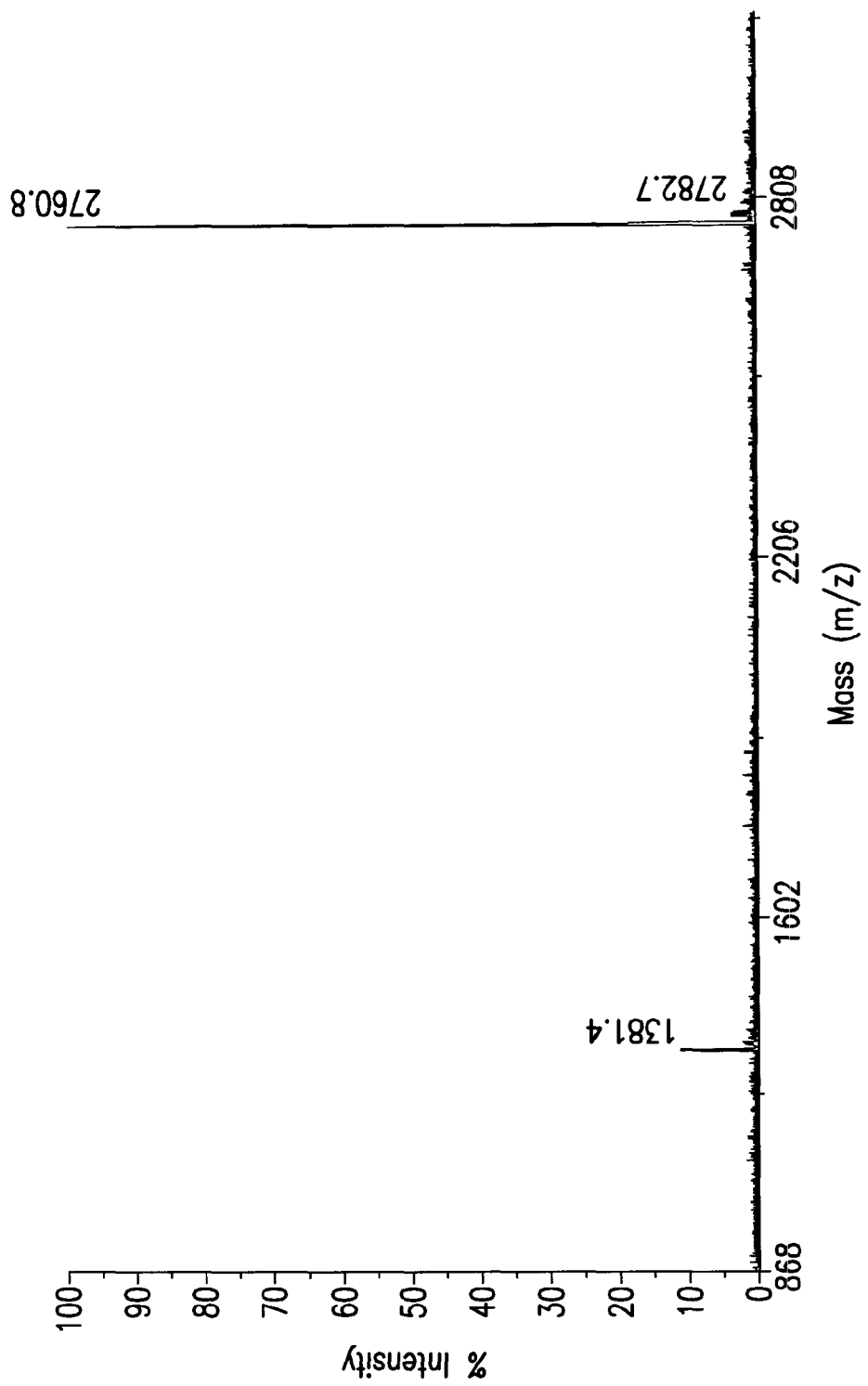
FIG. 10. MS analysis of a modified DNA modified according to one embodiment of the disclosure. MALDI-MS of 5'-ATGG$^{5-S}$TGCTC-3', isotopic mass: 2761.9, measured (calc.) m/z: [M–H$^+$]$^-$: 2760.8 (2760.8); [M–2H$^+$]$^-$: 1381.4 (1379.9); [M+Na$^+$-2H$^+$]$^-$: 2782.7 (2782.8).
Figure 11:
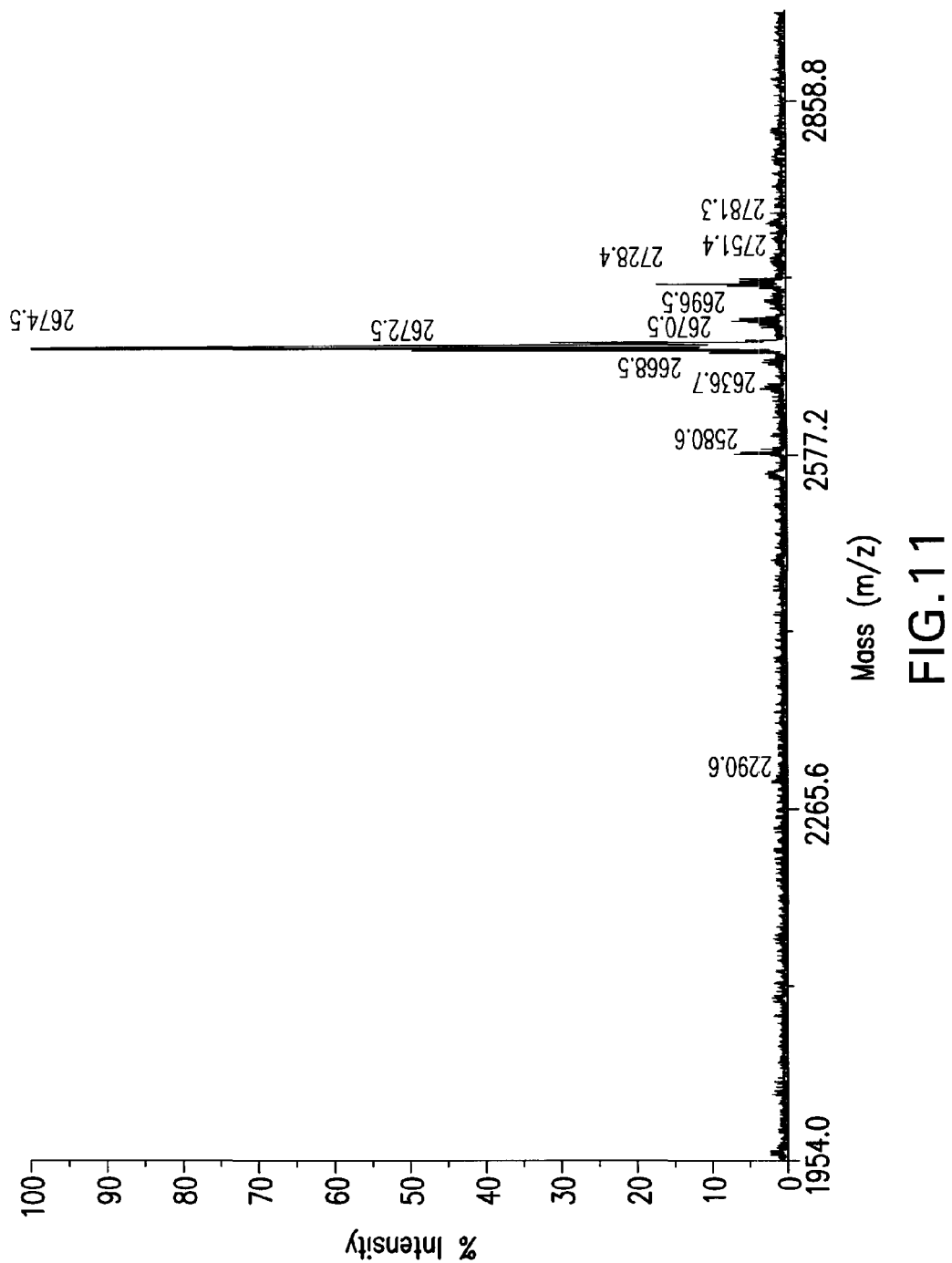
FIG. 11. MS analysis of a modified DNA modified according to one embodiment of the disclosure. MALDI-MS of 5'-CTCCCA$^{5-Se}$TCC-3', isotopic mass: 2673.5, measured (calc.) [M+H$^+$]$^+$: 2674.5 (2674.5); [M+Na$^+$]$^+$: 2696.5 (2696.5).

FIG. 4 shows the HPLC analysis of crude 5'-DMTr-TT-$^{5-Se}$T-T-3' (15.3 min). This analysis is which is virtually identical to that of the corresponding native DNA as shown in FIG. 5 shows the HPLC analysis of crude 5'-DMTr-TTT-T-3'. FIG. 6 shows an HPLC analysis of the native and modified DNAs. The blue profile: the native DNA (5'-CTTCTTGTCCG-3', retention time=11.8 min); the red profile: the S-modified DNA (5'-CTTCT$^{5-S}$TGTCCG-3', retention time=12.4 min); the green profile: the Se-modified DNA (5'-CTTCT$^{5-Se}$TGTCCG-3', retention time=13.2 min). A linear gradient was run from Buffer B 0% to 35% in 15 minutes. It was determined that the coupling yield of the 5-Se-T phosphoramidite was over 99%. The synthesized Se-DNAs were purified and analyzed by HPLC, MS and UV melting studies. The results are shown in Table 1 and FIGS. 7-12.

TABLE 1

MS & $T_m$ values of the 5-Se-T-containing DNA duplexes

| entry | FIG. | oligonucleotide | MALDI-MS measured (calcd.) m/z | $T_m$ (° C.) native/Se |
|---|---|---|---|---|
| 1 | 7 | TT-$^{5-Se}$T-T | [M]$^+$: 1234.5 (1234.1) | |
| 2 | | GTGTACAC$^a$ | | 27.5 (native) |

TABLE 1-continued

MS & $T_m$ values of the 5-Se-T-containing DNA duplexes

| entry | FIG. | oligonucleotide | MALDI-MS measured (calcd.) m/z | $T_m$ (° C.) native/Se |
|---|---|---|---|---|
| 3 | | G-$^{5\text{-}Se}$T-GTACAC$^a$ | [M – H$^+$]: 2487.4 (2487.4) | 27.9 (Se) |
| 4 | | GCGTATACGC$^a$ | | 28.0 (native) |
| 5 | 8 | GCG-$^{5\text{-}Se}$T-ATACGC$^a$ | [M – H$^+$]: 3106.7 (3105.5) | 26.5 (Se) |
| 6 | 10 | 5'-ATGG<u>T</u>GCTC<br>3'-TACCACGAG | [M – H$^+$]$^-$: 2808 (2808.4) | 40.3/39.3 |
| 7 | 11 | 5'-CT CCC A<u>T</u>CC<br>3'-GAGGGTAGG | [M + H$^+$]$^+$: 2674.5 (2674.4) | 36.5/36.3 |
| 8 | | 5'-CTT CT<u>T</u> GTCCG<br>3'-GAAGAACAGGC | [M + H$^+$]$^+$: 3352.4 (3352.6) | 44.9/43.9 |
| 9 | 9 | GdU$_2$,-$_{Se}$G-$^{5\text{-}Se}$T-ACAC | [M + K$^+$ – 2H$^+$]$^-$: 2605.1 (2605.2) | |

$^a$Self-complementary.
The underlined Ts (<u>T</u>) are native or Se-derivatized ($^{5\text{-}Se}$T).
MS spectra of the modified oligonucleotides are presented in the FIGURES indicated in the Table.

3. Example No. 3

Synthesis of the 5-Se-T Nucleoside, Phosphoramidite and DNAs

In the examples provided below, bold parenthetical numbers refer to compounds as shown in FIG. 3B. Conditions and reagents for reaction steps in FIG. 3B are: (a) Bz-Cl, Py, 0° C., 1, h, 95%; (b) CH$_3$SeSeCH$_3$, Mn(OAc)$_3$, AcOH, 90° C., 36 h, 56%; (c) NaOCH$_3$, MeOH, 2 h, 93%; (d) DMTr-Cl, Py; 3 h, 82%; (e) i-Pr$_2$NP(Cl)CH$_2$CH$_2$CN, s-benzylthiotetrazole, DIEA, CH$_2$Cl$_2$, 81%; f) solid phase synthesis; g) when R$_3$ is hydrogen, TBDMS-Cl, Py; h) triisopropylbenzenesulfonyl chloride, diisopropylethyl amine, p-dimethylamino pyridine, acetonitrile; i) conc. ammonium hydroxide; j) benzoyl chloride, pyridine; k) tetrabutylammonium fluoride, acetic acid, THF.

Figure 16:
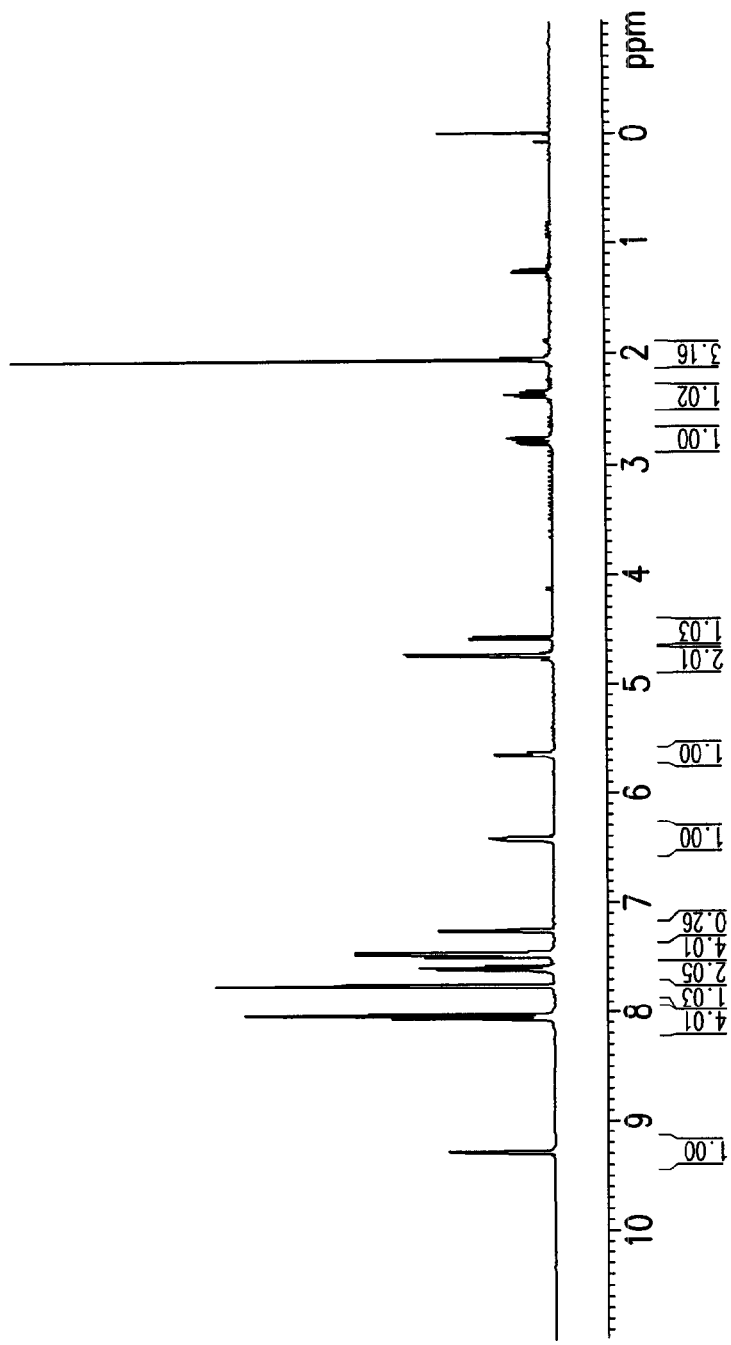
FIG. 16. $^1$H-NMR spectrum of 3',5' Di-O-benzoyl-5-seleno-thymidine according to an embodiment of the disclosure.
Figure 17:
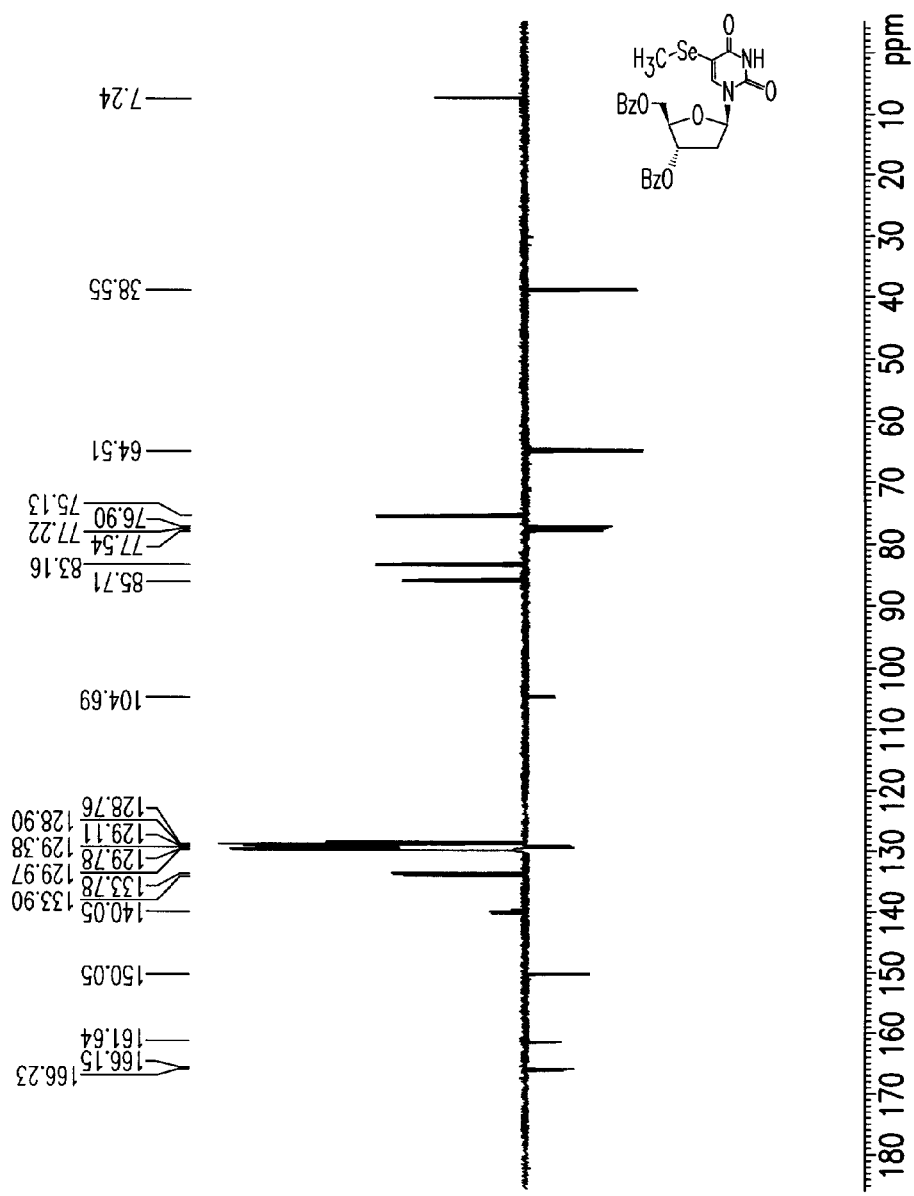
FIG. 17. $^{13}$C-NMR spectrum of 3',5'-Di-O-benzoyl-5-seleno-thymidine according to an embodiment of the disclosure.

3',5'-Di-O-benzoyl-5-seleno-thymidine (4): A mixture of 3',5'-di-O-benzoyl-2'-deoxyuridine (3) (1.89 g, 4.35 mmol), Mn(OAc)$_3$ (3.45 g, 13.0 mmol), and CH$_3$SeSeCH$_3$ (1.23 mL, 13.0 mmol) in glacial AcOH (30 mL) was heated for 36 h at reflux temperature. The mixture was cooled down to room temperature and the insoluble material was filtered off on a Celite pad, washed with EtOAc. The filtrate was evaporated, and co-evaporated with toluene (25 mL×3 times). The residue was purified by flash silica gel chromatography (eluate: 15% EtOAc in CHCl$_3$) to give 4 (1.3 g, 56%) as a white solid, (eluate: 25% EtOAc in CHCl$_3$) to give 3 (0.75 g, 40%) as a white solid. Our NMR analysis showed the disappearance of H-5 peak and appearance of 11-6 singlet peak, and displayed the characteristic $^1$H and $^{13}$C resonance signals of 5-SeCH$_3$ moiety of 4 at 2.06 and 7.24 ppm, respectively. Spectral Data for 4: UV $\lambda_{min}$=307 nm ($\epsilon$=4700 M$^{-1}$cm$^{-1}$ in MeOH), and $\lambda_{max}$ =263 nm ($\epsilon$=9650 M$^{-1}$cm$^{-1}$ in MeOH); $^1$H-NMR (CDCl$_3$) δ: 9.29 (1H, s, NH, exchanged with D$_2$O), 8.11-8.03 (4H, m, Bz), 7.76 (1H, s, H-6), 7.61-7.58 (2H, m, Bz), 7.50-7.45 (4H, m, Bz), 6.42 (1H, dd, H-1', J=5.6, J=8.8 Hz), 5.64 (1H, m, H-3'), 4.78-4.71 (2H, m, H5'a,b), 4.58 (1H, m, H-4'), 2.78 (1H, ddd, H-2'$_a$, J=1.6, J=5.6, J=14.4 Hz), 2.36 (1H, m, H-2'$_b$), 2.06 (3H, s, SeCH$_3$) (FIG. 16); $^{13}$C-NMR (CDCl$_3$) δ: 166.12 (C=O, Bz), 166.15 (C=O, BZ), 161.64 (C4), 150.35 (C2), 140.05 (C-6), 133.90 (Ph, Bz), 133.78 (Ph, Bz), 129.97 (Ph, Bz), 129.78 (Ph, Bz), 129.38 (Ph, Bz), 129.11 (Ph, Bz), 128.90 (Ph, Bz), 128.76 (Ph, Bz), 104.69 (C-5), 85.71 (C4'), 83.16 (C-1'), 75.13 (C-3'), 64.51 (C-5'), 38.55 (C2'), 7.24 (SeCH$_3$) (FIG. 17); HRMS (ESI-TOF): Molecular formula, C$_{24}$H$_{22}$N$_2$O$_7$Se; [M–H$^+$]$^+$: 529.0505 (calc. 529.0514).

Figure 18:
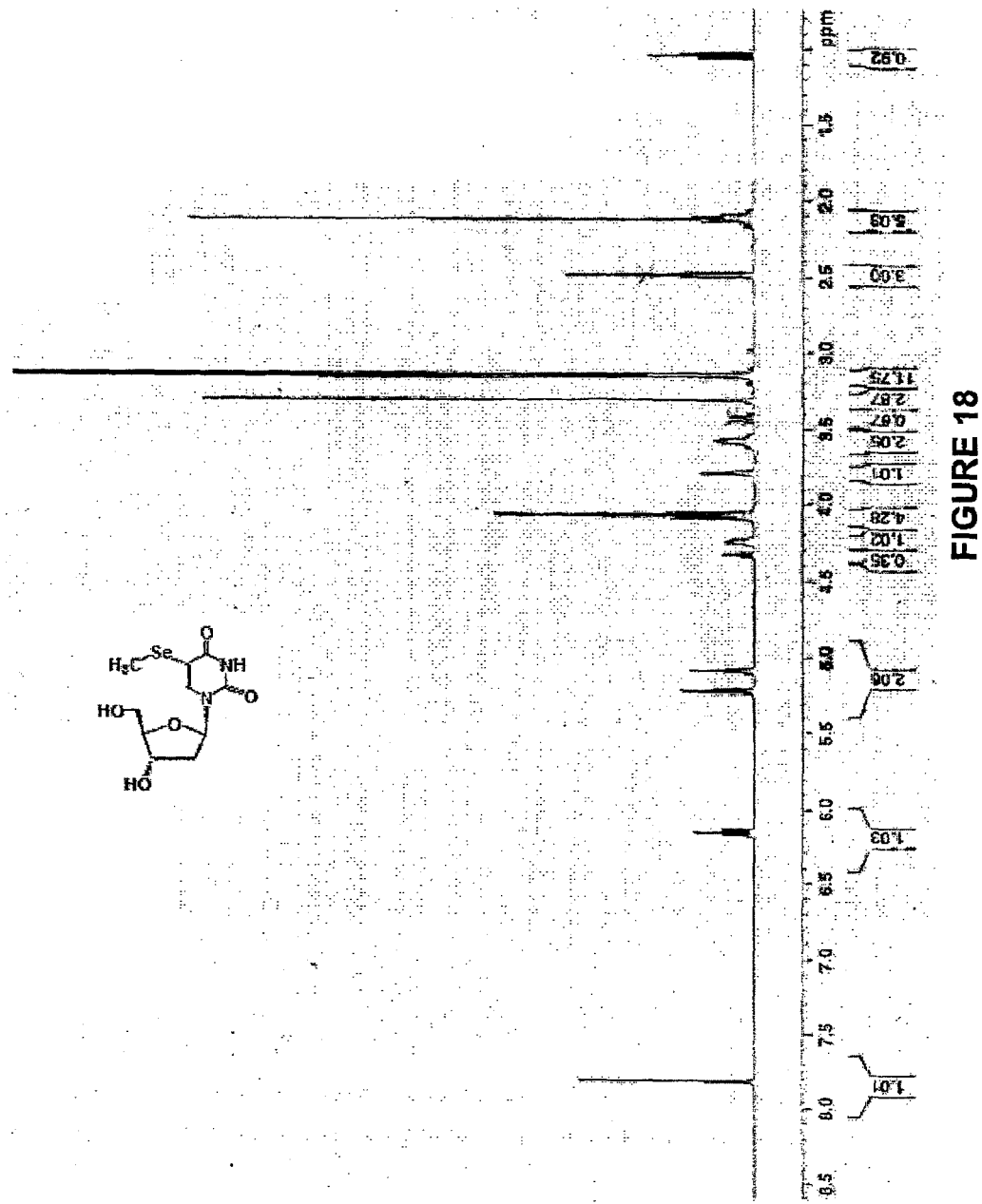
FIG. 18. $^1$H-NMR spectrum of 5-seleno-thymidine according to an embodiment of the disclosure.
Figure 19:
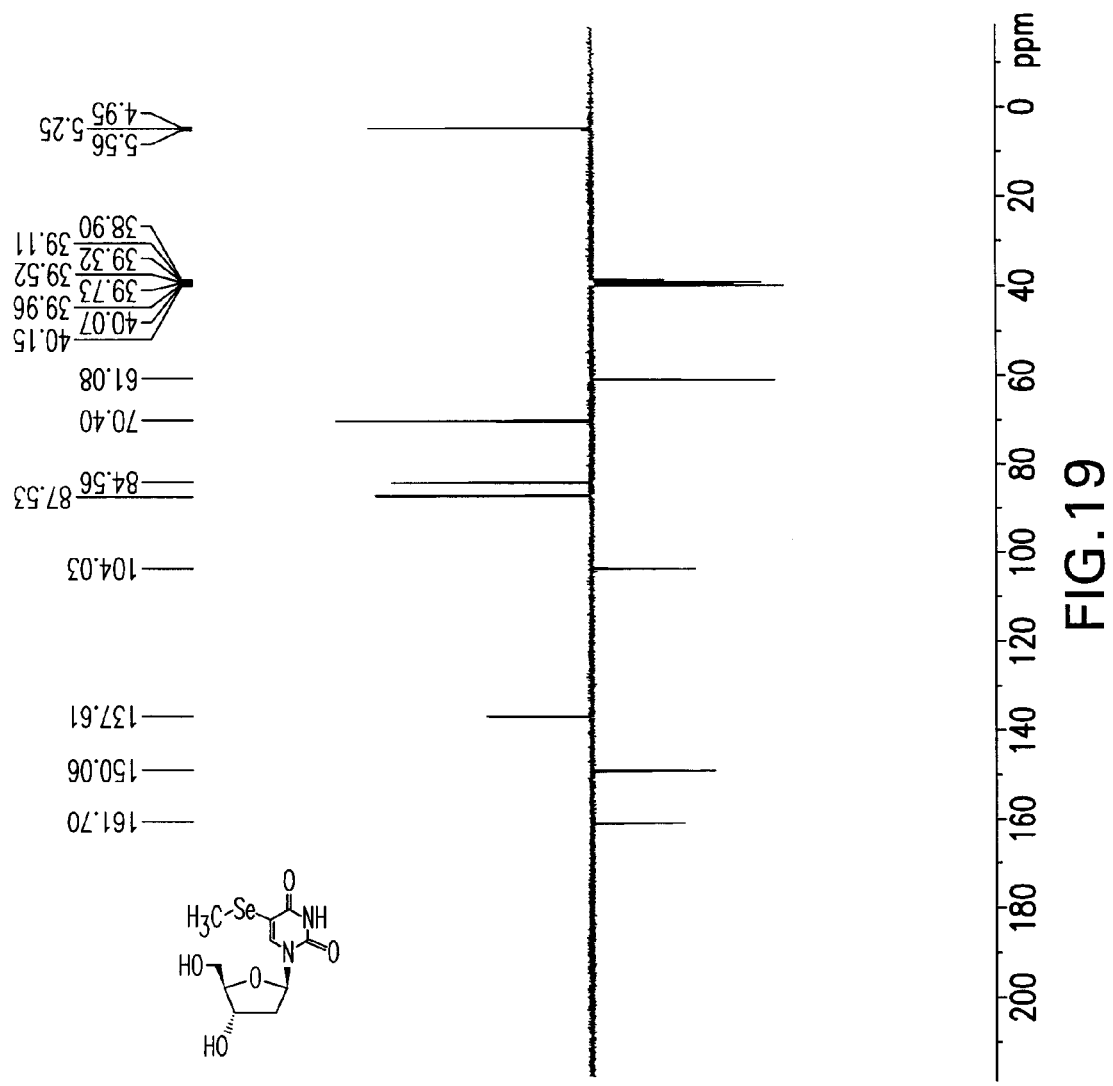
FIG. 19. $^{13}$C-NMR spectrum of 5-seleno-thymidine according to an embodiment of the disclosure.

5-seleno-thymidine (5). To a solution of 4 (0.827 g, 1.56 mmol) in MeOH (10 mL) was added 1M NaOMe in MeOH (1.6 mL). The mixture was stirred for 3 h at room temperature. The mixture was neutralized with Dowex 50 (H$^+$) and the resin was filtered off. The filtrate was evaporated and the residual solid was purified by flash silica gel column (eluate: 7% MeOH in CH$_2$Cl$_2$) to give 0.466 g, 93%) as a white solid, which was crystallized from EtOH: Spectral Data for 5: UV $\lambda_{min}$=309 ($\epsilon$=2000 M$^{-1}$cm$^{-1}$ in MeOH), and $\lambda_{max}$=261 ($\epsilon$=4790 M$^{-1}$cm$^{-1}$ in MeOH); $^1$H-NMR (DMSO-d$_6$) δ: 11.52 (1H, s, NH, exchanged with D$_2$O), 7.83 (1H, s, H-6), 6.18 (1H, t, H-1', J=6.4 Hz), 5.23 (1H, brd, 3'-OH, exchanged with D$_2$O), 5.10 (1H, brt, 5'-OH), 4.26 (1H, m, H-3'), 3.80 (1H, m, H-4'), 3.60 (2H, m, H5'a, H5b) 2.67 (5H, m, H-2'$_a$, H-2'$_b$, and 5-SeCH$_3$) (FIG. 18); $^{13}$C-NMR (CDCl$_3$) δ: 161.70 (C4), 150.06 (C2), 137.61 (C-6), 104.03 (C-5), 87.53 (C4'), 84.56 (C-1'), 70.40 (C-3'), 61.08 (C-5'), 38.90 (C2'), 5.25 (SeCH$_3$) (FIG. 19); HRMS (ESI-TOF): Molecular formula, C$_{10}$H$_{13}$N$_2$O$_5$Se; [M]$^+$: 320.9996 (calc. 320.9990).

Figure 20:
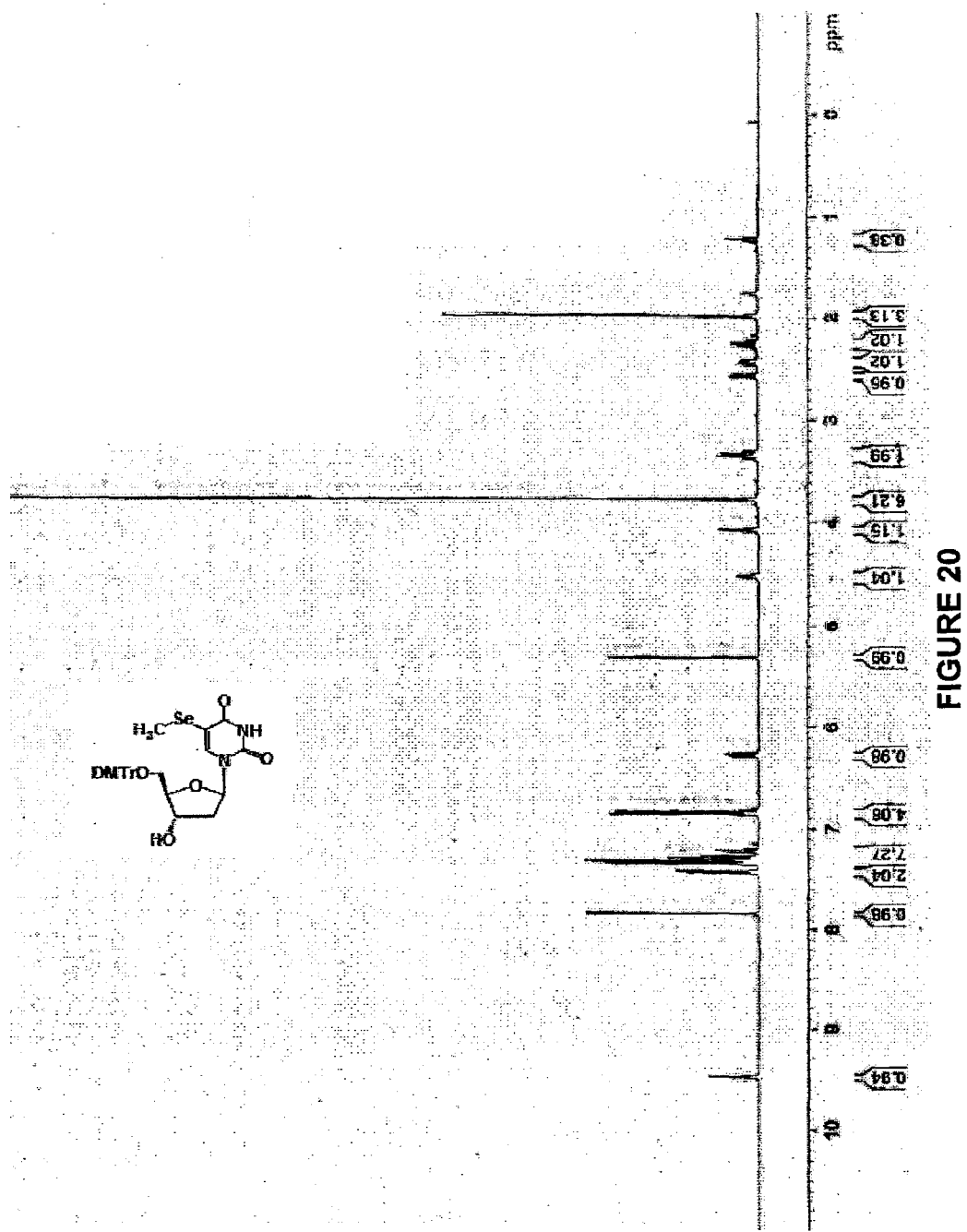
FIG. 20. $^1$H-NMR spectrum of 5'-O-(4,4'-dimethoxytrityl)-5-seleno-thymidine according to an embodiment of the disclosure.
Figure 21:
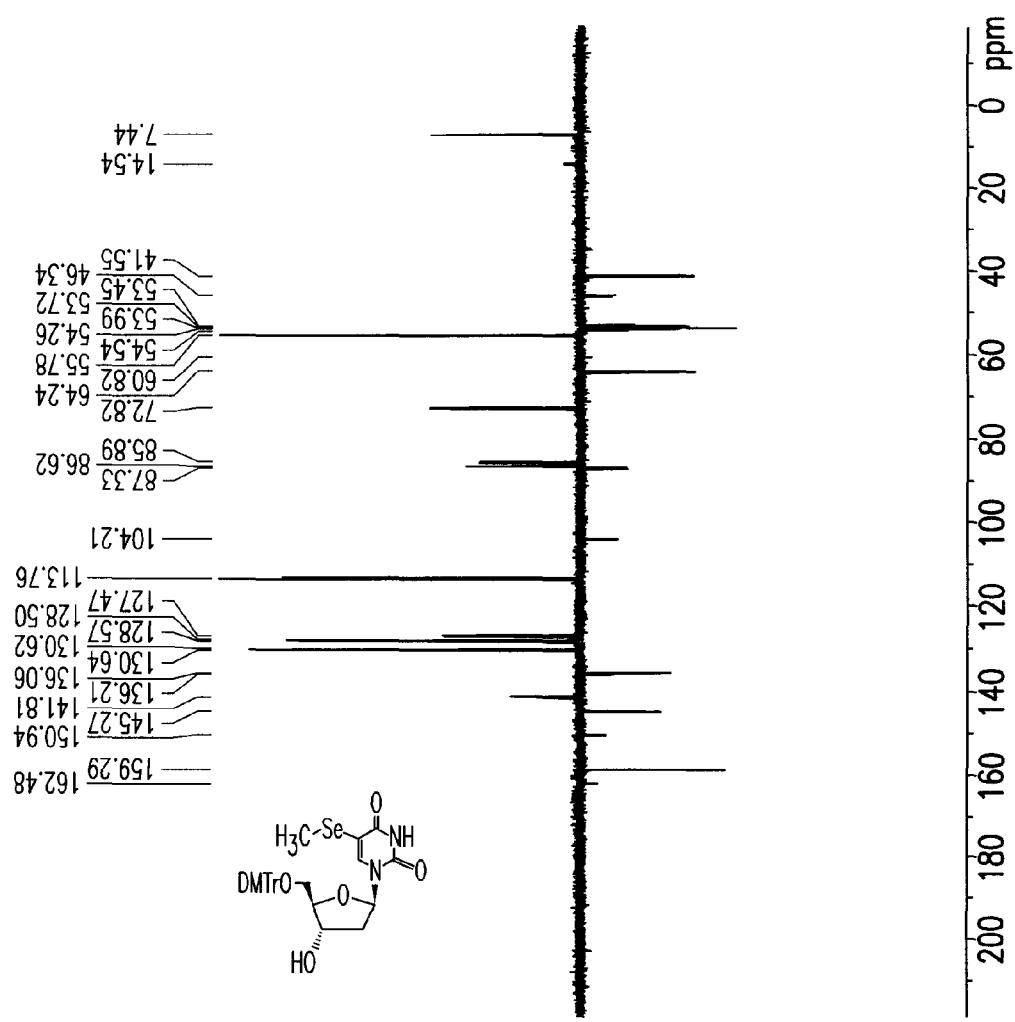
FIG. 21. $^{13}$C-NMR spectrum of 5'-O-(4,4'-dimethoxytrityl)-5-seleno-thymidine according to an embodiment of the disclosure.

5'-O-(4,4'-dimethoxytrityl)-5-seleno-thymidine (6). 2'-deoxy-5-methyl-selenyluridine (5) (0.239 mg, 0.74 mmol) was co-evaporated with dry pyridine (5 mL×3 times). The dried residue was dissolved in dry pyridine (5 mL) and cooled to 0° C. and treated with a solution of 4,4-dimethoxytrityl chloride (0.277 g, 0.82 mmol) in dry pyridine (3 mL). The mixture was stirred for 3 h at room temperature. The solvent was evaporated and the residue was partitioned between EtOAc and H$_2$O. The organic phase was dried over MgSO$_4$ and evaporated. The residue was purified by silica gel column chromatography (the silica gel was pre-equalized with 1% Et$_3$N in CH$_2$Cl$_2$, eluate 4% MeOH in CH$_2$Cl$_2$) to give (380 mg, 82%) of 6 as pale yellow foam: $^1$H-NMR (CD$_2$Cl$_2$) δ: 9.39 (1H, s, NH, exchanged with D$_2$O), 7.90 (1H, s, H-6), 7.46-7.21 (9H, m, DMTr), 6.87-6.84 (4H, m, DMTr), 6.29 (1H, dd, H-1', J=6.4, J=7.6 Hz), 4.43 (1H, m, H-3'), 4.05 (1H, m, H-4'), 3.68 (6H, 2 s, OMe), 3.30 (1H, dd, H5'a, J=3.8, J=10.5 Hz), 3.24 (1H, dd, H5'b, J=3.6, J=10.5 Hz), 2.58 (1H, d, 3'-OH), 2.42 (1H, ddd, H-2'$_a$, J=3.8, J=7.7, J=10.8 Hz), 2.36 (1H, H-2'$_b$), 1.90 (3H, s, SeCH$_3$) (FIG. 20); $^{13}$C-NMR (CD$_2$Cl$_2$) δ: 162.48 (C4), 159.29 (Ar), 150.94 (C2), 145.27 (Ar), 141.81 (C-6), 136.21 (Ar), 136.06 (Ar), 130.64 (Ar), 130.62° (Ar), 128.57 (Ar), 128.50 (Ar), 127.47 (Ar), 113.76 (Ar), 104.21 (C-5), 87.33 (Ar), 86.82 (C4'), 85.89 (C-1'), 72.82 (C-3') 64.24 (C-5'), 41.55 (C2'), 7.44 (SeCH$_3$) (FIG. 21); HRMS (ESI-TOF): Molecular formula, C$_{33}$H$_{32}$N$_2$O$_7$Se; [M+Na$^+$]$^+$: 647.1274 (calc. 647.1272).

Figure 22:
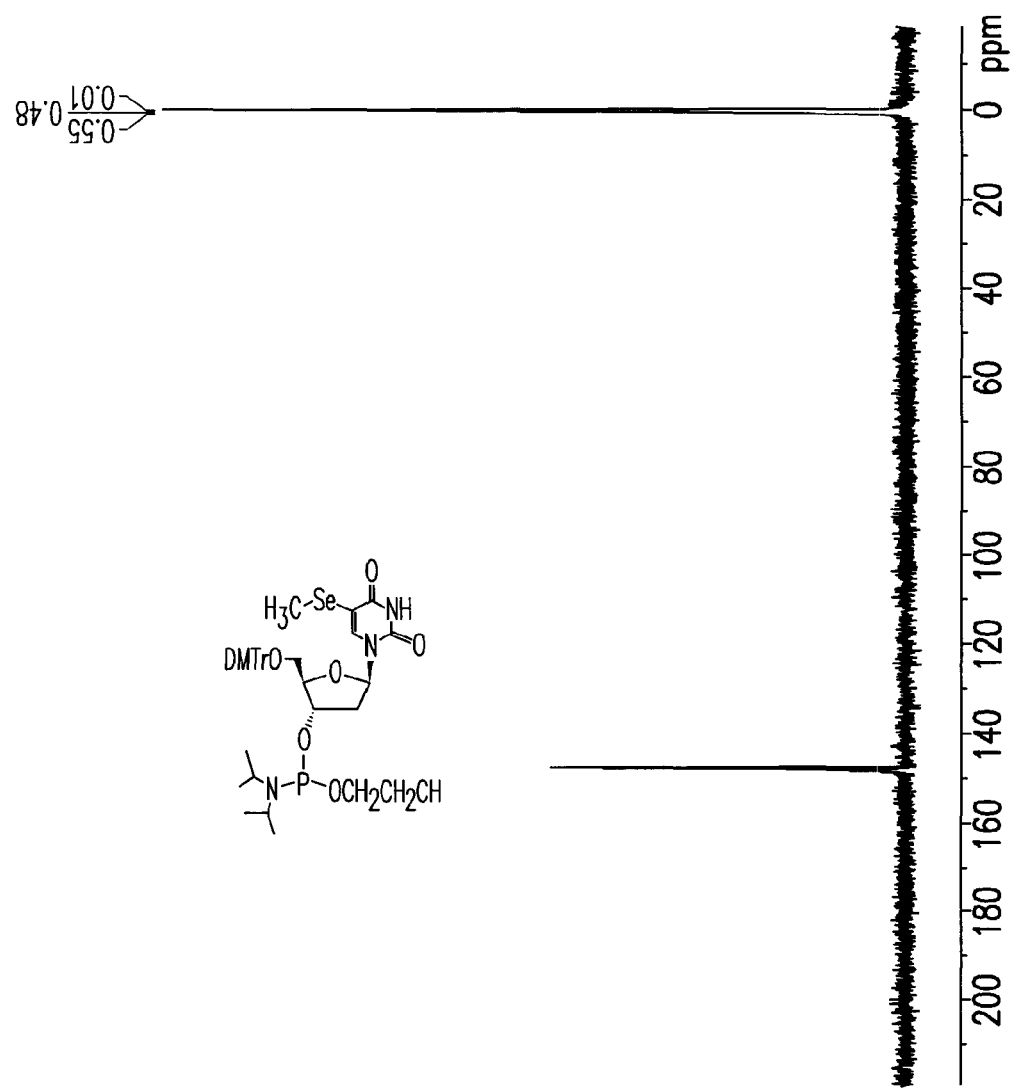
FIG. 22. $^{31}$P-NMR spectrum of 3'-O-(2-cyanoethyl-N,N-diisopropylamino)-phosphoramidite-5'-O-(4,4'-dimethoxytrityl-5-seleno-thymidine according to an embodiment of the disclosure.
Figure 23:
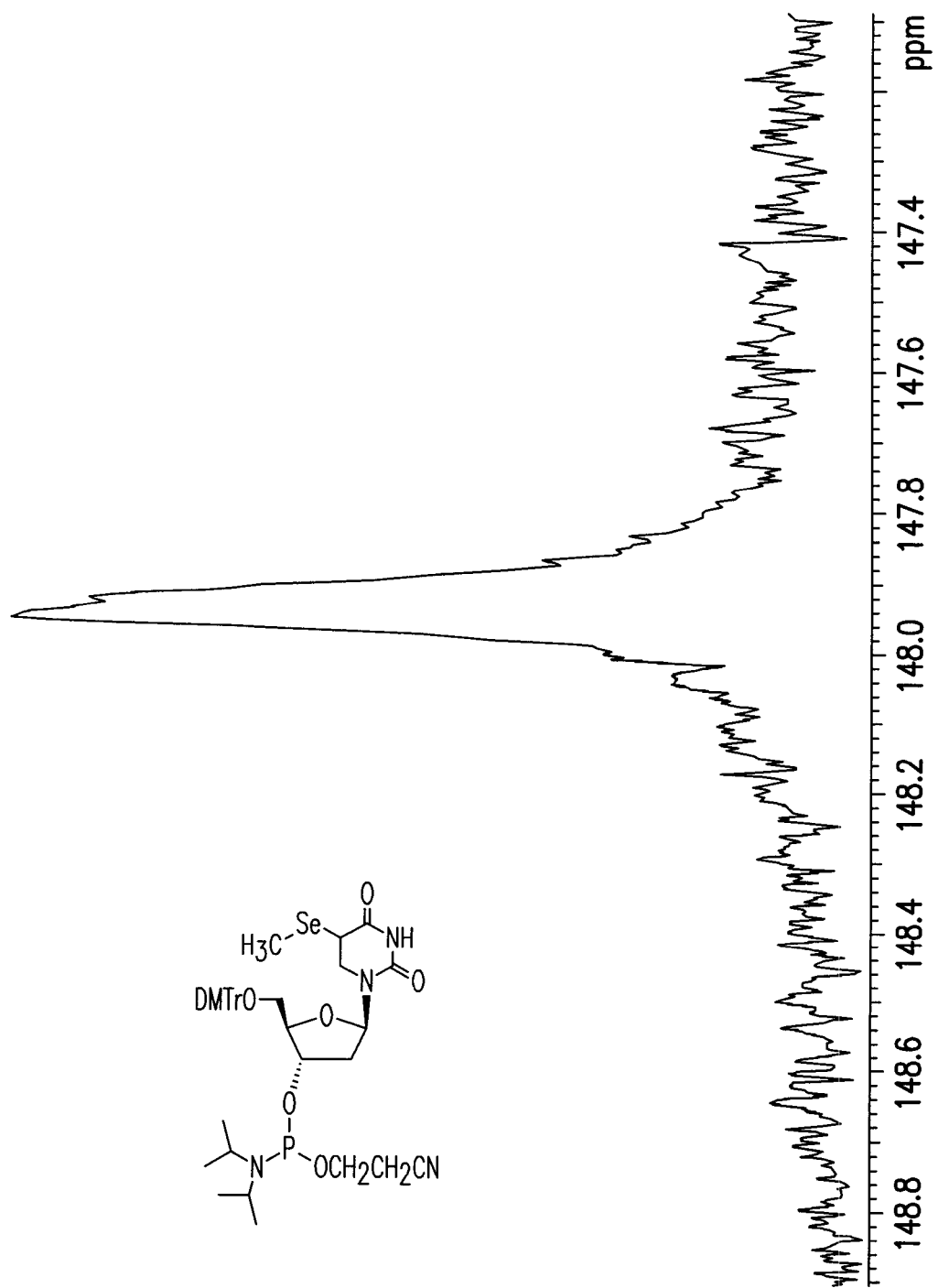
FIG. 23. Detailed $^{31}$P-NMR spectrum of 3'-O-(2-cyanoethyl-N,N-diisopropylamino)-phosphoramidite-5'-O-(4,4'-dimethoxytrityl-5-seleno-thymidine according to an embodiment of the disclosure.

3'-O-(2-cyanoethyl-N,N-diisopropylamino)-phosphoramidite-5'-O-(4,4'-dimethoxytrityl-5-seleno-thymidine (1). Disopropyl-ethylamine (20 μL, 0.12 mmol) was added to a solution of 6 (0.1 g, 0.16 mmol), s-benzylthiotetrazole (15.4 mg, 0.08 mmol) and 2-cyanoethyl-N,N,N,N-tetraisopropyl phosphene (96 mg, 0.32 mmol) in dry CH$_2$Cl$_2$ (5 mL) at 0° C. The mixture was stirred for 2 h at room temperature then slowly poured into pentane (100 mL). The produced white precipitate was filtered off, dissolved in CH$_2$Cl$_2$ (1 mL), and precipitated in pentane. The collected fine powdered white solid was dissolved in CH$_2$Cl$_2$ and dried under reduced pressure to give 108 mg, 82% of 5 as a mixture of two diasteromers and was directly used for solid phase synthesis. An analytically pure sample was purified by a preparative TLC (eluate: 30% EtOAc in CH$_2$Cl$_2$) to give a mixture of two diasteromers: $^1$H-NMR (CD$_3$CN, two sets of signals for a mixture of two diasteromers) δ; 9.16 (1H, s, NH, exchanged with D$_2$O), 7.76 and 7.17 (1H each, s, H-6), 7.52-7.22 (9H, m, DMTr), 6.95-6.82 (4H, m, DMTr), 6.19 (1H, dd, H-1'), 4.57 (1H, m, H-3'), 4.10 and 4.05 (1H, m, H-4'), 3.75 (6H, 2 s, OMe), 3.65 and 3.55 (m, CH-ipr), 3.30 (2H, m, H5'a and H5'b), 2.63-2.51 (2H, dd, CH$_2$), 2.47-2.31 (1H, H-2'$_a$ and H-2'$_b$), 1.96 (3H, s, SeCH$_3$), 1.17-1.03 (2×24H, m, CH$_3$-iPr) (FIG. 22); $^{13}$C-NMR (CD$_3$CN, two sets of signals for a mixture of two diasteromers) δ; 162.63 (C4), 159.82 (Ar), 151.21 (C2), 146.01 (Ar), 141.65 and 141.57 (C-6), 136.84 (Ar), 136.79 (Ar), 136.73 (Ar), 132.30 (Ar), 131.20 (Ar), 131.17 (Ar), 131.15 (Ar), 129.76 (Ar), 129.12 (Ar), 127.98 (Ar), 114.20 (Ar), 104.44 and 104.32 (C-5), 118.80 and 118.38 (CN), 87.52 (Ar), 86.38 and 86.34 (C4'), 86.14 and 86.08 (C-1'), 74.54 and 74.37 (C-3'), 64.41 and 64.23 (C-5'), 59.64 and 59.45 (OMe), 44.15 and 44.03 (C2'), 40.47, 40.43, 40.37, 40.32 (CH-iPr), 24.99, 24.93 and 24.86 (CH$_3$-iPr), 21.13, 21.06, 20.99 (CH$_2$), 7.09 and 7.05 (SeCH$_3$); $^{31}$P-NMR (CD$_3$CN) δ: 147.95, 147.92 (FIG. 23); HRMS (ESI-TOF): Molecular formula, C$_{40}$H$_{49}$N$_4$O$_8$PSe: [M–H]$^+$: 823.2403 (calc. 823.2375).

4. Example No. 4

Figure 26:
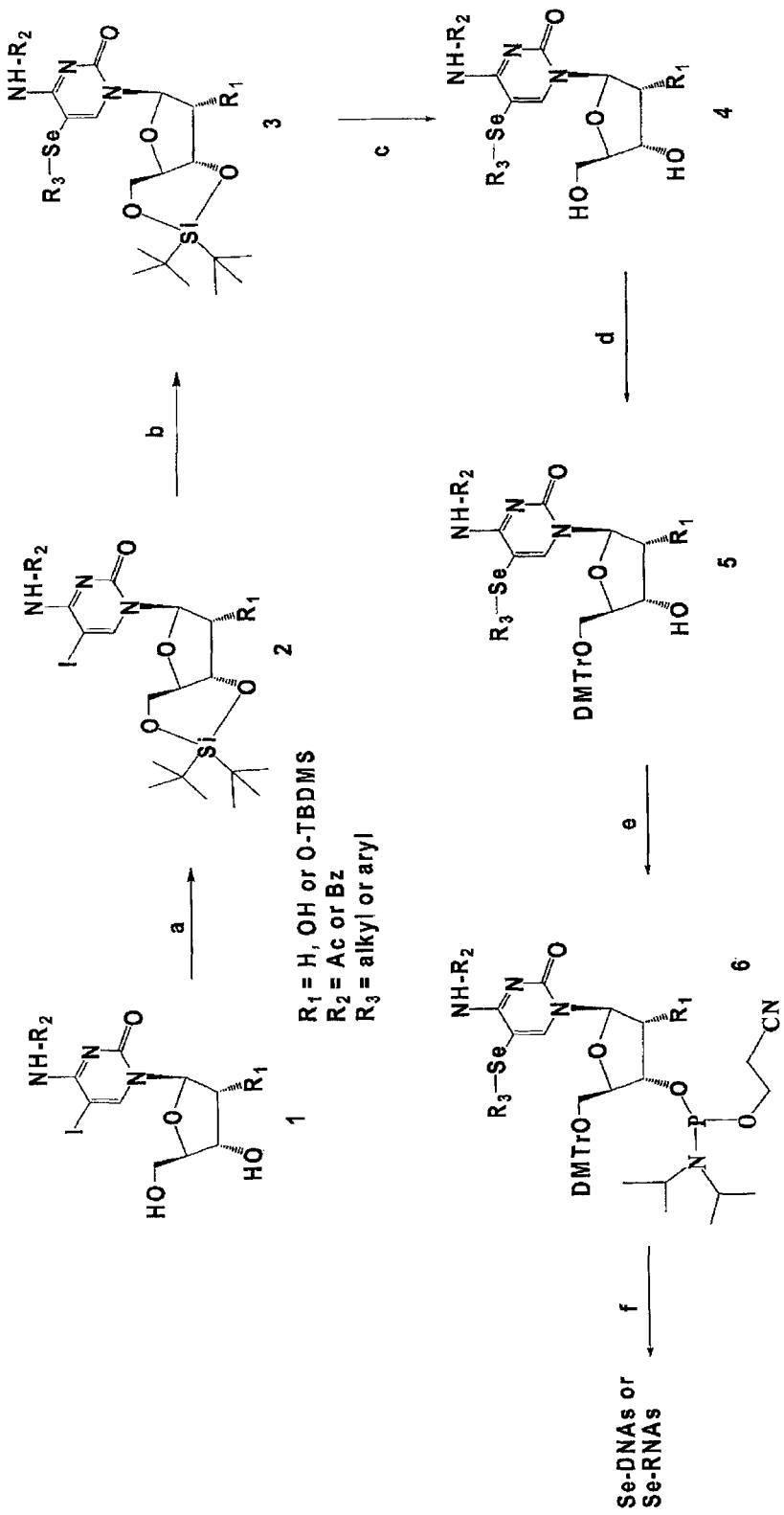
FIG. 26. Representation of synthesis of the 5-Se-cytidine, 5-Se-2'-deoxycytidine, and Se-nucleic acid derivatives according to some forms of the disclosure.

FIG. 26 depicts synthesis of 5-Se-cytidine, 5-Se-2'-deoxycytidine and Se-nucleic acid derivatives according to an embodiment of the disclosure. The reaction conditions and reagents depicted in FIG. 26 are: a) i) (tert-Bu)$_2$SiTf$_2$, DMF; ii) Im., TBDMS-Cl; b) NaH, THF, rt, 30 min, n-BuLi, –78° C., 30 min., RSeSeR, 1 h; c) HF.Pyridine, CH$_2$Cl$_2$, 0° C., 30 min., d) DMTr-Cl, DMAP, Pyridine; e) i-Pr$_2$NP(Cl)OCH$_2$CH$_2$CN, i-Pr$_2$NEt, CH$_2$Cl$_2$; f) solid phase synthesis.

5. Example No. 5

Figure 27:
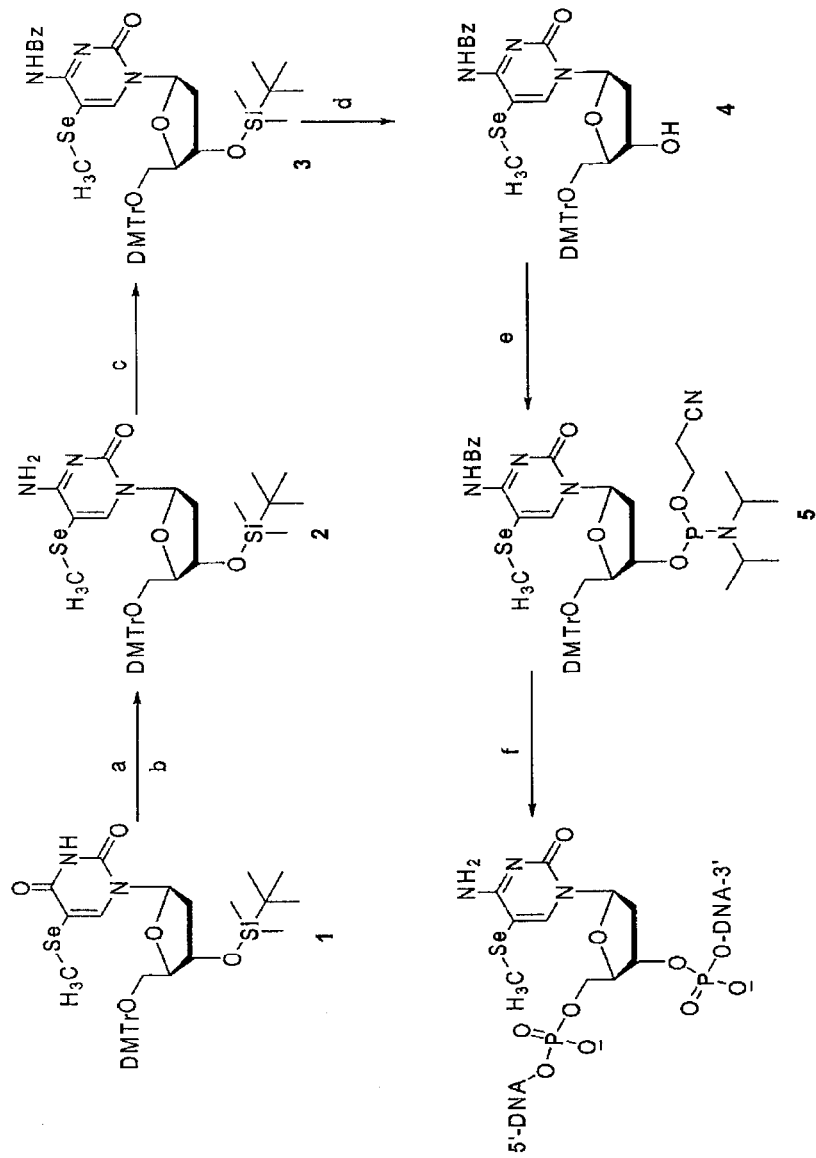
FIG. 27. Representation of conversion of the 5-Se-thymidine derivative to the 5-Se-2'-deoxycytidine and Se-DNA derivatives according to some forms of the disclosure.

In the examples provided below, bold parenthetical numbers refer to compounds as shown in FIG. 27. FIG. 27 shows conversion of the 5-Se-thymidine derivative to the 5-Se-2'-deoxycytidine and Se-DNA derivatives. The reaction conditions and reagents depicted in FIG. 27 are: a) triisopropylbenzenesulfonyl chloride, diisopropylethyl amine, p-dimethylamino pyridine, acetonitrile; b) conc. ammonium hydroxide; c) benzoyl chloride, pyridine; d) tetrabutyl ammonium, fluoride, acetic acid, THF; e) 2-cyanoethyl N,N-diisopropylchlorophosphoramidite, N,N-diisopropylethyl amine, dichloromethane; f) solid-phase synthesis.

5-methylseleno-3'-t-butyldimethylsilyl-5'-O-(4,4-dimethoxytrityl)-2'-deoxycytidine (2). After 5-methylseleno-3'-t-butyldimethylsilyl-5'-O-(4,4-dimethoxytrityl)-2'-deoxyuridine 480 mg (MW 752.2, 0.64 mmol) was dissolved in acetonitrile 10 ml, diisopropylethyl amine (0.67 ml, 3.19 mmol, 5 eq.), triisopropylbenzenesulfonyl chloride (576 mg, 1.59 mmol, 2.5 eq.) and p-dimethylamino pyridine (96 mg, 0.64 mmol, 1 eq.) were added sequentially. The reaction mixture was stirred for 16 hours and monitored on TLC (ethyl acetate/hexane, 3:7). After completion, excessive concentrated ammonium hydroxide solution was added dropwise and the reaction was stirred under room temperature for 1 hour. After the reaction was completed (monitored on TLC, 5% MeOH in CH$_2$Cl$_2$, R$_f$=5), the organic solvent and ammonium hydroxide were evaporated under reduced pressure. A silica gel column was equilibrated with CH$_2$Cl$_2$ before the crude product was loaded and purified on the column. The product was eluded by MeOH in CH$_2$Cl$_2$ (1-7%). The fractions containing the product were combined, evaporated and dried on high vacuum overnight to yield yellow solid 307 mg. (yield=64%). $^1$H-NMR (400 MHz, DMSO) δ: 0.05 (s, 6H, SiCH$_3$), 0.87 (s, 9H, t-butyl), 1.95 (s, 3H, SeCH$_3$), 2.18-2.25 and 2.58-2.62 (2×m, 2H, H-2'), 3.30-3.33 and 3.46-3.49 (2×m, 2H, H-5'), 3.84 (s, 6H, 2×OMe), 4.03-4.08 (m, 1H, H-3'), 4.42-4.46 (m, 1H, H-4'), 6.11 (s, 1H, NH$_2$), 6.28-631 (t, J=5.6 Hz, 1H, H-1'), 6.50 (s, 1H, NH$_2$), 6.86-7.48 (m, 13H, arom-H), 8.30 (s, 1H, H-6). $^{13}$C NMR (100 MHz, DMSO) δ: –4.86 and –4.69 [Si(CH$_3$)$_2$], 7.31 (SeCH$_3$), 17.96 [SiC(CH$_3$)], 25.74 [SiC(CH$_3$)], 41.74 (C-2'), 55.26 (OMe), 62.88 (C-5'), 72.23 (C-3'), 85.55 (C-4'), 87.05 (arom-C), 87.16 (C-1'), 103.45 (C-5), 113.23 (arom-C), 126.94 Carom-C), 128.15 (arom-C), 130.11 (arom-C), 135.50 (arom-C), 141.74 (C-6), 144.41 (arom-C), 149.89 (C-2), 155.46 (arom-C), 158.66 (C-4), 161.46 (arom-C), 165.55 (arom-C). HR-MS (ESI-TOF, positive ion mode): molecular formula, C$_{32}$H$_{47}$N$_3$O$_6$SeSi: [M+H]$^-$: 738.2468 (calc. 738.2478).

4-N-benzoyl-5-methylseleno-3'-t-butyldimethylsilyl-5'-O-(4,4-dimethoxytrityl)-2'-deoxycytidine (3). 5-methylseleno-3'-t-butyldimethylsilyl-5'-O-(4,4-dimethoxytrityl)-2'-deoxycytidine (compound 2) 300 mg (MW 751.3, 0.4 mmol) was placed in a flask and dried on high vacuum for one hour before addition of anhydrous pyridine 10 ml. Benzoyl chloride 0.03 ml (0.6 mmol, 1.5 eq.) was added dropwise before the reaction solution was stirred for 1 hour. After the reaction was completed (monitored on TLC, 30% ethyl acetate in hexane, R$_f$=0.5), the crude product was extracted with saturated NaCl solution and ethyl acetate. The organic phase was removed and aqueous phase was extracted with ethyl acetate three times. The combined organic phase was dried over anhydrous MgSO$_4$, the salt was filtered, and the organic solvents were evaporated under reduced pressure. The residue was purified on a silica gel column (equilibrated with hexane) and eluted with an ethyl acetate/hexane gradient (EtOAc in hexane, 10-50%). Compound 3 was isolated and dried to afford a yellow-green solid 287 mg. (yield=84%). $^1$H-NMR (400 MHz, DMSO) δ: 0.09 and 0.04 [2×s, 6H, Si(CH$_3$)$_2$], 0.86 (s, 9H, t-butyl), 2.02 (s, 3H, SeCH$_3$), 2.18-2.20 and 2.43-2.52 (2×m, 2H, H-2'), 3.29-3.33 and 3.43-3.46 (2×m, 2H, H-5'), 3.81 (s, 6H, 2×OMe), 4.05-4.08 (m, 1H, H-3'), 4.41-4.45 (m, 1H, H-4'), 6.30-6.34 (t, J=6.4 Hz, 1H, H-1'), 6.86-7.56 (m, 18H, arom-H), 7.88 (s, 1H, NH), 8.32 (s, 1H, H-6). $^{13}$C NMR (100 MHz, DMSO) δ: −4.89 and −4.69 [Si(CH$_3$)$_2$], 1.03 (SeCH$_3$), 17.95 [SiC(CH$_3$)], 25.73 [SiC(CH$_3$)], 41.86 (C-2'), 55.26 (OMe), 63.05 (C-5'), 72.41 (C-3'), 86.30 (C-4'), 86.77 (C-5), 87.24 (C-1'), 113.27 (arom-C), 127.07 (arom-C), 128.13 (arom-C), 128.27 (arom-C), 129.38 (arom-C), 130.09 (arom-C), 132.67 (arom-C), 133.68 (C-6), 135.51 (NHCO), 144.41 (arom-C), 144.36 (C-2), 158.69 (C-4). HR-MS (ESI-TOF, negative ion mode): molecular formula, C$_{44}$H$_{51}$N$_3$O$_7$SeSi: [M−H]$^-$: 840.2570 (calc. 840.2583)

4-N-benzoyl-5-methylseleno-5'-O-(4,4-dimethoxytrityl)-2'-deoxycytidine (4). 4-N-benzoyl-5-methylseleno-3'-t-butyldimethylsilyl-5'-O-(4,4-dimethoxytrityl)-2'-deoxycytidine (compound 3) 280 mg (MW 8553, 0.33 mmol) was placed in a flask and dried under high vacuum before it was dissolved in anhydrous THF. The solution was placed in an ice-water bath under dry argon tetra-Butylammonium fluoride 0.44 ml (1M solution in THY, 1.2 eq.) and acetic acid 0.03 ml (1.2 eq.) were injected dropwise simultaneously to make solution pH keep about 7. The reaction mixture was stirred for overnight before it was completed (monitored on TLC, 3% methanol in dichloromethane, R$_f$=0.35). The crude product was extracted by EtOAc and NaCl solution (sat.) three times, and the combined organic layer was dried over anhydrous MgSO$_4$, followed by filtration and solvent evaporation. The residue was purified on a silica gel column (equilibrated with CH$_2$Cl$_2$) and eluted with a methanol/dichloromethane gradient (0.5-5%) to afford the desired product compound 4 225 mg. (yield=91%). $^1$H-NMR (400 MHz, DMSO) δ: 2.04 (s, 3H, SeCH$_3$), 2.21-2.26 and 2.69-2.76 (2×m, 2H, H-2'), 3.34-3.47 (2×m, 2H, H-5'), 3.79 (s, 6H, 2×OMe), 4.15-4.17 (m, 1H, H-3'), 4.46-4.48 (m, 1H, H-4'), 6.14-6.17 (t, J=6.4 Hz, 1H, H-1'), 6.84-7.79 (m, 18H, arom-H), 8.48 (s, 1H, H-6). $^{13}$C NMR (100 MHz, DMSO) δ: 11.02 (SeCH$_3$), 41.99 (C-2'), 55.27 (OMe), 63.11 (C-5'), 72.41 (C-3'), 86.67 (C-4'), 86.94 (arom-C), 87.87 (C-1'), 102.39 (C-5), 113.31 (arom-C), 127.07 (arom-C), 128.04 (arom-C), 128.07 (arom-C), 128.29 (arom-C), 129.68 (arom-C), 129.45 (arom-C), 130.00 (arom-C), 130.92 (arom-C), 132.70 (arom-C), 134.22 (arom-C), 135.47 (NHCO), 144.41 (arom-C), 144.32 (C-2), 150.83 (C-6), 158.69 (C-4), 172.28 (arom-C).

3'-O-(2-cyanoethyl-N,N-diisopropylphosphoramidite)-4-N-benzoyl-5-methylseleno-5'-O-(4,4-dimethoxytrityl)-2'-deoxycytidine (5). 4-N-benzoyl-5-methylseleno-5'-O-(4,4-dimethoxytrityl)-2'-deoxycytidine (compound 4) 200 mg (MW 741.2, 0.27 mmol) was placed in a 25 ml round flask and dried on high vacuum. Dry CH$_2$Cl$_2$ 3 ml, N,N-diisopropylethylamine 0.06 ml (0.4 mmol, 1.5 eq.) and 2-cyanoethyl N,N-diisopropylchlorophosphoramidite 80 mg (0.4 mmol, 1.5 eq.) were then added sequentially. The reaction mixture was stirred at room temperature for 2 hours, and the reaction completion was indicated by TLC (3% MeOH/CH$_2$Cl$_2$, R$_f$=0.37 and 0.38, two diastereomers). The reaction was then quenched with NaHCO$_3$ (sat) and extracted with CH$_2$Cl$_2$ three times, and dried over anhydrous MgSO$_4$, followed by filtration and solvent evaporation. The crude product was re-dissolved in CH$_2$Cl$_2$ (3 ml) and this solution was added dropwise to pentane (200 ml) under vigorous stirring to yield yellow precipitate. The pentane solution was decanted carefully (sometimes filtration was necessary) and the crude product was loaded into a silica gel column that was equilibrated with CH$_2$Cl$_2$ containing 1% triethylamine. The product was eluted with an increasing stepwise gradient of MeOH/CH$_2$Cl$_2$ in the presence of 1% triethylamine (1-5%). The fractions containing target compound were combined evaporated under reduced pressure to afford yellow solid 216 mg. (yield=85%).

6. Example No. 6

Figure 28:
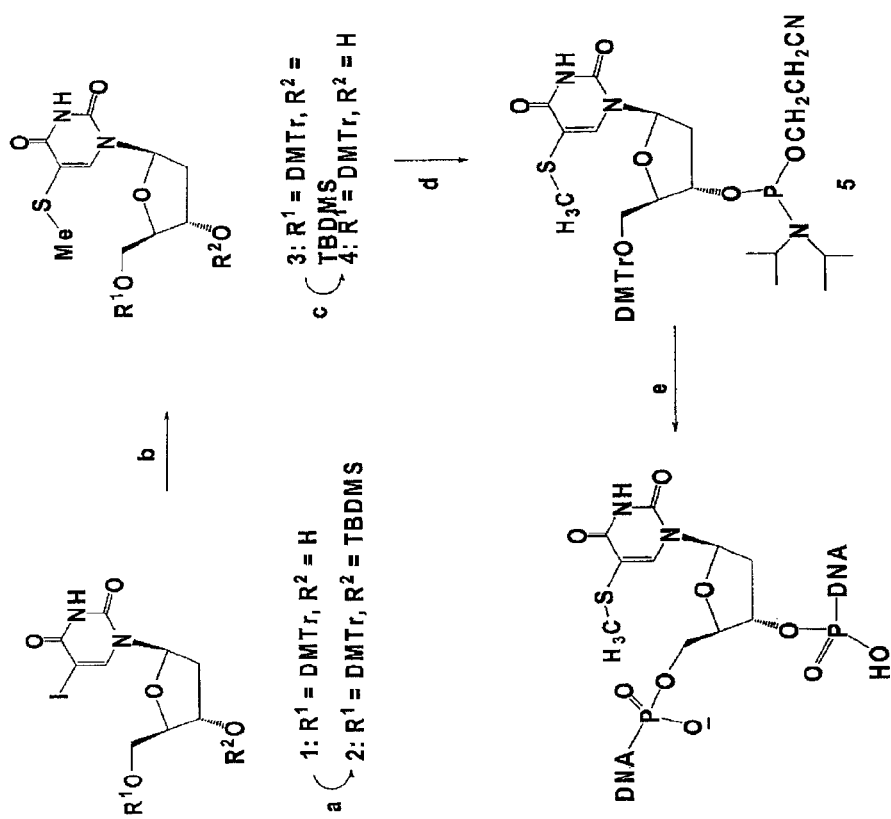
FIG. 28. Representation of synthesis of the 5-S-thymidine and S-DNA derivatives according to some forms of the disclosure.

In the examples provided below, bold parenthetical numbers refer to compounds as shown in FIG. 28. FIG. 28 depicts synthesis of the 5-S-thymidine and S-DNA derivatives according to an embodiment of the disclosure. The synthesis of the 2-seleno-deoxyurine phosphoramidite derivative (5) and the Se-DNAs are outlined in FIG. 3B. A transient N$^3$-imido moiety protection/Lithium-halogen exchange of 5-iodo-2'-deoxyuridine derivative 2 was applied for the synthesis of the corresponding 5-methylthio-2'-deoxyuridine 3. Treatment of the commercially available 5'-O-(4,4-dimethoxytrityl)-2'-deoxy-5-methyltbiouridine (2) with tert-butyldimethylsilyl chloride in the presence of imidazole in DMF gave the corresponding 3'-silyl derivative 3. Contacting 3 with NaH (1.05 equiv) in THF at room temperature for 30 minutes followed by the treatment with n-BuLi (2.2 equiv) at −78° C. and quenching with excess of (CH$_3$)$_2$S$_2$ gave the corresponding 5-methylthio-2'-deoxyuridine derivative 3 in 80% yield as a single regioisomer. Deprotection of the 3'-hydroxyl groups of 3 with TBAF in TIFF gave 4. Phosphitylation of 4 gave the phosphoramidite derivative 5 which was incorporated into DNAs by solid phase synthesis. The reaction conditions and reagents depicted in FIG. 28 are: a) TBDMSCl, Im., DMF; b) NaH, THY, room temperature (rt), 30 min., n-BuLi, −78° C., 30 min., CH$_3$SSCH$_3$, 1 h; c) TBAF, THF, 0° C., 30 min.; d) (i-Pr$_2$N)$_2$P(Cl)OCH$_2$CH$_2$CN, (i-Pr)$_2$NEt, CH$_2$Cl$_2$, e) solid state synthesis.

3'-O-tert-Butyldimethylsilyl-5'-O-(4,4-dimethoxytrityl)-2'-deoxy-S-methylthiouridine (3). NaH 95% (43 mg, 1.69 mmol) was added portion wise to a solution of 2 (Karino 2001) (1.19 g, 1.54 mmol) in dry THF (8 mL) at room temperature in dry glove box. The mixture was stirred for 30 rain until complete cease of hydrogen gas evolution, then cooled down to −78° C. and treated with 1.4 M solution of n-BuLi in hexanes (2.6 mL, 3.72 mmol) dropwise over 15 min. The mixture was stirred for 30 min then treated with (CH$_3$)$_2$S$_2$ (0.9 mL, 10.14 mmol) and the mixture was further stirred for 1 h at the same temperature. Saturated solution of NH$_4$Cl (5 mL) was added and the mixture was warmed to room temperature. Ethylacetate was added to the mixture and the whole was washed with H$_2$O, brine. The organic phase was dried over MgSO$_4$, and evaporated under reduce pressure. The residue was purified by flash silica gel chromatography (eluate: 20% EtOAc in hexanes) gave 3 (1.02 g, 88%) as a colorless foam: $^1$H-NMR (CDCl$_3$) δ: 8.81 (1H, br s, NH, exchanged with D$_2$O), 7.96 (1H, s, H-6), 7.47-7.22 (9 H, m, Ar), 6.88-6.82 (4H, m, Ar), 6.29 (1H, dd, H-1', J=6, J=7.6 Hz), 4.45 (1H, m, H-3'), 4.00 (1H, m, H-4'), 3.79 (6H, 2 s, CH$_3$O), 3.37 (1H, dd, H-5'a, J=3.2, 10.8 Hz), 3.29 (1H, dd, H-5' b, J=3.4, J=10.7 Hz), 2.37 (1H, ddd, H-2'a, J=2.4, J=5.6, J=13.2 Hz), 2.17 (1H, m, H-2'b), 2.11 (3H, s, 5-Sme), 0.85 (9H, s, tert-butyl), 0.03 (3H, s, CH$_3$), −0.01 (3H, s, CH$_3$); $^{13}$C-NMR (CDCl$_3$) δ: 161.64 (C4), 158.85 (Ar), 150.11 (C2), 144.63 (Ar), 140.98 (C-6), 135.78 (Ar), 135.69 (Ar), 130.31 (Ar), 128.28 (Ar), 128.17 (Ar), 127.20 (Ar), 113.47 (Ar), 110.60 (C-5), 87.36 (C4'), 87.10 (Ar), 85.77 (C-1'), 72.75 (C-3'), 63.33 (C-5'), 55.45 (OMe), 41.94 (C2'), 25.94 (CMe$_3$), 18.17 (CMe$_3$), 17.44 (SCH$_3$), −4.69 (SiMe$_2$), −4.86 (SiMe$_2$).

5'-O-(4,4-dimethoxytrityl)-2'-deoxy-5-methylthiouridine (3). A 1 M solution of TBAF in THF (2.6 mL) was added to a solution of 3 (0.95 g, 1.38 mmol) in THF (15 mL) at 0° C. The mixture was stirred for 4 h at room temperature. The solvent was evaporated and the residue partitioned between EtOAc and H$_2$O. The organic phase was dried over MgSO$_4$ and evaporated the residue was purified by silica gel column chromatography (the silica gel was pre-equalized with 1%

Et$_3$N in CH$_2$Cl$_2$, eluate: MeOH in CH$_2$Cl$_2$) to give (0.75 mg, 94%) of 4 as pale yellow foam: $^1$H-NMR (CD$_2$Cl$_2$) δ: 8.98 (1H, s, NH, exchanged with D$_2$O), 7.89 (1H, s, H-6), 7.48-7.20 (9H, m, Ar), 6.85-6.83 (4H, m, Ar), 6.31 (1H, dd, H-1', J=6.0, J=7.6 Hz), 4.54 (1H, m, H-3), 4.09 (1H, m, H-4'), 3.79 (6H, 2 s, OMe), 3.42-3.35 (2H, m, H5'a, and H5'b), 2.54 (1H, br s, 3'-OH), 2.49 (1H, ddd, H-2'$_a$, J=2.4, J=5.6, J=13.6 Hz), 2.26 (1H, m,H-2'$_b$), 2.09 (3H, s, SCH$_3$); $^{13}$C-NMR (CD$_2$Cl$_2$) δ: 161.65 (C4), 158.88 (Ar), 150.23 (C2), 144.64 (Ar), 140.80 (C-6), 135.74 (Ar), 135.63 (Ar), 130.32 (Ar), 129.26 (Ar), 128.45 (Ar), 128.22 (Ar), 127.26 (Ar), 113.52 (Ar), 110.83 (C-5), 87.21 (Ar), 86.50 (C4'), 85.65 (C-1'), 72.75 (C-3'), 63.77 (C-5'), 55.48 (Ar—OCH$_3$), 41.99 (C2'), 17.44 (SCH$_3$).

1-[2'-deoxy-3'-O-(2-cyanoethyl-N,N-diisopropylamino)-phosphoramidite-5'-O-(4,4'-dimethoxytrityl-β-D-erythro-ribofuranosyl]-5-methylthiouridine (5) is synthesized according to the literature procedure: Ahmadian, M., P. M. Zhang, et al. (1998). "A comparative study of the thermal-stability of oligodeoxyribonucleotides containing 5-substituted 2' deoxyuridines." *Nucleic Acids Research* 26 (13): 3127-3135, which is herein incorporated by reference.

7. Example No. 7

Figure 29:
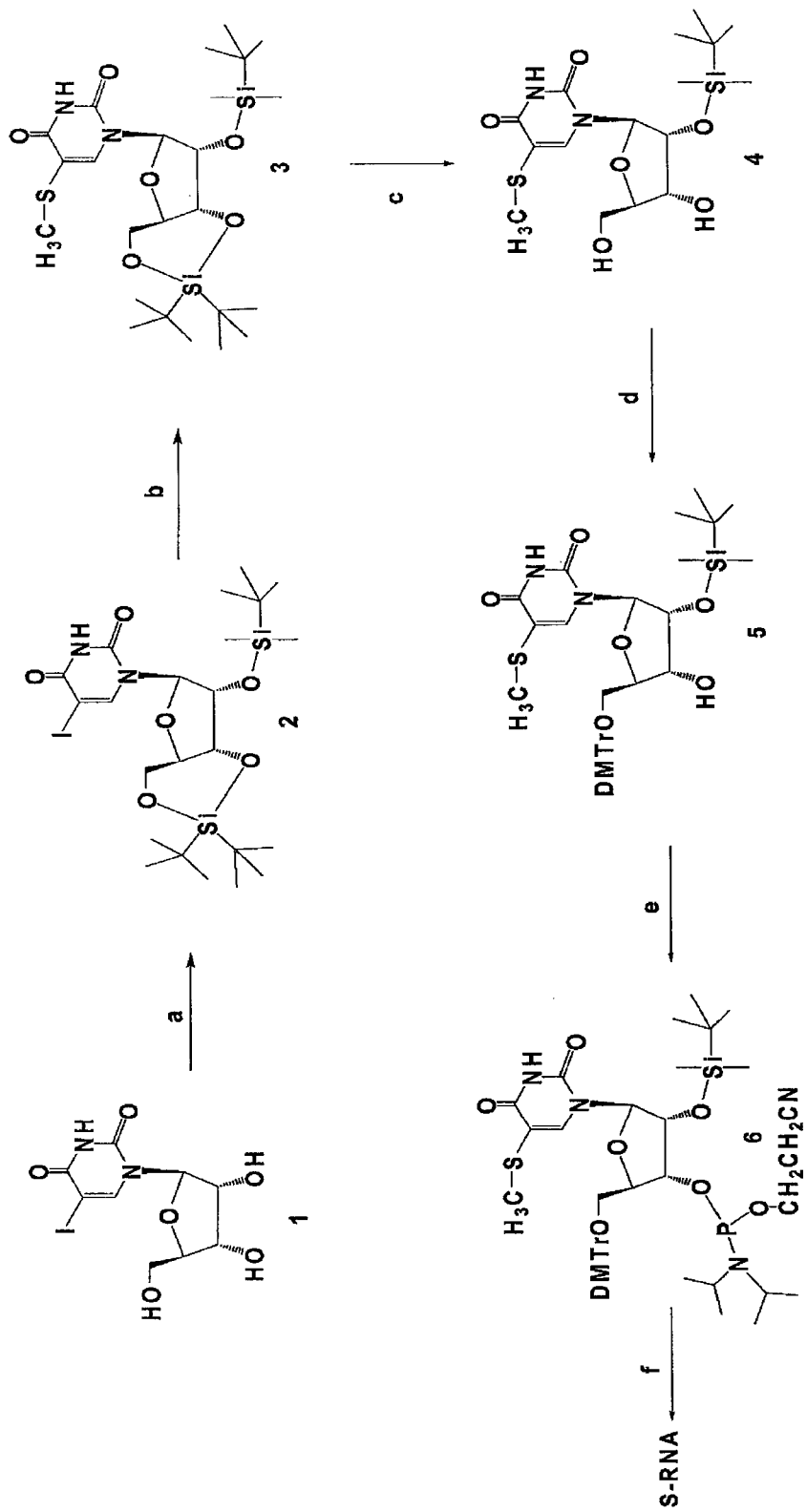
FIG. 29. Representation of synthesis of the 5-methyl-5-uridine and S-RNA derivatives according to some forms of the disclosure.

FIG. 29 depicts the synthesis of 5-methyl-5-uridine and S-RNA derivatives according to some forms of the disclosure. The reaction conditions and reagents depicted in. FIG. 29 are: a) i) (tert-Bu)$_2$SiTf$_2$, DMF; ii) Im., TBDMSCl; b) NaH, THF, rt, 30 min., nBuLi, −78° C., 30 min, CH$_3$SSCH$_3$, 1 h; c) HF.Pyridine, CH$_2$Cl$_2$, 0° C., 30 min.; d) DMTrCl, DMAP, Pyridine; e) (i-Pr$_2$N)$_2$POCH$_2$CH$_2$CN, Pyridinium trifluoroacetate, CH$_2$Cl$_2$; f) solid state synthesis.

8. Example No. 8

Figure 30:
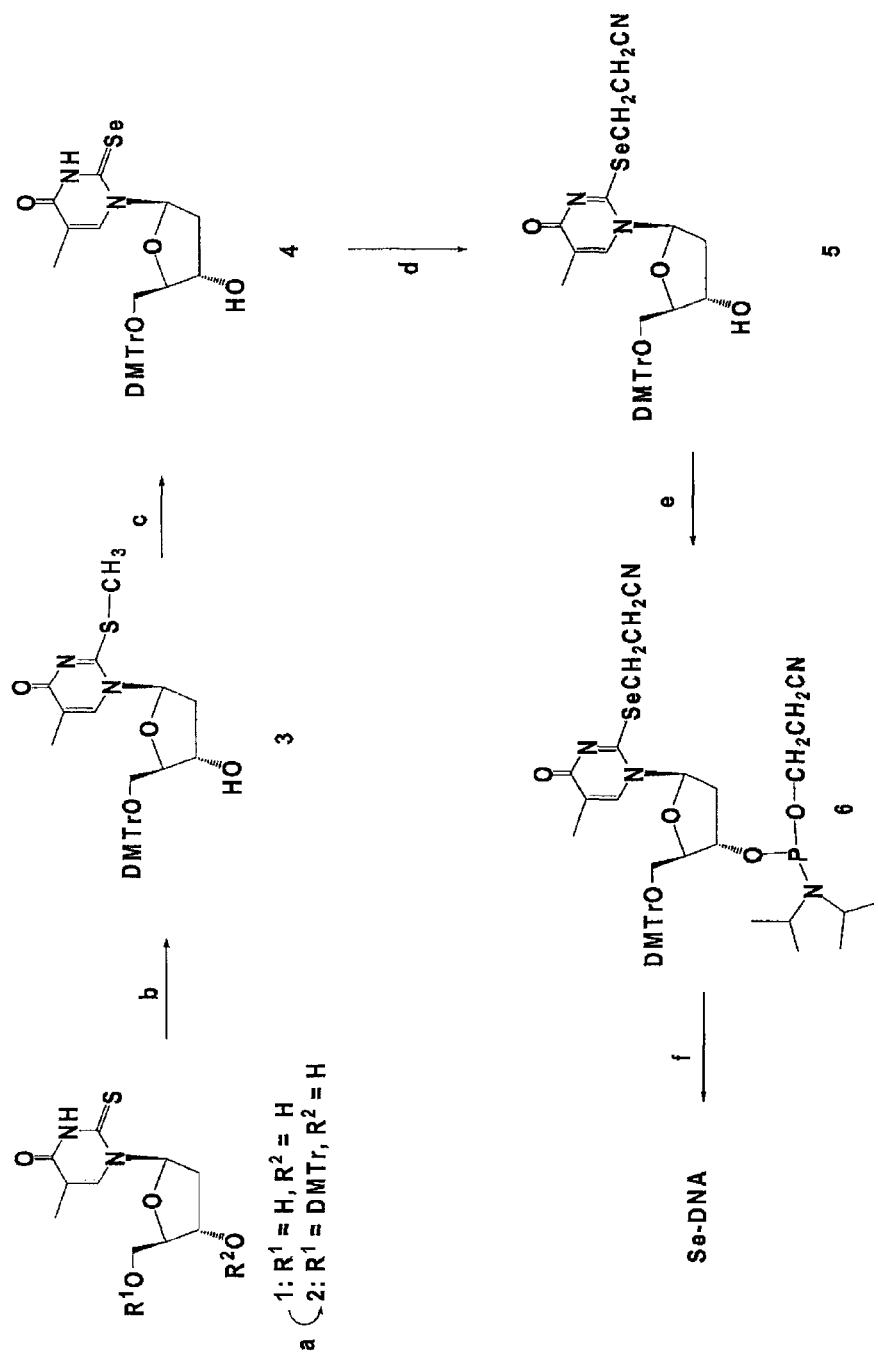
FIG. 30. Representation of synthesis of 2-Se-thymidine and Se-DNA derivatives according to some forms of the disclosure.

FIG. 30 depicts the synthesis of 2-Se-thymidine and Se-DNA derivatives according to some forms of the disclosure. The reaction conditions and reagents depicted in FIG. 30 are: a) DMTrCl, Pyridine, DMAP, r.t.; b) DBU, DMF, CH$_3$I; c) Se, NaBH$_4$, EtOH; d) ICH$_2$CH$_2$CN, i-Pr$_2$NEt, CH$_2$Cl$_2$ e) (i-Pr$_2$N)$_2$P(Cl)OCH$_2$CH$_2$CN, (i-Pr)$_2$NEt, CH$_2$Cl$_2$; f) solid state synthesis.

9. Example No. 9

Figure 31:
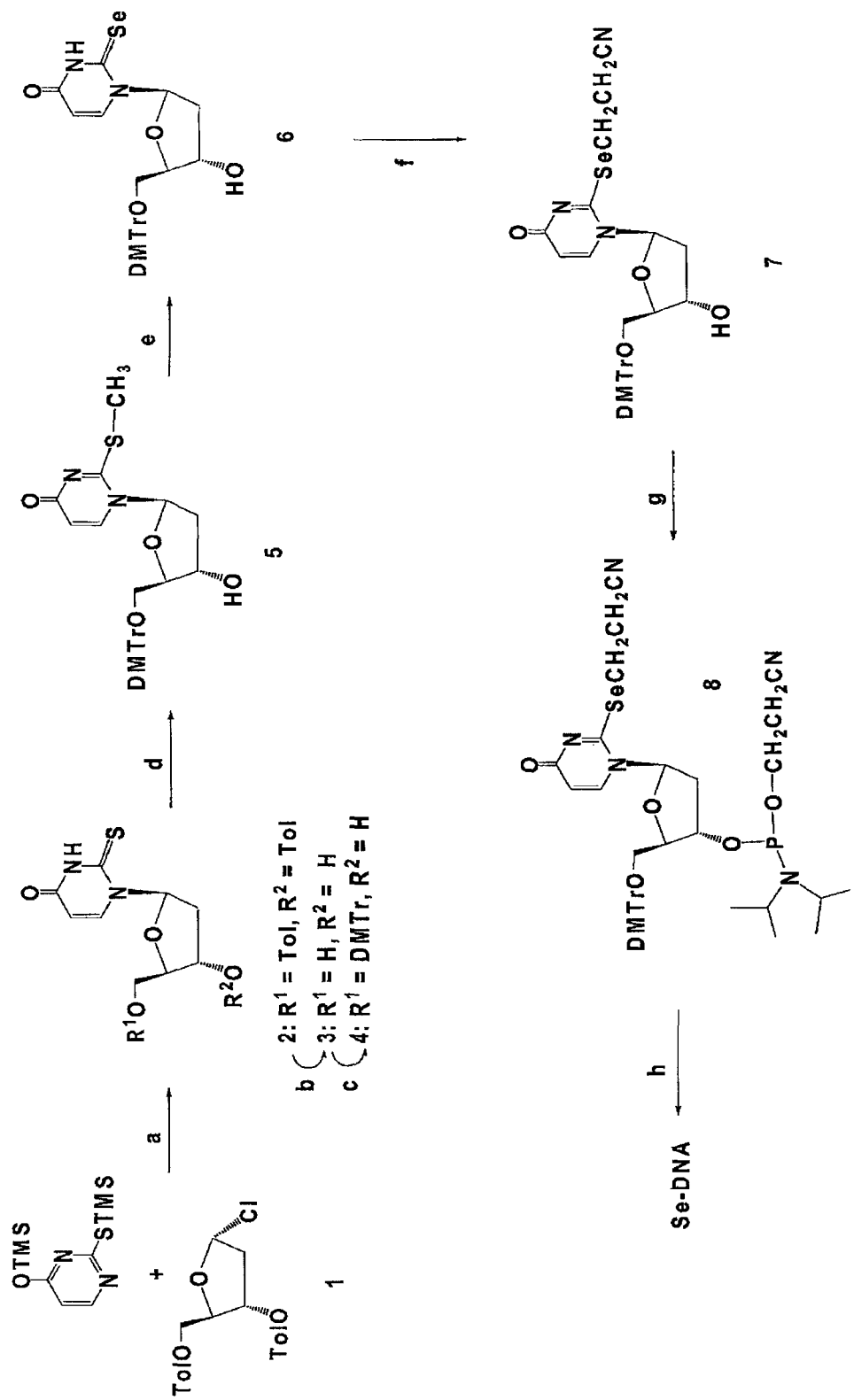
FIG. 31. Representation of synthesis of the 2-Se-2'-deoxyuridine and Se-DNA derivatives according to some forms of the disclosure.

In the examples provided below, bold parenthetical numbers refer to compounds as shown in FIG. 31. The synthesis of the 2-seleno-2'-deoxyurine phosphoramidite derivative (8) and the Se-DNAs are outlined in FIG. 3B. SnCl$_4$ catalyzed coupling of bis-silylated 2-thiouracil with the commercially available 1-(α)-chloro-3,5-di-O-(p-toluoyl)-2-deoxy-D-ribose (1) gave 2-thio-2'-deoxyuridine derivative 2, which was deprotected by NaOCH$_3$ in MeOH to give 2-thio-2'-deoxyuridine (3). Treatment of 3 with 4,4'-dimethoxytrityl chloride in pyridine gave 4 in high yield. Alkylation of 4 with CH$_3$I in the presence of DBU in DMF gave 5, which was treated with NaSeH, generated from Se and NaBH$_4$ in absolute EtOH to give 2-seleno-2'-deoxyuridine derivative 6. Protection of the selenium moiety was achieved by the treatment of 6 with ICH$_2$CH$_2$CN in CH$_2$Cl$_2$ in the presence of i-Pr$_2$NEt to give 7. Phosphitylation of 7 gave the phosphoramidite derivative 8 which was incorporated into DNAs by solid phase synthesis. The reaction conditions and reagents depicted in FIG. 31 are: a) SnCl$_4$, TCE, −30° C.; b) NaOCH$_3$, MeOH; c) DMTrCl, Pyridine, DMAP, r.t.; d) DBU, DMR, CH$_3$I; e) Se, NaBH$_4$, EtOH; f) ICH$_2$CH$_2$CN, i-Pr$_2$NEt, CH$_2$Cl$_2$; g).

3',5'-Di-O-toulyl-2'-deoxy-5-thiouridine (2) and 2'-deoxy-2-thiouridine (3) were synthesized following literature procedure: Kuimelias, Robert G.; Hope, Hakon; Nambiar, Krishnan P. A stereoselective synthesis of α- and β-2'-deoxy-2-thiouridine. *Nucleosides & Nucleotides* (1993), 12(7), 737-55, which is herein incorporated by reference.

5'-O-(4,4'-dimethoxytrityl)-2'-deoxy-2-thiouridine (4) was synthesized following the literature procedure: Kuimelis, Robert G.; Nambiar, Krishnan P. Synthesis of oligodeoxynucleotides containing 2-thiopyrimidine residues, a new protection scheme. *Nucleic Acids Research* (1994), 22(8), 1429-36, which is herein incorporated by reference.

5'-O-(4,4'-dimethoxytrityl)-2'-deoxy-2-thiomethyluridine (5). 1,8-Diazabicyclo[5.4.0]undec-7-ene (0.45 mL) was added to a solution of 4 (1.1 g, 2.01 mmol) and methyl iodide (1.25 mL; 20.1 mmol) in dry N,N-dimethylformamide (10 mL) at 0° C. under Nitrogen atmosphere. The mixture was stirred for 1 hour at 0° C. then ice-H$_2$O (1 g) was added to the mixture. The mixture was diluted with ethylacetate (30 mL) and H$_2$O (10 mL). The organic phase was separated and washed with water (2×10 mL). The organic phase was dried over MgSO$_4$ and the solvent was removed in vacuo. The residue was purified by flash column chromatography (SiO$_2$: 40% ethylacetate in chloroform) to give (0.87 g, 77%) of 5 as a colorless syrup. Spectral data for 5: $^1$H-NMR (CDCl$_3$) δ: 8.09 (1H, d, H-6, J=6.8 Hz), 7.38-7.17 (9H, m, Ar), 6.78-6.74 (4H, m, Ar), 6.20 (1H, dd, H-1', J=6.0, J=6.4 Hz), 5.71 (1H, d, H-5, J=6.8 Hz), 4.69 (2H, br m, H-3' and 3'-OH), 4.16 (1H, m, H-4'), 3.75 (6H, 2 s, OMe), 3.43 (2H, m, H5'a,b), 2.60-2-52 (4H, m, H-2'a and 2-SCH$_3$), 2.82 (1H, m, H-2'b); $^{13}$C-NMR (CD$_2$Cl$_2$) δ: 169.50 (C4), 162.40 (C2), 158.90 (Ar), 144.48 (Ar), 139.37 (C-6), 133.51 (Ar), 135.30 (Ar), 130.30 (Ar), 130.28 (Ar), 128.30 (Ar), 128.21 (Ar), 127.34 (Ar), 113.50 (Ar), 109.37 (C-5), 88.50 (C4'), 87.27 (C-1'), 87.13 (CAr$_3$), 72.82 (C-3'), 62.99 (C-5'), 55.44 (OCH$_3$), 42.19 (C2'), 14.79 (2-SCH$_3$).

5'-O-(4,4'-dimethoxytrityl)-2'-deoxy-2-selenouridine (6). An ethanolic solution of NaSeH [generated from Se (0.38 g, 4.28 mmol) and NaBH$_4$ (0.19 g, 5.14 mmol) in absolute ethanol (10 mL) at 0° C. for 30 minutes] was added to 5 (0.8 g, 1.43 mmol) under nitrogen atmosphere. The mixture was stirred at room temperature for 72 hours, and then saturated aqueous NaCl solution (10 mL) was added to the mixture followed by ethylacetate (30 mL). The organic phase was separated and washed with aqueous NaCl solution (2×10 mL), H$_2$O (10 mL), dried over MgSO$_4$, and evaporated under reduced pressure. The residue was purified by column chromatography (SiO$_2$: 3% MeOH in CHCl3) to give (0.68 g, 81%) of 6 as a yellow foam. Spectral data for 5: $^1$H-NMR (CDCl$_3$) δ: 10.92 (1H, br s, NH), 8.16 (1H, d, H-6, J=8.0 Hz), 7.42-7.24 (9H, Ar), 6.89 (1H, dd, H-1', J=5.2, J=6.0 Hz), 6.86-6.81 (4H, m, Ar), 5.67 (1H, d, H-5, J=8.0 Hz), 4.60 (1H, br m, H—), 4.08 (1H, m, H-4'), 3.88 (6H, 2 s, OMe), 3.60 (1H, br dd, H5'a), 3.45 (1H, dd, H5' b, J=2.8, J=11.2 Hz), 2.67 (1H, m, H-2'a), 2.36 (1H, m, H-2'b); $^{13}$C-NMR (CD$_2$Cl$_2$) δ: 175.65 (C2), 159.46 (C4), 158.94 (Ar), 144.34 (Ar), 141.01 (C-6), 135.32 (Ar), 135.17 (Ar), 130.27 (Ar), 130.25 (Ar), 130.27 (Ar), 128.26 (Ar), 127.24 (Ar), 113.55 (Ar), 108.21 (C-5), 92.79 (C1'), 87.42 (CAr$_3$), 86.75 (C-4'), 70.41 (C-3'), 62.17 (C-5'), 55.47 (OCH$_3$), 41.62 (C2').

5'-O-(4,4'-dimethoxytrityl)-2-cyanoethylselenyl-2'-deoxyuridine (7). Disopropylethylamine (0.25 mL, 1.41 mmol) was added to a solution of 6 (0.17 g, 0.28 mmol) and iodopropionitrile (0.51 g, 2.82 mmol) in CH$_2$Cl$_2$ (3 mL) at 0° C. The mixture was stirred at 0° C. for 30 minutes by which time the starting material was completely consumed. The solvent was removed under reduced pressure and the residue was partitioned between ethylacetate and H$_2$O. The organic phase was dried over MgSO$_4$ and the solvent was removed in vacuo. The residue was purified by flash column chromatography (SiO$_2$: 5% MeOH in CH$_2$Cl$_2$) to give (0.175 g, 95%) of 7 as a colorless glassy solid: Spectral data for 7: $^3$H-NMR (CDCl$_3$) δ: 8.07 (1H, d, H-6, J=7.6 Hz), 7.38-7.19 (9H, m, Ar), 6.83-6.81 (4H, m, Ar), 6.00 (1H, t, H-1', J=6.4 Hz), 5.72 (1H, d, H-5, J=7.6 Hz), 4.80 (1H, br s, 3'-OH), 4.70 (1H, m, H-3' 4.17 (1H, m, H-4'), 3.76 (6H, 2 s, OMe), 3.51 (2H, m, H5'a,b), 3.35 (2H, m, 2-SeCH$_2$CH$_2$CN), 2.95 (2H, m, 2-SeC H$_2$CH$_2$CN), 2.57 (2H, m, H-2'a), 2.34 (1H, m, H-2'b); $^{13}$C-NMR (CDCl$_3$) δ: 171.34 (C2), 168.70 (C4), 158.76 (Ar), 157.46 (Ar), 144.27 (Ar), 139.80 (C-6), 135.28 (Ar), 135.06 (Ar), 130.15 (Ar), 128.16 (Ar), 128.08 (Ar), 127.24 (Ar), 118.83 (CN), 113.38 (Ar), 109.94 (C-5), 90.12 (C1'), 87.33 (C-1'), 87.17 (CAr$_3$), 70.91 (C-3'), 62.08 (C-5'), 60.50 (2-Se—C—C), 55.31 (OCH$_3$), 42.22 (C2'), 60.50 (2-Se—C—C).

1-[2'-deoxy-3'-O-(2-cyanoethyl-N,N-diisopropylamino)-phosphoramidite-5'-O-(4,4'-dimethoxytrityl-β-erythro-ribofuranosyl]-2-cyanoethylselenyluridine (8). Disopropyl-ethylamine (75 μL, 0.42 mmol) was added to a solution of 7 (0.17 g, 0.26 mmol) and 2-cyanoethyl-N,N,N,N-tetraisopropyl phosphane (93 mg, 0.39 mmol) in dry CH$_2$Cl$_2$ (3 mL) at room temperature under nitrogen atmosphere. The mixture was stirred for 3 hours at room temperature then slowly poured into pentane (100 mL). The produced white precipitate was filtered off, dissolved in CH$_2$Cl$_2$ (1 mL), and reprecipitated in pentane. The collected fine powdered white solid was dissolved in CH$_2$Cl$_2$ and dried under reduced pressure to give (190 mg, 86%) of 8 as a mixture of two diasteromers and was directly used for solid phase synthesis. $^{31}$P-NMR (CD$_3$CN) δ: 148.90, 148.95.

10. Example No. 10

Figure 32:
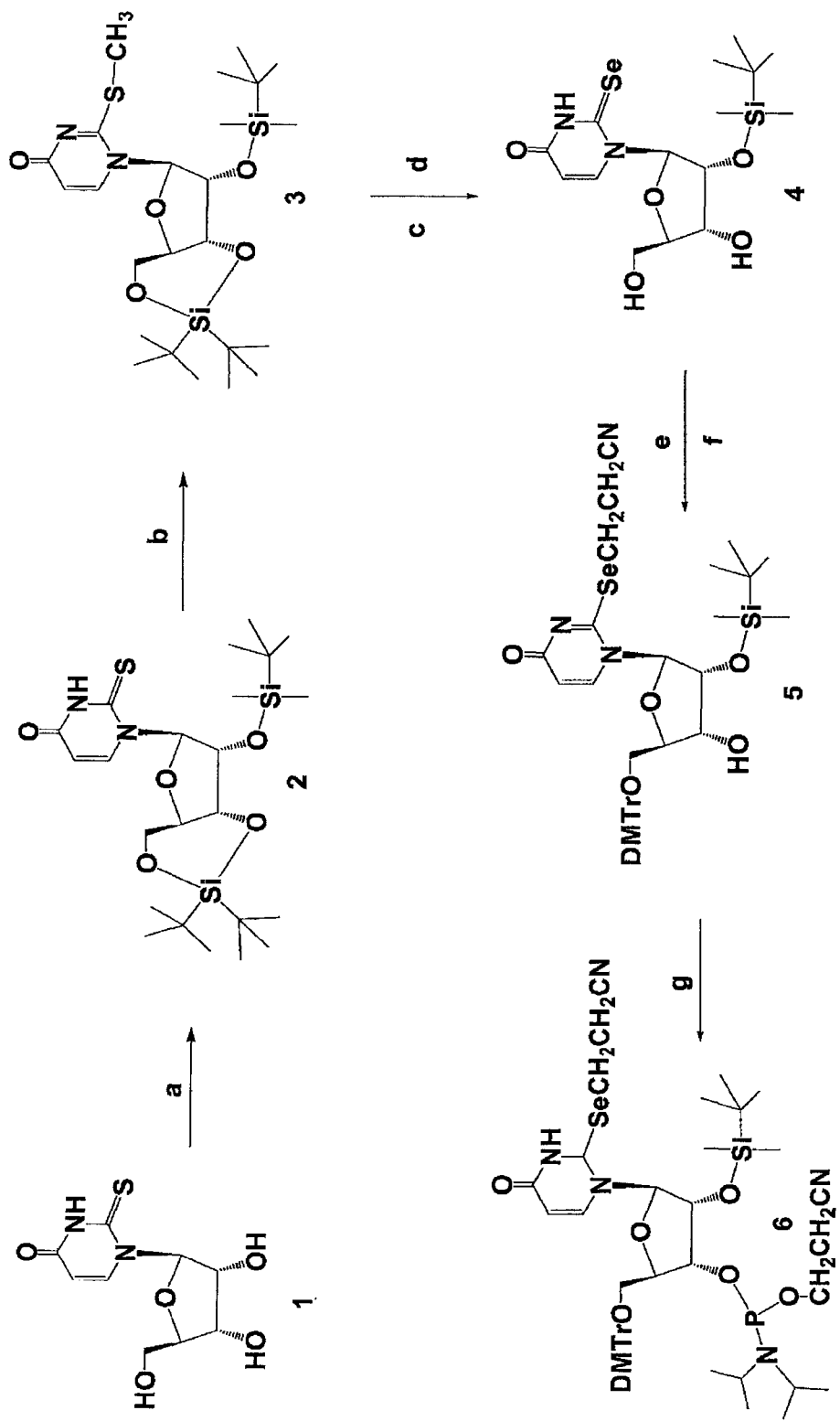
FIG. 32. Representation of synthesis of the 2-Se-uridine and Se-RNA derivatives according to some forms of the disclosure.

FIG. 32 depicts synthesis of 2-Se-uridine and Se-RNA derivatives according to an embodiment of the disclosure. The reaction conditions and reagents depicted in FIG. 32 are: a) i) (tert-Bu)$_2$SiTf$_2$, DMF; ii) Im., TBDMS-Cl; b) DBU, DMR, CH$_3$I; c) Se, NaBH$_4$, EtOH; d) HF.Pyridine, CH$_2$Cl$_2$, 0° C., 30 min.; e) ICH$_2$CH$_2$CN, i-Pr$_2$NEt, CH$_2$Cl$_2$; f) DMTr-Cl, DMAP, Pyridine; g)(i-Pr$_2$N)$_2$POCH$_2$CH$_2$CN, Pyridinium trifluoroacetate, CH$_2$Cl$_2$.

11. Example No. 11

Synthesis of the Se-derivatized nucleic acids (SeNA). DNA oligonucleotides were synthesized chemically on a 1.0 μmol scale using an ABI392 DNA/RNA Synthesizer. The concentration of the Se-nucleoside phosphoramidites was identical to that of the conventional phosphoramidites (0.1 M in acetonitrile). Coupling was carried out using a 5-(benzylmercapto)-1H-tetrazole (5-BMT) solution (0.3 M) in acetonitrile. The coupling time for the Se-nucleoside phosphoramidites was 25 seconds. The 5'-detritylation was done using 3% trichloroacetic acid in methylene chloride. Syntheses were performed on control pore glass (CPG-500) immobilized with the appropriate nucleoside through a succinate linker (Glen Research). All the oligonucleotides were prepared with DMTr-on and the phosphoramidites protected with fast deprotection groups on the nucleobases. After synthesis, the Se-DNA oligonucleotides were cleaved from the solid support and fully deprotected by concentrated ammonia at 50° C. overnight. The SeNAs were then purified twice by HPLC with DMTr-on and DMTr-off, respectively. The DMTr group was removed by 3% TCA treatment for 3 minutes, followed by triethylamine neutralization. The typical MS and HPLC analysis results of the 5-S-T-containing DNAs and 5-Se-T-containing DNAs are presented in FIGS. 7-11 and Table 2.

TABLE 2

MS values of the native and 5-Se-T-containing DNAs

| entry | oligonucleotide | Molecular Formula | Isotopic Mass | Measured (calc.) m/z |
|---|---|---|---|---|
| 1 | 5'-ATGGTGCTC-3' | $C_{88}H_{112}N_{32}O_{54}P_8$ | 2728.5 | [M − H$^+$]$^-$: 2727 (2727.5) |
| 2 | 5'-ATGG$^{5-Se}$TGCTC-3' | $C_{88}H_{112}N_{32}O_{54}P_8Se$ | 2808.4 | [M]$^+$: 2808 (2808.4) |
| 3 | 5'-CTCCCATCC-3' | $C_{84}H_{111}N_{27}O_{53}P_8$ | 2593.5 | (2593.5) |
| 4 | 5'-CTCCCA$^{5-Se}$TCC-3' | $C_{84}H_{111}N_{27}O_{53}P_8Se$ | 2673.4 | [M + H$^+$]$^+$: 2674.5 (2674.4) |
| 5 | 5'-CTTCTTGTCCG-3' | $C_{106}H_{138}N_{32}O_{69}P_{10}$ | 3272.6 | (3272.6) |
| 6 | 5'-CTTCT$^{5-Se}$TGTCCG-3' | $C_{106}H_{138}N_{32}O_{69}P_{10}Se$ | 3351.6 | [M + H$^+$]$^+$: 3352.4 (3352.6) |

12. Example No. 12

Figure 44:
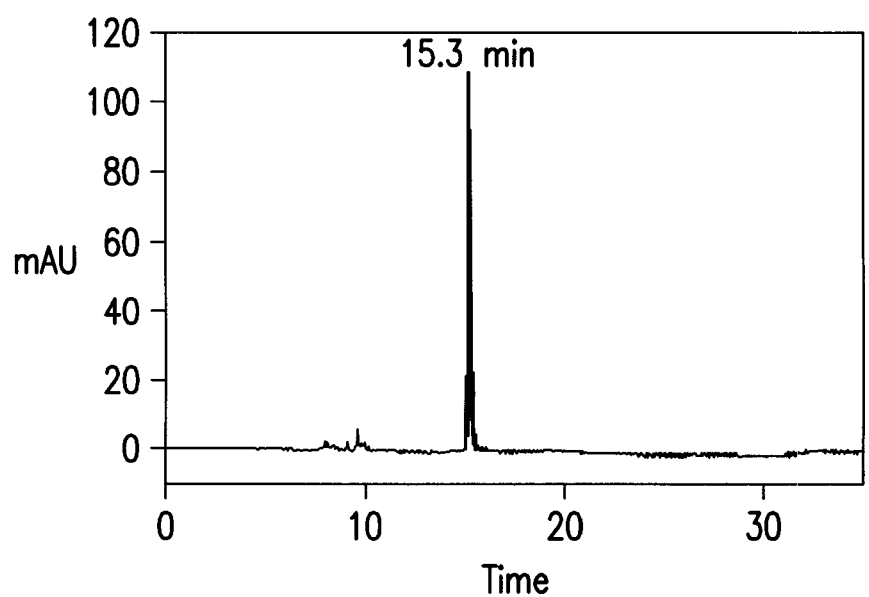
FIG. 44. HPLC analysis of the crude Te-DNA [5'-DMTr-ATGG (5-TePh-T)GCTC-3'] after the solid-phase synthesis and deprotection. The Te-DNA retention time is 15.3 min.
Figure 45:
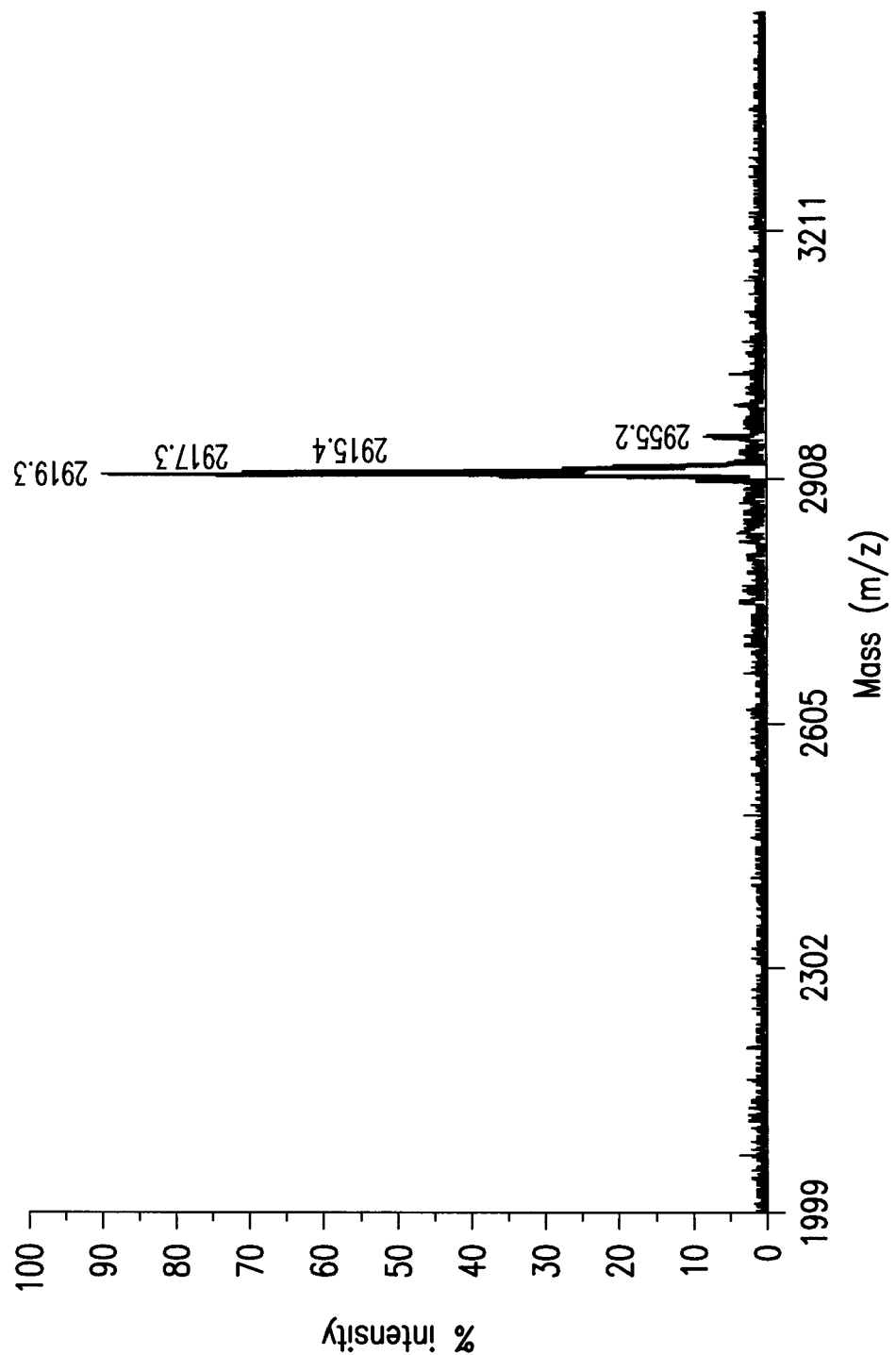
FIG. 45. MALDI-TOF mass spectrum of 5-TePh-9mer: 5'-ATGG (5-TePh-T)GCTC-3; molecular formula: $C_{93}H_{114}N_{32}O_{54}P_8Te$, [M–H$^+$]$^-$: 2919.3 (calculated: 2919.4)
Figure 46:
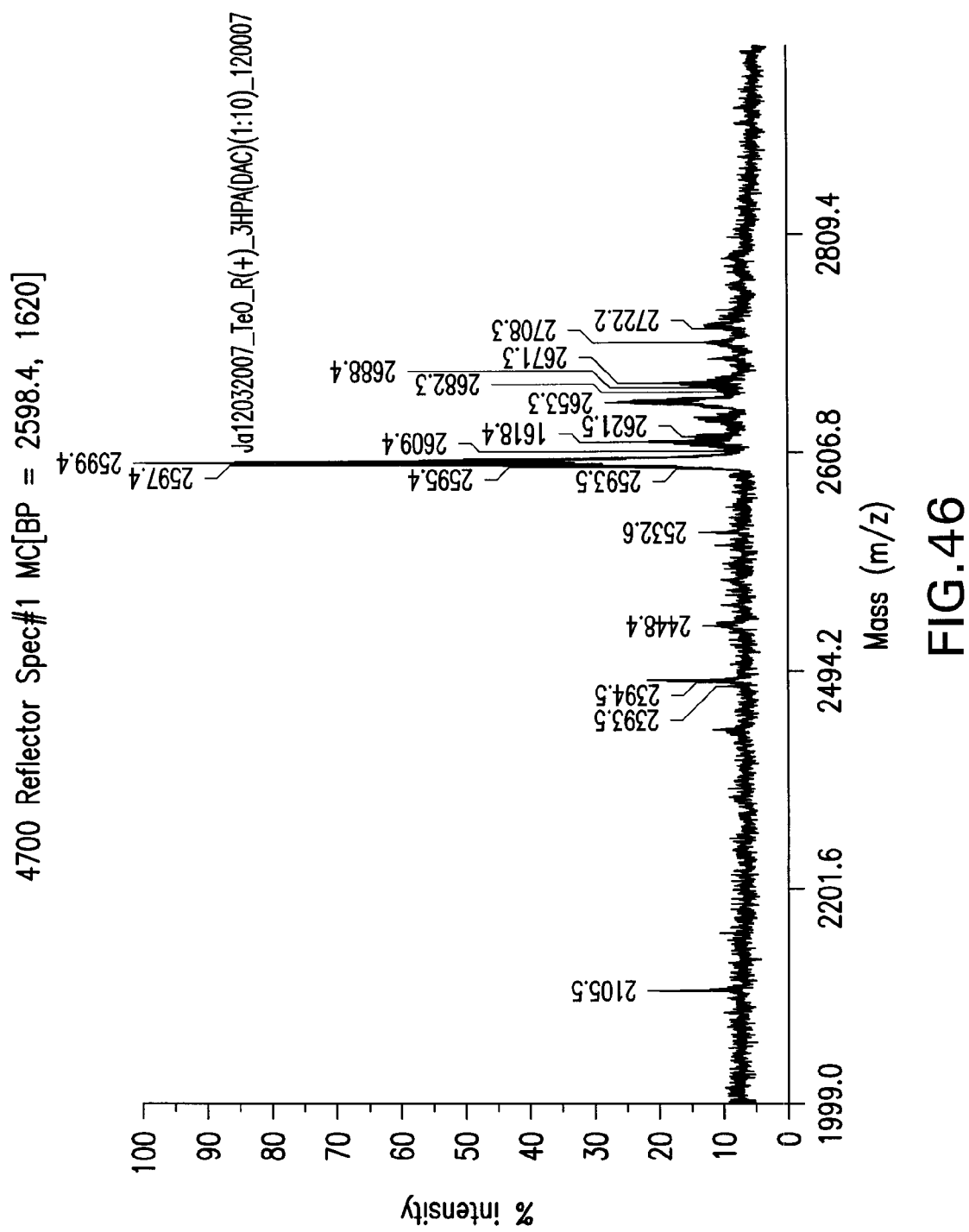
FIG. 46. MALDI-TOF mass spectrum of 5-TePh-8mer: 5'-GTG (5-TePh-T)ACAC-3'; molecular formula: $C_{83}H_{101}N_{30}O_{46}P_7Te$, [M–H$^+$]$^-$: 2599.3 (calculated: 2599.4).
Figure 47:
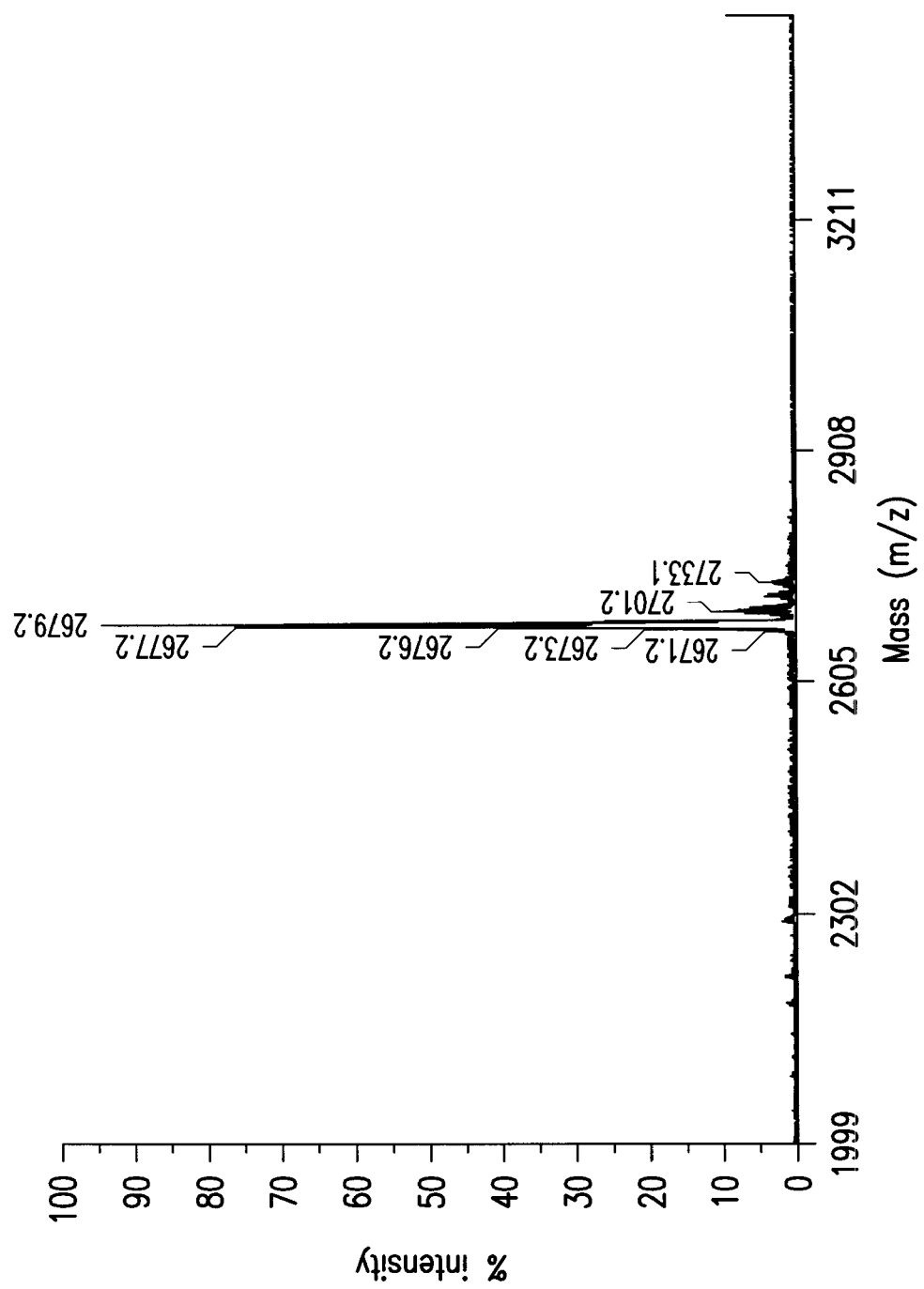
FIG. 47. MALDI-TOF spectrum of Se—Te-8mer: 5'-G(2'-SeMe-dU)G(5-TePh-T)ACAC-3'; Molecular formula: $C_{83}H_{101}N_{30}O_{46}P_7SeTe$; [M–H$^+$]$^-$: 2679.2 (calculated: 26793).

Synthesis of the 5-phenyltelluro-2'-deoxyuridine, its phosphoramidite, and the Te-DNAs. In the examples provided below, bold parenthetical numbers refer to compounds as shown in scheme 3. The Te-DNA synthesis was started from 5-iodo-2'-deoxyuridine derivative 2 as a sodium salt after NaH treatment, followed by the n-BuLi and (PhTe)$_2$ treatment in THF at −78° C. This one-pot reaction gave an inseparable mixture of the desired 5-phenyltelluro derivative (6) and the tentative 6-phenyltelluro derivative (in 10:1 ratio, with 72% yield) along with the reduced by-product (8, in 25% yield). The reaction at higher concentration resulted in 6 exclusively (68% yield) without the formation of the tentative 6-phenyltelluro isomer, accompanied by 8 (22% yield). Desilylation of 6 with TBAF in THF gave 7 in high yield, which was transformed into the 5-phenyltelluro thymdine ($^{Te}$T) phosphoramidite (10) by following the standard procedure. The characteristic tellurium isotope distribution in mass spectra of 6, 7 and 10 confirms the incorporation of the phenyltelluro functionality (Ph-Te). The aromatic phenyl (the protecting group on the 5-Te) may also facilitate DNA conductivity. After synthesis of the Te-modified thymidine analogue (10), its compatibility with solid phase synthesis was examined and HPLC analysis (FIG. 44) showed that this $^{Te}$T-phosphoramidite can be incorporated into DNAs in a high yield (over 95%) and the Te-moiety is stable under the oxidation, capping and deprotection conditions during solid phase synthesis and purification. Several Te-DNA sequences were synthesized and purified (Table 3).

TABLE 3

MALDI-TOF MS of the Te-derivatized DNA oligonucleotides

| Entry | DNA sequences | Measured (Calcd.) m/z |
|---|---|---|
| 1 | ATGG(5-TePh-dU)GCTC $C_{93}H_{114}N_{32}O_{54}P_8Te$ | $[M]^-$: 2919.3 (2919.5) |
| 2 | CTCCCA(5-TePh-dU)CC $C_{89}H_{113}N_{27}O_{53}P_8Te$ | $[M]^-$: 2784.4 (2784.4) |
| 3 | CT(5-TePh-dU)CTTGTCCG $C_{111}H_{140}N_{32}O_{69}P_{10}Te$ | $[M]^-$: 3464.5 (3463.8) |
| 4 | GCG(5-TePh-dU)ATACGC $C_{102}H_{125}N_{38}O_{58}P_9Te$ | $[M + H^+]^+$: 3218.0 (3218.7) |
| 5 | GTG(5-TePh-dU)ACAC $C_{83}H_{101}N_{30}O_{46}P_7Te$ | $[M]^-$: 2599.4 (2599.3) |
| 6 | G(2'-Se-dU)G(5-TePh-dU)ACAC $C_{83}H_{101}N_{30}O_{46}P_7SeTe$ | $[M + H^+]^+$: 2679.2 (2679.2) |

Synthesis of the 5-Te-Functionalized DNA Oligonucleotides

All the DNA oligonucleotides were chemically synthesized in a 1.0 µmol scale using an ABI392 or ABI3400 DNA/RNA Synthesizer. The ultra-mild nucleoside phosphoramidite reagents were used in this work (Glen Research). The concentration of the Te-uridine phosphoramidite was identical to that of the conventional ones (0.1 M in acetonitrile). Coupling was carried out using a 5-(benzylmercapto)-1H-tetrazole (5-BMT) solution (0.25 M) in acetonitrile. The coupling time was 25 seconds for both native and modified samples. 3% trichloroacetic acid in methylene chloride was used for the 5'-detritylation. Synthesis were performed on control pore glass (CPG-500) immobilized with the appropriate nucleoside through a succinate linker. All the oligonucleotides were prepared with DMTr-on form. After synthesis, the DNA oligonucleotides were cleaved from the solid support and fully deprotected by the treatment of 0.05 M $K_2CO_3$ solution in methanol for 8 hr at room temperature. The 5'-DMTr deprotection was performed in a 3% trichloroacetic acid solution for 2 min, followed by neutralization to pH 7.0 with a freshly made aqueous solution of triethylamine (1.1 M) and extraction by petroleum ether to remove DMTr-OH.

HPLC Analysis, Purification and Characterization

The DNA oligonucleotides were analyzed and purified by reverse phase high performance liquid chromatography (RP-HPLC) both DMTr-on and DMTr-off. Purification was carried out using a 21.2×250 mm Zorbax, RX-C8 column at a flow rate of 6 mL/min. Buffer A consisted of 20 mM triethylammonium acetate (TEAAc, pH 7.1), while buffer B contained 50% acetonitrile in buffer A. Similarly, analysis was performed on a Zorbax SB-C18 column (4.6×250 mm) at a flow of 1.0 mL/min using the same buffer system. The DMTr-on oligonucleotides were eluted with up to 100% buffer B in 20 min in a linear gradient, while the DMTr-off oligonucleotides were eluted with up to 70% of buffer B in a linear gradient in the same period of time. The collected fractions were lyophilized and the purified compounds were re-dissolved in water. The pH was adjusted to 7.0 after the final purification of the Se-oligonucleotides without the DMTr group. MALDI-TOF mass is used to characterize all the DNA samples (Table 3). Several examples are shown in FIGS. 44-47.

3'-O-tert-Butyldimethylsilyl-5-O-(4,4-dimethoxytrityl)-2'-deoxy-5-iodouridine (2)

TBDMSCl (0.344 g, 2.3 mmol) was added to a mixture of 5'-O-(4,4-dimethoxytrityl)-2'-deoxy-5-iodouridine (1, 1 g, 1.52 mmol) and imidazole (0.3 g, 4.6 mmol) in anhydrous DMF (10 mL). The mixture was stirred at room temperature for 1.5 h, and then quenched with MeOH. The mixture was diluted with EtOAc (30 mL) and washed with $H_2O$ (3×10 mL) and brine. The organic phase was dried over anhydrous $MgSO_4$ (s) and the solvents were evaporated under reduced pressure. The residue was purified by a flash silica gel column (eluent: 20% EtOAc in hexanes) to give 2 (1.15 g, 98%): $^1$H-NMR (CDCl$_3$, δ): 9.21 (1H, br, NH, exchangeable with D$_2$O), 8.22 (1H, s, H-6), 7.46-7.35 (9H, m, Ar), 6.89-6.86 (4H, m, Ar), 6.31 (1H, dd, H-1', J=5.9, J=7.5 Hz), 4.49 (1H, m, H-3'), 4.15 (1H, m, H-4'), 3.82 (6H, 2 s, CH$_3$O), 3.45 (1H, dd, H-5'a, J=2.7, J=10.8 Hz), 332 (1H, dd, H-5' b, J=3.1, J=10.8 Hz), 2.42 (1H, ddd, H-2'a, J=2.7, J=5.8, J=13.3 Hz), 2.20 (1H, m, H-2'b), 0.87 (9H, 3 s, SiMe$_3$), 0.05-0.002 (6H, 2s, SiMe$_2$): $^{13}$C-NMR (CDCl$_3$) δ 160.41 (C4), 158.67 (Ar), 150.23 (C2), 144.37 (C-6), 144.33 (Ar), 135.54 (Ar), 135.46 (Ar), 130.13 (Ar), 130.08 (Ar), 128.10 (Ar), 127.06 (Ar), 113.39 (Ar), 87.29 (C4'), 86.96 (Ar), 85.85 (C-1'), 72.43 (C-3'), 68.66 (C-5), 63.03 (H5'), 55.27 (OMe), 42.00 (C2'), 25.78 (CCH$_3$), 17.97 (CCH$_3$), −4.63 (SiCH$_3$), −4.84 (SiCH$_3$); HRMS (ESI-TOF): Molecular formula: $C_{36}H_{42}N_2O_7Si$; $[M-H]^+$: 769.1800 (calc. 769.1806).

3',5'-Di-O-tert-butyldimethylsilyl-2'-deoxy-5-iodouridine (4)

TBDMSCl (1.28 g, 8.43 mmol) was added to a mixture of 5-iodo-2'-deoxyuridine (3, 1 g, 2.81 mmol) and imidazole (1.3 g, 8.5 mmol) in anhydrous DMF (10 mL). The mixture was stirred at room temperature for 2 h, and then quenched with MeOH. The mixture was diluted with EtOAc (30 mL) and washed with $H_2O$ (3×10 mL) and brine. The organic phase was dried over anhydrous $MgSO_4$ (s) and the solvents were evaporated under reduced pressure. The residue was purified by a flash silica gel column (eluent: 30% EtOAc in hexanes) to give 4 (1.34 g, 99%) as white foam: $^1$H-NMR (CDCl$_3$, δ): 9.35 (1H, br, NH, exchangeable with D$_2$O), 8.06 (1H, s, H-6), 6.26 (1H, dd, H-1', J=5.7, J=7.9 Hz), 4.38 (1H, m, H-3'), 3.97 (1H, m, H-4'), 3.86 (1H, dd, H-5'a, J=2.2, J=11.5 Hz), 3.76 (1H, dd, H-5' b, J=2.4, J=11.5 Hz), 2.30 (1H, ddd, H-2'a, =2.3, J=5.7, J=13.1 Hz), 1.98 (1H, m, H-2'b), 0.93 (9H, s, SiCMe$_3$), 0.88 (9H, s, SiCMe$_3$), 0.14-0.06 (12H, 4s, SiMe$_2$); $^{13}$C-NMR (DMDO-d$_6$) δ 160.50 (C4), 150.34 (C2), 144.51 (C-6), 88.49 (C4'), 88.13 (C-1'), 72.60 (C-3'), 68.69 (C5), 63.14 (C-5'), 41.70 (C2'), 26.47 (CMe$_3$), 25.89 (CMe$_3$), 18.95 (CMe$_3$), 18.12 (CMe$_3$), −4.50 (SiMe$_2$), −4.70 (SiMe$_2$), −4.83 (SiMe$_2$), −4.96 (SiMe$_2$); HRMS (ESI-TOF): Molecular formula: $C_{21}H_{40}N_2O_5ISi_2$; $[M+H^+]^+$: 583.1525 (calc. 583.1521).

3',5'-Di-O-tert-butyldimethylsilyl-2'-deoxy-5-phenyltellurouridine (5)

NaH 95% (6 mg, 0.25 mmol) was added to a solution of 4 (0.15 g, 025 mmol) in dry THF (1 mL) at room temperature in dry glove box. The mixture was stirred for 30 min until complete cease of hydrogen gas evolution, then cooled down to −78° C. n-BuLi (0.36 mL, 2.3 M solution in hexanes; 0.83 mmol) was added dropwise over 5 min. The mixture was stirred for 30 rain, and then treated with $(Ph)_2Te_2$ (0.25 g, 0.75 mmol). The mixture was further stirred for 1 h at the same temperature (−78° C.). NaCl (5 mL, saturated aqueous solution) was added, the reaction flask was placed at room temperature and allowed to warm up naturally to the room temperature. Water (10 mL) was added to the flask and EtOAc (3×20 mL) was used to extract the crude product. The organic phase was dried over $MgSO_4$, and evaporated under reduce pressure. The residue was purified by flash silica gel chromatography (eluent: 40% EtOAc in hexane containing 1% $Et_3N$) to give 5 (106 mg, 64%) as a colorless foam. Elution with 50% EtOAc in hexane gave 9 (33 mg, 29%) as a colorless foam. Spectral data for 7: $^1H$-NMR ($CDCl_3$, δ): 8.64 (1H, br, NH, exchangeable with $D_2O$), 7.82 (1H, s, H-6), 7.81-7.78 (2H, m, Ar), 7.33-7.24 (3H, m, Ar), 6.25 (1H, dd, H-1', J=5.6, J=8.0 Hz), 4.31 (1H, m, H-3'), 3.92 (1H, m, H-4'), 3.63-3.54 (2H, m, H-5'a,b), 2.30 (1H, ddd, H-2'a, J=2.4, J=5.6, J=13.2 Hz), 1.94 (1H, m, H-2'b), 0.90 (9 H, s, $SiCMe_3$), 0.88 (9 H, s, $SiCMe_3$), 0.09-0.07 (12H, 4s, $SiMe_2$); $^{13}C$-NMR (DMDO-$d_6$) δ 162.65 (C4), 150.21 (C2), 149.77 (C-6), 138.62 (Ar), 129.56 (Ar), 128.41 (Ar), 113.08 (C-5), 89.12 (Ar), 88.48 (C4'), 85.85 (C-1'), 72.57 (C-3'), 63.16 (C-5'), 42.04 (C2'), 26.18 ($C\underline{Me}_3$), 26.08 ($C\underline{Me}_3$), 18.42 ($C\underline{Me}_3$), 18.42 ($C\underline{Me}_3$), −4.48 ($SiMe_2$), −4.66 ($SiMe_2$); HRMS (ESI-TOF): Molecular formula: $C_{27}H_{43}N_2O_5Si_2Te$; $[M-H^+]^+$: 661.1775 (calc. 661.1773).

3'-O-tert-Butyldimethylsilyl-5'-O-(4,4-dimethoxytrityl)-2'-deoxy-5-phenyltellurouridine (6)

NaH 95% (19 mg, 0.67 mmol) was added portion wise to a solution of 2 (0.516 g, 0.67 mmol) in dry THF (2 mL) at room temperature in dry glove box. The mixture was stirred for 30 min until complete cease of hydrogen gas evolution, then cooled down to −78° C. and treated with n-BuLi (1.0 mL, 2.3 M solution in hexane; 2.3 mmol) dropwise over 10 min. The mixture was stirred for 30 min, and then treated with $(Ph)_2Te_2$ (0.75 g, 1.8 mmol). The mixture was further stirred for 1 h at the same temperature (−78° C.). NaCl (10 mL, saturated aqueous solution) was added, the reaction flask was placed at room temperature and allowed to warm up naturally to the room temperature. Water (10 mL) was added to the flask and EtOAc (3×20 mL) was used to extract the crude product. The organic phase was dried over $MgSO_4$ (s), and evaporated under reduce pressure. The residue was purified by flash silica gel chromatography (eluent: 40% EtOAc in hexanes containing 1% $Et_3N$) to give 6 (0.39 g, 68%) as a colorless foam. Elution with 50% EtOAc in hexanes gave 8 (108 mg, 25%) as a colorless foam. Spectral Data for 6: $^1H$-NMR ($CDCl_3$, δ): 9.42 (1H, br, NH, exchangeable with $D_2O$), 7.92 (1H, s, H-6), 7.70-6.86 (18H, m, Ar), 6.29 (1H, dd, H-1', J=6.4, J=8.0 Hz), 4.27 (1H, m, H-3'), 3.99 (1H, m, H-4'), 3.81 (6H, 2 s, $CH_3O$), 3.25 (2H, m, H-5'a,b), 2.37 (1H, ddd, H-2'a, J=2.4, J=5.6, J=13.2 Hz), 2.08 (1H, m, H-2'b), 0.87 (9H, 3 s, $SiMe_3$), 0.09-0.05 (12H, 4s, $SiMe_2$); HRMS (ESI-TOF): Molecular formula: $C_{42}H_{48}N_2O_7TeSi$; $[M+H^+]^+$: 851.2357 (calc. 851.2371).

5'-O-(4,4-dimethoxytrityl-2'-deoxy-5-phenyltellurouridine (7)

TBAF (0.5 mL, 1 M solution in THF) was added to a solution of 6 (026 g, 0.33 mmol) in THF (5 mL) at 0° C. The mixture was stirred for 3 h at room temperature. The solvent was evaporated and the residue was partitioned between EtOAc and $H_2O$. The organic phase was dried over anhydrous $MgSO_4$ (s) before evaporation. The residue was purified by silica gel column chromatography (the silica gel was pre-equalized with 1% $Et_3N$ in $CH_2Cl_2$; eluent 4% MeOH in $CH_2Cl_2$) to give (0.2 g, 84%) of 7 as pale yellow foam. $^1H$-NMR ($CDCl_3$, δ): 9.25 (1H, br, NH, exchangeable with $D_2O$), 7.83 (1H, s, H-6), 7.62-7.01 (15H, m, Ar), 6.86-6.82 (4H, m, Ar), 6.23 (1H, dd, H-1', J=6.4, J=6.8 Hz), 4.34 (1H, m, H-3'), 3.98 (1H, m, H-4), 3.76 (6H, 2 s, $CH_3O$), 3.29 (1H, dd, H-5'a, J=4.4, J=10.4 Hz), 3.18 (1H, dd, H-5' b, J=4.4, J=10.8 Hz), 2.40 (1H, ddd, H-2'a, J=3.6, J=6.0, J=13.6 Hz), 2.16 (1H, m, H-2'b); $^{13}C$-NMR (DMSO-$d_6$) δ 163.40 (C4), 159.33 (Ar), 151.06 (C2), 147.64 (C-6), 145.31 (Ar), 138.41 (Ar), 136.30 (Ar), 136.67 (Ar), 130.64 (Ar), 130.02 (Ar), 128.67 (Ar), 128.60 (Ar), 128.57 (Ar), 127.54 (Ar), 113.95 (C-5), 113.81 (Ar), 89.62 (Ar), 87.33 (Ar), 86.44 (C4'), 85.72 (C-1'), 72.82 (C-3'), 64.26 (C-5'), 55.81 (OMe), 41.35 (C2'); HRMS (ESI-TOF): molecular formula: $C_{36}H_{33}N_2O_7Te$; $[M]^+$: 735.1342 (calc. 735.1350).

1-[2'-deoxy-3'-O-(2-cyanoethyl-N,N-diisopropylamino)-phosphoramidite-5'-O-(4,4-dimethoxytrityl-β-D-erythro-ribofuranosyl]-5-Phenyltellurouridine (10). Disopropylethylamine (44 µL, 0.25 mmol) and N,N-diisopropylamino cyanoethylphosphanaidic chloride (57 mg, 0.24 mmol) were added to a solution of 7 (0.15 g, 0.2 mmol) in $CH_2Cl_2$ (2 mL) at 0° C. The mixture was stirred for 2 h at room temperature, and then was slowly poured into pentane (100 mL) under vigorous stirring. The produced white precipitate was filtered out, dissolved in $CH_2Cl_2$ (1 mL), and re-precipitated in pentane. The collected fine white powder was dried under reduced pressure to give 142 mg 10 (75% yield) as a mixture of two diastereomers, which was directly used for solid phase synthesis without further purification. $^{31}P$-NMR ($CDCl_3$, δ): 149.3, 149.8; HRMS (ESI-TOF): molecular formula: $C_{45}H_{51}N_4O_8PTe$: $[M-H^+]^-$: 935.257 (calc. 935.242).

13. Example No. 13

Synthesis of 2-Se-T phosphoramidite and Se-DNAs

The synthesis started from the 5'-trityl-protection of 2-thiothymidine derivative T (FIG. 30). In order to activate the 2-thio moiety mildly, the 2-thio-functionality of 2 was allylated with $CH_3I$ to give 3. Treatment of 3 with freshly prepared NaSeH gave a clean selenization reaction, and 4 was isolated in 82% yield. The protection of the 2-seleno moiety of 4 was finally achieved with $ICH_2CH_2CN$, giving 5 in 91% yield. Phosphitylation of 5 gave Se-phosphoramidite derivative 6. 2-Se-thymidine ($^{Se}T$) phosphoramidite 6 was found compatible with the conditions of the solid-phase synthesis, and the stability of the protected 2-Se-T moiety allows us to successfully synthesize the Se-oligonucleotides using the ultramild protecting groups. The coupling of 6 into DNA is similar to the native DNA synthesis. The synthesized Se-DNAs were purified and analyzed by HPLC and MS.

1-(2'-Deoxy-5'-O-4,4'-dimethoxytrityl-β-D-erythro-ribofuranosyl)-2-thiothymine (2)

4,4'-Dimethoxytrityl chloride (0.95 g, 2.79 mmol) was added to a solution of 2-thiothymidine (0.6 g, 2.32 mmol) and DMAP (10 mg) in dry pyridine (6 mL) at 0° C. The mixture was stirred for 6 h at rt, and then MeOH (0.5 mL) was added to the mixture. The solvents were evaporated under reduced pressure and the residue was partitioned between EtOAc and $H_2O$. The organic phase was dried ($MgSO_4$) and evaporated.

The residue was purified by flash column chromatography (SiO$_2$, pre-equalized with 1% pyridine in CH$_2$Cl$_2$: 10% EtOAc in CH$_2$Cl$_2$) gave (1.1 g, 85%) of 2 as a colorless foam: UV (MeOH) $\lambda_{max}$ 276 nm, $\lambda_{max}$ 224 nm (shoulder); $^1$H-NMR (CDCl$_3$) δ: 10.35 (1H, br d, NH), 8.64 (2H, m, Ar), 7.88 (1H, d, H-6, J=0.8 Hz), 7.42-7.40-25 (9H, m, Ar), 6.94 (1H, t, H-1' J=6.4 Hz), 6.85-6.82 (4H, m, Ar), 4.61 (1H, m, H-4'), 4.13 (1H, m, H-3'), 3.78 (6H, 2 s, OMe), 3.55 (1H, dd, H5'a, J=2.8, J=10.8 Hz), 3.39 (1H, dd, H5' b, J=2.8, J=10.8 Hz), 2.67 (1H, ddd, H-2'a, J=4.0, J=6.0, J=12.0 Hz), 2.31 (1H, m, H-2'b), 1.46 (3H, s, 5-CH$_3$); $^{13}$C-NMR (CDCl$_3$) δ: 174.30 (C2), 160.94 (C4), 158.93 (Ar), 149.71 (C6), 144.43 (Ar), 136.68 (Ar), 136.42 (Ar), 135.49 (Ar), 130.25 (Ar), 128.28 (Ar), 128.20 (Ar), 127.37 (Ar), 124.02 (Ar), 116.59 (C-5), 113.49 (Ar), 90.05 (C1'), 87.16 (CAr$_3$), 86.80 (C-4'), 71.57 (C-3'), 63.15 (C-5'), 55.43 (OCH$_3$), 41.33 (C2'), 12.24 (5-CH$_3$); HRMS (ESI-TOF) Molecular formula C$_{31}$H$_{32}$N$_2$O$_6$S [M+Na$^+$]$^+$: 583.1883 (calc. 583.1879).

1-(2'-Deoxy-5'-O-4,4'-dimethoxytrityl-β-D-erythro-ribofuranosyl)-2-methylthiothymine (3)

1,8-Diazabicyclo[5.4.0]undec-7-ene (0.4 mL, 2.67 mmol) was added to a solution of 2 (1.0 g, 1.78 mmol) and iodomethane (1.1 mL, 17.8 mmol) in dry N,N-dimethylformamide (6 mL) at 0° C. under Nitrogen atmosphere. The mixture was stirred for 1 hour at 0° C. then ice-H$_2$O (3 mL) was added to the mixture. The mixture was diluted with ethylacetate (30 mL). The organic phase was separated and washed with water (2×10 mL). The organic phase was dried over MgSO$_4$ and the solvent was removed in vacuo. The residue was purified by flash column chromatography (SiO$_2$: 4% MeOH in chloroform) to give (0.84 g, 82%) of 3 as a colorless foam: UV (MeOH) $\lambda_{max}$ 271 nm (shoulder), $\lambda_{max}$ 235 nm; $^1$H-NMR (CDCl$_3$) δ: 7.85 (1H, s, H-6), 7.52-7.18 (9H, m, Ar), 6.88-6.74 (4H, m, Ar), 6.24 (1H, dd, H-1', J=5.6, J=7.2 Hz), 4.64 (1H, m, H-3'), 4.13 (1H, m, H-4'), 3.78 (6H, 2 s, OMe), 3.54 (1H, dd, H-5'a, J=3.2, J=10.8 Hz), 3.41 (1H, dd, H5' b, J=2.8, J=10.8 Hz), 3.2 (1H, br s, 3'-OH), 2.58 (3H, s, 2-SCH$_3$), 2.51 (1H, ddd, H-2'a, J=2.8, J=5.6, J=13.2 Hz), 2.34 (1H, m, H-2'b), 1.55 (3H, s, 5-CH$_3$); $^{13}$C-NMR (CDCl$_3$) δ 169.94 (C4), 161.08 (C2), 159.04 (Ar), 144.478 (Ar), 135.58 (C-6), 135.52 (Ar), 134.76 (Ar), 130.32 (Ar), 128.36.28 (Ar), 128.27 (Ar), 127.44 (Ar), 113.50 (Ar), 119.28 (C-5), 88.30 (C4'), 87.35 (CAr$_3$), 87.02 (C-1'), 72.31 (C-3'), 63.58 (C-5'), 55.50 (OCH$_3$), 41.96 (C2'), 14.95 (2-S CH$_3$), 13.57 (5-CH$_3$); HRMS (ESI-TOF): Molecular formula C$_{32}$H$_{35}$N$_2$O$_6$S[M+H]$^+$: 575.2209 (calc. 575.2216).

1-(2'-Deoxy-5'-O-4,4'-dimethoxytrityl-β-D-erythro-ribofuranosyl)-2-selenothymine (4)

An ethanolic solution of NaSeH [generated from Se (0.38 g, 4.28 mmol) and NaBH$_4$ (0.19 g, 5.14 mmol) in absolute ethanol (15 mL) at 0° C. for 30 minutes] was added to 3 (0.80 g, 1.39 mmol) under nitrogen atmosphere. The mixture was stirred at room temperature for 72 hours, and then saturated aqueous NaCl solution (10 mL) was added followed by ethylacetate (30 mL). The organic phase was separated and washed with aqueous NaCl solution (2×10 mL), H$_2$O (10 mL), dried over MgSO$_4$, and evaporated under reduced pressure. The residue was purified by column chromatography (SiO$_2$: 3% MeOH in CHCl$_3$) to give (0.7 g, 82%) of 4 as a pale yellow foam: UV (MeOH): $\lambda_{max}$ 311 nm, $\lambda_{max}$ 226 nm (shoulder); $^1$H-NMR (CDCl$_3$) δ: 10.63 (1H, br s, NH), 7.94 (1H, s, H-6), 7.39-7.13 (9H, m, Ar), 7.00 (1H, t, H-1', J=6.4 Hz), 6.84 (4H, m, Ar), 4.62 (1H, m, H-3'), 4.14 (1H, m, H-4'), 3.78 (6H, 2 s, OMe), 3.57 (1H, dd, H5'a, J=2.8, J=10.8 Hz), 3.40 (1H, dd, H5' b, J=2.4, J=10.8 Hz), 2.72-2.67 (2H, m, H-2'ab), 1.39 (3H, s, 5-CH$_3$); $^{13}$C-NMR (CDCl$_3$) δ: 173.92 (C2), 160.15 (C4), 158.96 (Ar), 144.35 (Ar), 136.77 (Ar), 135.40 (C-6), 130.27 (Ar), 130.25 (Ar), 130.27 (Ar), 130.25 (Ar), 129.21 (Ar), 128.40 (Ar), 128.29 (Ar), 128.24 (Ar), 118.53 (C-5), 113.55 (Ar), 93.03 (C1'), 87.25 (CAr$_3$), 86.99 (C-4'), 71.75 (C-3'), 63.08 (C-5'), 55.46 (OCH$_3$), 41.46 (C2'), 12.38 (5-CH$_3$); HRMS (ESI-TOF): Molecular formula C$_{31}$H$_{32}$N$_2$O$_6$Se [M+Na$^+$]$^+$: 631.1332 (calc. 631.1323).

1-(2'-Deoxy-5'-O-4,4'-dimethoxytrityl-β-D-erythro-ribofuranosyl)-2-cyanoethylselanylthymine (5)

Disopropylethylamine (0.48 mL, 2.72 mmol) was added to a solution of 4 (0.33 g, 0.54 mmol) and iodopropionitrile[2] (1.5 g, 8.2 mmol) in dry CH$_2$Cl$_2$ (5 mL) at 0° C. The mixture was stirred at 0° C. for 30 minutes by which time the starting material was completely consumed. The solvent was removed under reduced pressure and the residue was partitioned between ethylacetate and H$_2$O. The organic phase was dried over MgSO$_4$ and the solvent was removed in vacuo. The residue was purified by flash column chromatography (SiO$_2$: 5% MeOH in CH$_2$Cl$_2$) to give (0.33 g, 91%) of 5 as a colorless glassy solid: UV (MeOH) $\lambda_{max}$ 236 nm, $\lambda_{max}$ 271 nm (shoulder); $^1$H-NMR (CDCl$_3$) δ: 7.86 (1H, d, H-6, J=1.2 Hz), 7.40-7.21 (9H, m, Ar), 6.85-6.81 (4H, m, Ar), 6.00 (1H, dd, H-1', J=5.6, J=7.6 Hz), 4.66 (1H, m, H-3'), 4.15 (1H, m, H-4'), 3.78 (6H, 2 s, OMe), 3.51 (1H, dd, H5'a, J=2.8, J=12.8 Hz), 3.46-3.38 (3H, m, H5'a, 2-SeCH$_2$CH$_2$CN), 3.17 (1H, br s, 3'-OH), 3.03 (2H, m, 2-SeCH$_2$CH$_2$CN), 2.51 (1H, ddd, H-2'a, J=2.8, J-6.0, J=13.6 Hz), 2.41 (1H, m, H-2'b), 1.49 (3H, d, 5-CH$_3$, J=0.8 Hz); $^{13}$C-NMR (CDCl$_3$) δ: 169.47 (C2), 159.00 (C4), 155.76 (Ar), 144.35 (Ar), 135.44 (C-6), 135.36 (Ar), 130.29 (Ar), 128.33 (Ar), 128.26 (Ar), 127.45 (Ar), 120.20 (CN), 119.03 (C-5), 113.55 (Ar), 90.24 (C-1'), 87.33 (C-4'), 87.37 (CAr$_3$), 72.28 (C-3'), 63.56 (C-5'), 55.48 (OCH$_3$), 42.22 (C2'), 23.81 (2-Se—CH$_2$—CH$_2$CN), 19.03 (2-Se—CH$_2$CH$_2$CN); HRMS (ESI-TOF): Molecular formula C$_{34}$H$_{36}$N$_3$O$_6$Se [M+H]$^+$: 662.1780 (calc. 662.1769).

2-(2-cyanoethyl)seleno-5'-O-(4,4'-dimethoxytriphenylmethyl)-thymidine 3'-O-(2-cyanoethyl)-diisopropylamino phosphoramidite (6)

Disopropyl-ethylamine (52 µL, 0.3 mmol) was added to a solution of 5 (0.17 g, 0.26 mmol) and 2-cyanoethyl-N,N,N, N-tetraisopropyl phosphane (0.15 g, 0.23 mmol) in dry CH$_2$Cl$_2$ (3 mL) at room temperature under nitrogen atmosphere. The mixture was stirred for 2 hours at room temperature and then the volatiles were removed under reduced pressure without exposure to air. The residue was precipitated from dry pentane and the precipitate was filtered off, dried under reduced pressure to give (6; 162 mg, 82%), which was directly used for solid phase synthesis: $^{31}$P-NMR (CD$_3$CN) δ: 148.90, 148.95; HRMS (ESI-TOF): Molecular formula C$_{43}$H$_{32}$N$_5$O$_7$PSe [M+Cl]$^-$: 896.2441 (calc. 896.2441).

Synthesis of the 2-Se-T Functionalized DNA Oligonucleotides (7).

All the DNA oligonucleotides were chemically synthesized in a 1.0 µmol scale using an ABI392 or ABI3400 DNA/RNA Synthesizer. The ultra-mild nucleoside phosphoramidite reagents were used in this work (Glen Research). The concentration of the 2-Se-T phosphoramidite was identical to that of the conventional ones (0.1 M in acetonitrile). Coupling was carried out using a 5-(benzylmercapto)-1H-tetrazole (5-BMT) solution (0.25 M) in acetonitrile. The coupling time was 25 seconds for both native and modified samples. 3% trichloroacetic acid in methylene chloride was used for the 5'-detritylation. Synthesis were performed on control pore glass (CPG-500) immobilized with the appropriate nucleoside through a succinate linker. All the oligonucleotides were prepared with DMTr-on form. After synthesis, the DNA oligonucleotides were cleaved from the solid support and fully deprotected by the treatment of 0.05 M $K_2CO_3$ solution in methanol for 8 hr at room temperature. The 5'-DMTr deprotection was performed in a 3% trichloroacetic acid solution for 2 min, followed by neutralization to pH 7.0 with a freshly made aqueous solution of triethylamine (1.1 M) and extraction by petroleum ether to remove DMTr-OH.

HPLC Analysis, Purification and Characterization.
the DNA oligonucleotides were analyzed and purified by reversed-phase high performance liquid chromatography (RP-HPLC) both DMTr-on and DMTr-off. Purification was carried out using a 21.2×250 mm Zorbax, RX-C8 column at a flow rate of 6 ml/min. Buffer A consisted of 20 mM triethylammonium acetate (TEAAc, pH 7.1), while buffer B contained 50% acetonitrile in 20 mM triethylammonium acetate (TEAAc, pH 7.1). The DMTr-on oligonucleotides were eluded and purified in a linear gradient reaching 100% buffer B in 20 min, while the DMTr-off oligonucleotides were eluded and purified in a linear gradient reaching 70% buffer B in 20 min. The collected fractions were lyophilized and the purified compounds were re-dissolved in water. The pH was adjusted to 7.0 after the final purification of the Se-oligonucleotides without the DMTr group. Similarly, analysis was performed on a Zorbax SB-C18 column (4.6×250 mm) at a flow of 1.0 mL/min, in a linear gradient reaching 70% buffer B in 20 min. MALDI-TOF MS is used to characterize all Se-DNA samples (Table 3').

tion of thymidine does not cause significant structure perturbation. It is counterintuitive that the larger selenium atom causes less destabilization than the smaller sulfur atom, which is actually consistent with formation of the 5-methyl group and 5'-phosphate interaction in the case of the selenium atomic linker. The longer linker with a selenium atom, comparing with a sulfur atom, allows a stabilizing interaction between the methyl and phosphate moieties.

2. Crystal Structure Study of the Se-Modified DNA Duplex and the Comparison with the Corresponding Native.

Figure 13:
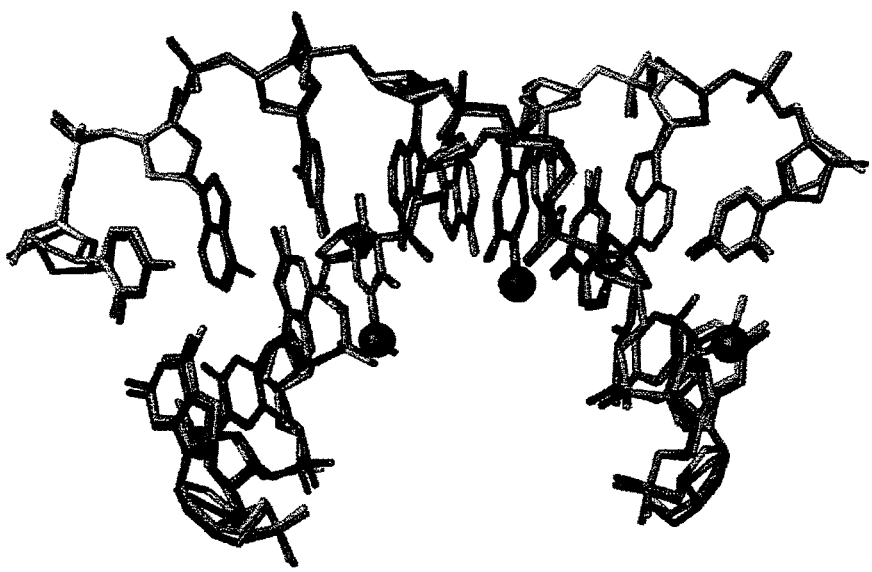
FIG. 13. Structure of the 5-Se-T-DNA [(5'-GdU$_{2'-Se}$-G-$^{5-Se}$T-ACAC-3')$_2$]. The duplex structure of the modified DNA (3BM0, in cyan) is superimposed over the native (1DNS, in pink).

Similar to other Se-derivatized nucleic acids (SeNA) [Salon, J., Jiang, J., Sheng, J., Gerlits, O. O. & Huang, Z. (2008) Nucleic Acids Res 36, 7009-18; Caton-Williams, J. & Huang, Z. (2008) Angew Chem Int Ed Engl 47, 1723-5; Carrasco, N., Ginsburg, D., Du, Q. & Huang, Z. (2001) Nucleosides Nucleotides Nucleic Acids 20, 1723-34; Du, Q., Carrasco, N., Teplova, M., Wilds, C. J., Egli, M. & Huang, Z. (2002) J Am Chem Soc 124, 24-5; Wilds, C. J., Pattanayek, R., Pan, C., Wawrzak, Z. & Egli, M. (2002) J Am Chem Soc 124, 14910-6; Carrasco, N., Buzin, Y., Tyson, E., Halpert, E. & Huang, Z. (2004) Nucleic Acids Res 32, 1638-46; Moroder, H., Kreutz, C., Lang, K., Serganov, A. & Micura, R. (2006) J Am Chem Soc 128, 9909-18], these novel 5-Se-T DNAs are also stable. The crystal growth of the self-complementary Se-DNA (5'-G-dU2'-Se-G-5-SeT-ACAC-3')$_2$ was successfully facilitated by the utilization of 2'-Me-Se-dU [Jiang, J., Sheng, J., Carrasco, & Huang, Z. (2007) Nucleic Acids Res 35, 477-85]. FIG. 13 shows global and local structures of the 5-Se-T-DNA [(5'-G-($_{2'-Se-}$dU)-G-($^{5-Se}$T)-ACAC-3')$_2$]. In FIG. 13, the duplex structure of the modified DNA (3BM0, in cyan) is superimposed over the native (1DNS, in pink). Superimposition of the determined Se-DNA crystal structure (1.8 Å) over the corresponding native in the same tetragonal space group

TABLE 3

MS values of the 2-Se-T-containing DNAs

| Entr | Oligonucleotide | Molecular Formula | Isotopic Mass | Measured (calc.) m/z |
|---|---|---|---|---|
| 1 | T$^{Se}$TTT | $C_{40}H_{35}N_8O_{25}P_3Se$ | 1218.2 | [M + H$^+$]$^+$: 1219.2 (1219.2) |
| 2 | 5'-CTCCCA$^{Se}$TCC-3' | $C_{84}H_{103}N_{27}O_{52}P_8Se$ | 2657.6 | [M + H$^+$]$^+$: 2658.5 (2658.6) |
| 3 | 5'-ATGG$^{Se}$TGCTC-3' | $C_{88}H_{104}N_{32}O_{53}P_8Se$ | 2793.8 | [M + H$^+$]$^+$: 2794.2 (2794.8) |
| 4 | 5'-CTTCT$^{Se}$TGTCCG-3' | $C_{106}H_{128}N_{32}O_{68}P_{10}Se$ | 3338.1 | [M]$^+$: 3338.3 (3338.1) |
| 5 | 5'-GdU$_{2'\cdot SeMe}$G$^{Se}$TACAC-3' | $C_{78}H_{99}N_{30}O_{45}P_7Se_2$ | 2552.3 | [M − H$^+$]$^-$: 2551.3 (2551.3) |

C. Examples of Biological and Other Testings

1. Biophysical Studies of the 5-Se-T Modified DNAs.

Figure 12:
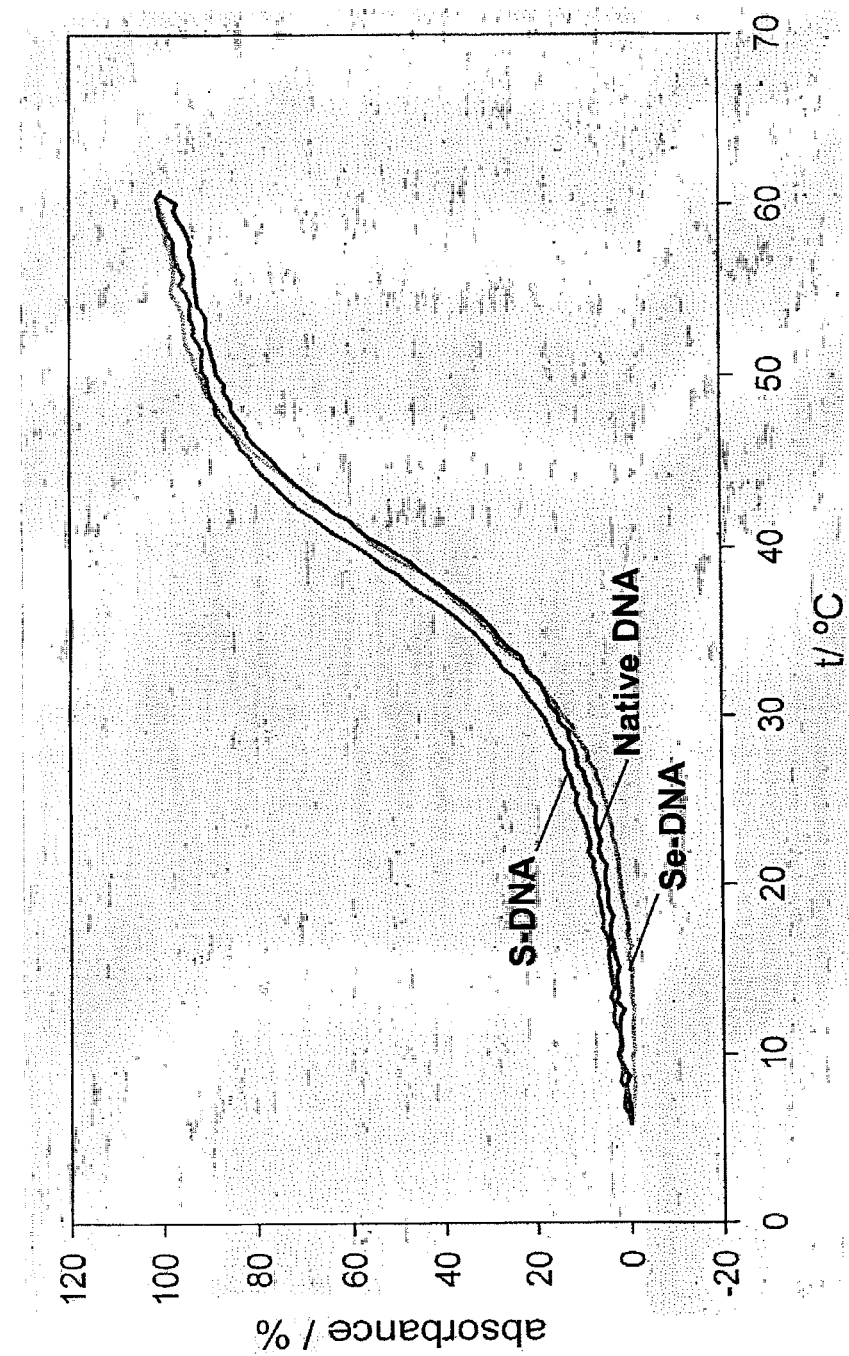
FIG. 12. Normalized UV-melting curves of the native and corresponding modified DNA duplexes that were modified according to two forms of the disclosure. The native DNA curve: the native DNA duplex (5'-ATGGTGCTC-3' and 3'-TACCACGAG-5', $T_m$=40.3° C.); the S-DNA curve: the S-modified duplex (5'-ATGG$^{5-S}$TGCTC-3' and 3'-TACCACGAG-5', $T_m$=37.9° C.), the Se-DNA curve: the Se-modified duplex (5'-ATGG$^{5-Se}$TGCTC-3' and 3'-TACCACGAG-5', $T_m$=39.3° C.).

FIG. 12 shows the normalized UV-melting curves of the native and corresponding modified DNA duplexes. In FIG. 12, the native curve of DNA duplex (5'-ATGGTGCTC-3' and 3'-TACCACGAG-5', $T_m$=40.3° C.), the curve of the S-modified duplex (5'-ATGG$^{5-S}$TGCTC-3' and 3'-TACCACGAG-5', $T_m$=37.9° C.), and the curve of the Se-modified duplex (5'-ATGG$^{5-Se}$TGCTC-3' and 3'-TACCACGAG-5', $T_m$=39.3° C.) are shown. The UV-melting data (Table 1) show that the melting temperature differences of the native and Se-modified DNA duplexes are small (less than ±1.0° C. per modification; see FIG. 12), whereas the S-modified (5-Me-S-T) DNA duplex is least stable (−3.0° C. per modification) [Ahmadian, M., Zhang, P. M. & Bergstrom, D. E. (1998) Nucleic Acids Research 26, 3127-3135]. In most cases, the native duplexes are slightly more stable than the Se-duplexes. The results suggest that the insertion of a Se atom at 5-exo-position [Jain, S., Zon, G. & Sundaralingam, M. (1989) Biochemistry 28, 2360-4] reveals that these two structures are virtually identical (FIG. 13), which is consistent with our UV-melting study. Moreover, the 5-Se-T and A form a base pair as well as the native T-A pair. The lengths of these two hydrogen bonds of the 5-SeT-A are 2.79 and 2.76 Å.

3. Investigation of C—H···O$^-$—PO$_3$ Interaction

In the structural comparison with the native structure, it was found that the Se insertion disrupts the weak 5-CH$_3$···π interaction [Umezawa, Y. & Nishio, M. (2002) Nucleic Acids Res 30, 2183-92] in the native structure [Jain, S., Zon, G. & Sundaralingam, M. (1989) Biochemistry 28, 2360-4], which results in slight reduction of the duplex stability. On the other hand, the intramolecular stacking slightly stabilizes the intermolecular interaction (the duplex stability) due to the possible pre-organization (slight entropy decrease of the Se-modified single strand before duplex formation). Therefore, the UV-melting observation on the slight stabilization or destabilization of the Se-DNA duplexes (±1.0° C. per modification) is consistent with these two conflicting interactions in the presence of the Se-modification. The negatively-charged oxide of the 5'-phosphate also orientates the 5-methyl group toward DNA backbone for the better interaction. In addition, our studies indicate that the Se-modification does not cause significant structure perturbation (FIG. 13), and that the 5-Se-T and A form a base pair as well as the native T-A pair.

To summarize, the experimental results have revealed that the Se-modification does not cause significant perturbation of the native DNA structure. The constant methylation on thymine in DNA may contribute to duplex flexibility and dynamic unwinding through the 5-methyl hydrogen-bonding switching between the 5'-preceding nucleobase and 5"-phosphate. Moreover, an atomic-level interaction mechanism of the phosphorylation and dephosphorylation may be common strategies in modulation of cellular signal transduction pathways [Su, X. D., Taddei, N., Stefani, M., Ramponi, G. & Nordlund, P. (1994) Nature 370, 575-8; Yudushkin, I. A., Schleifenbaum, A., Kinkhabwala, A., Neel, B. G., Schultz, C. & Bastiaens, P. I. (2007) Science 315, 115-9]. The results have suggested a new research direction to design and develop nuclease-resistant DNAs and RNAs that function as antisense DNAs, siRNAs and microRNAs. Furthermore, this selenium derivatization has great potential in the determination of nucleic acid crystal structures via multiwavelength anomalous dispersion (MAD) or single-wavelength anomalous (SAD) phasing.

4. Nuclease Resistance of the Se-Derivatized Nucleic Acids (SeNA)

Figure 33:
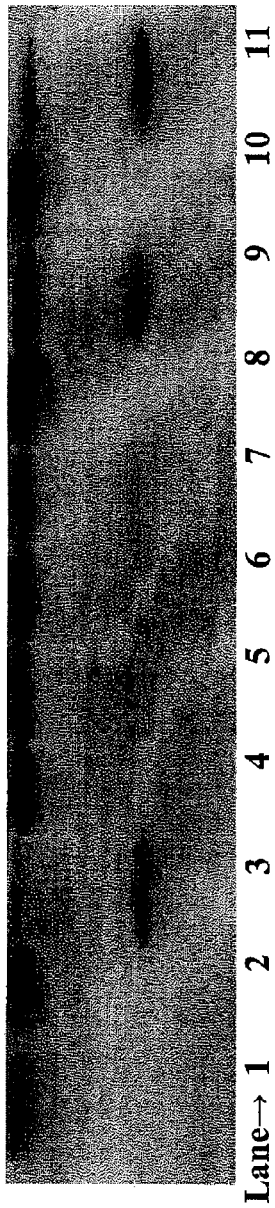
FIG. 33. Representation of the Se-DNA resistance to DNase (AseI) digestion according to some forms of the disclosure.
Figure 34:
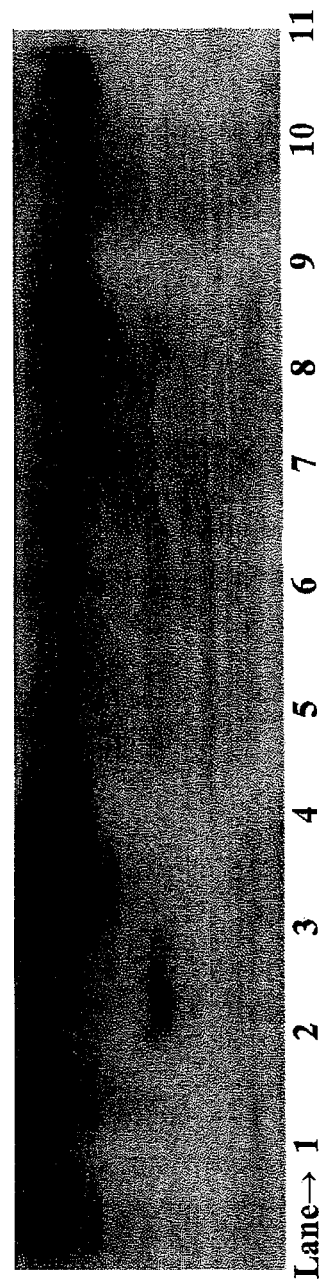
FIG. 34. Representation of the Se-DNA resistance to DNase (SalI) digestion according to some forms of the disclosure.
Figure 35:
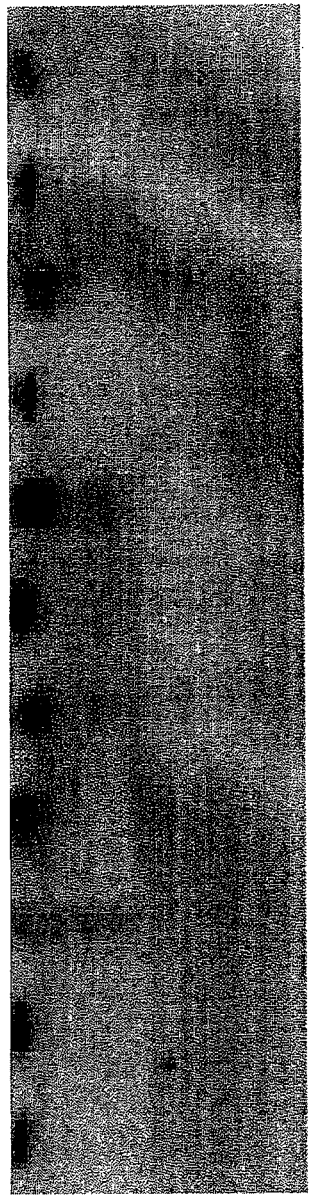
FIG. 35. Representation of the Se-DNA resistance to Exonuclease III digestion according to some forms of the disclosure.
Figure 36:
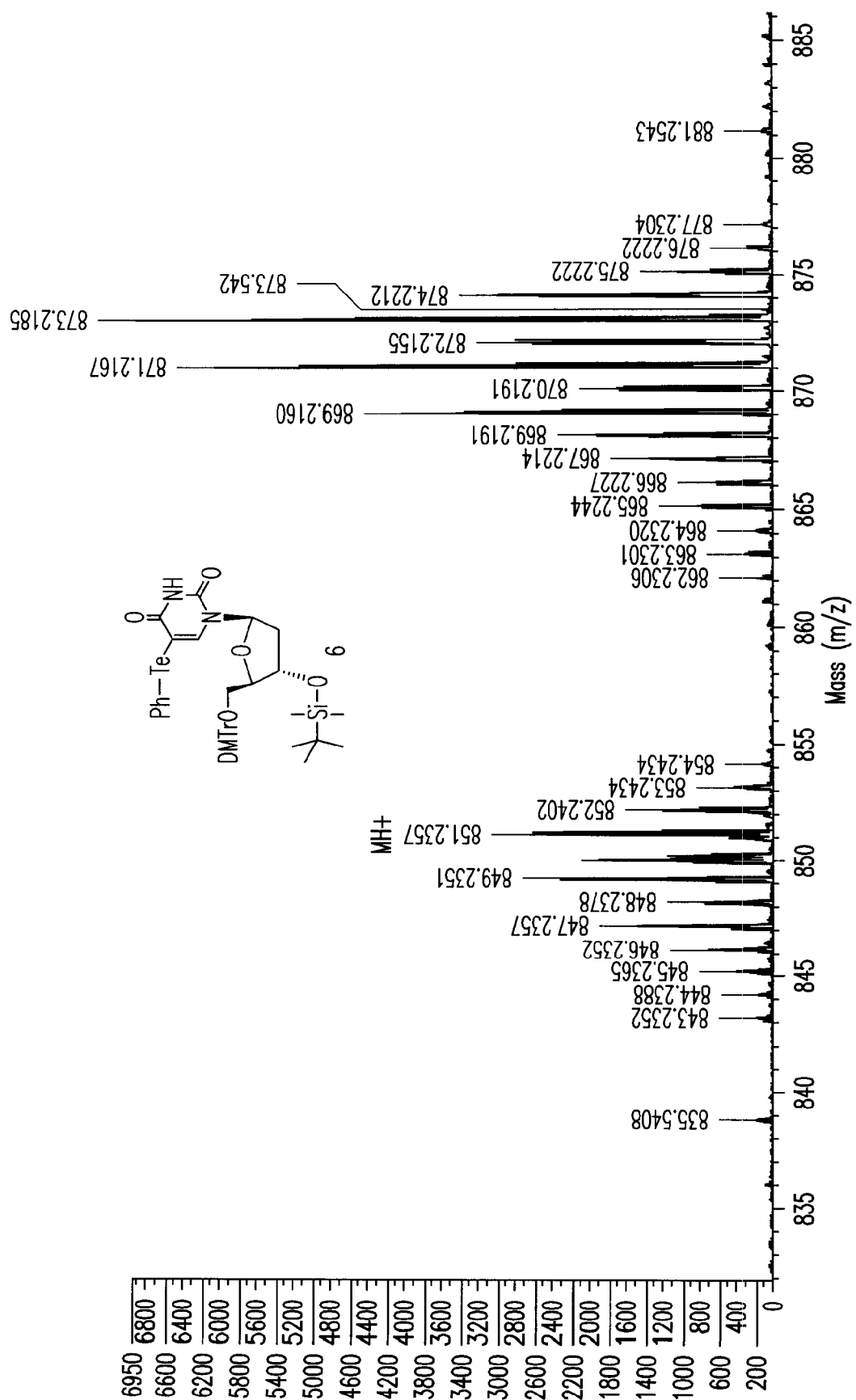
FIG. 36. Representation of the high resolution ESI-TOF spectrum of 3'-O-tert-butyldimethylsilyl-5'-O-(4,4-dimethoxytrityl)-2'-deoxy-5-phenyltellurouridine (6).
Figure 37A:
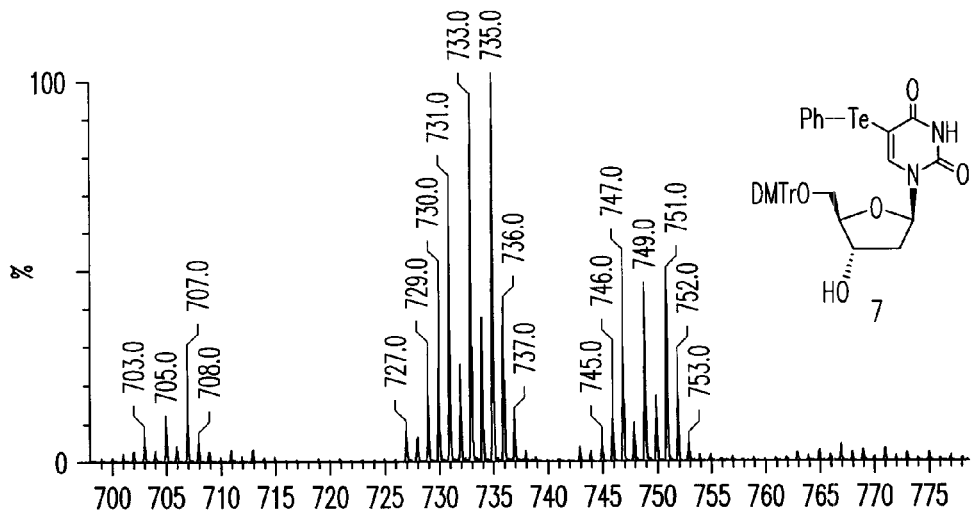
FIG. 37: Representation that (a) and (b) are low and high resolution ESI-MS spectra of 5'-O-(4,4-dimethoxytrityl)-2'-deoxy-5-phenyltellurouridine (7), respectively.
Figure 37B:
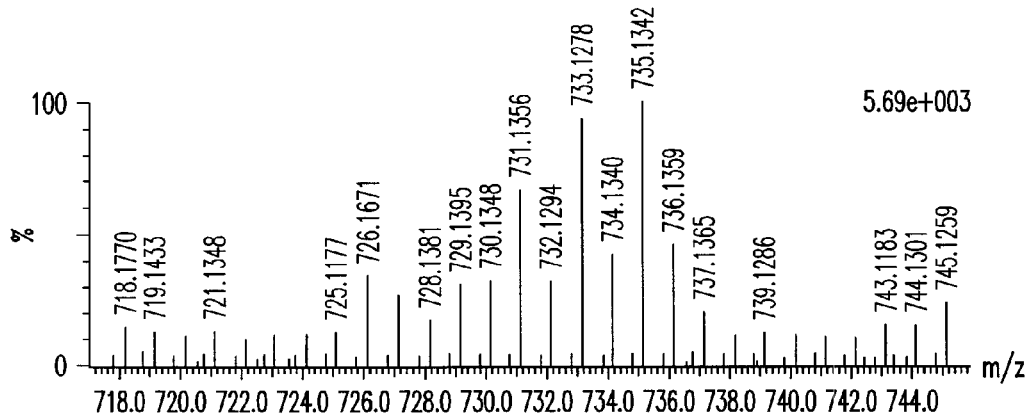
Figure 38A:
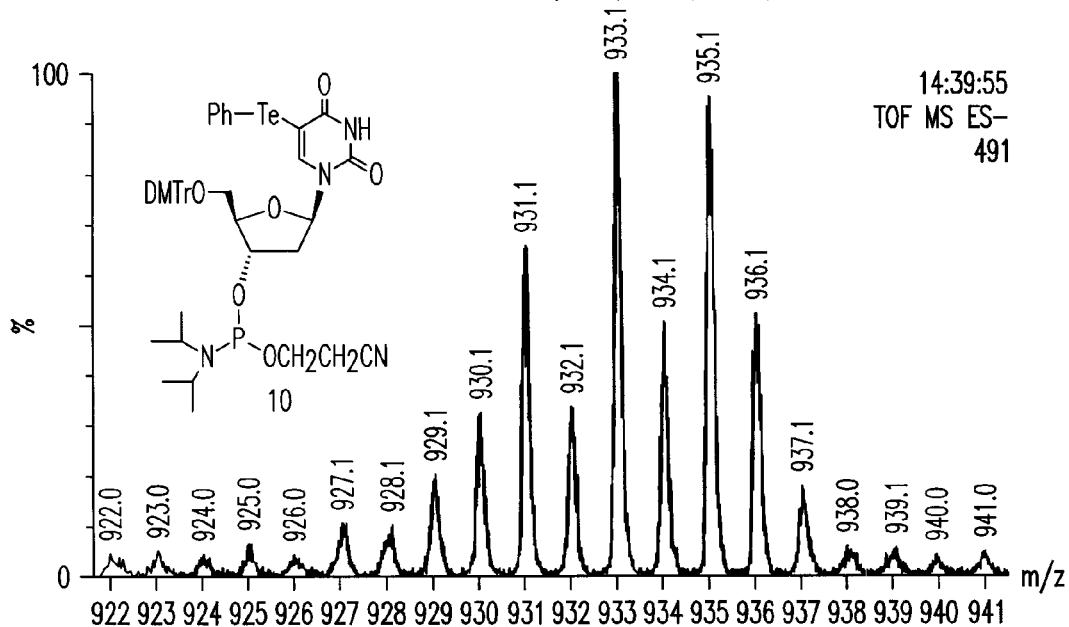
FIG. 38. Representation that (a) and (b) are low and high resolution ESI-MS spectra of phosphoramidite derivative 10, respectively.
Figure 38B:
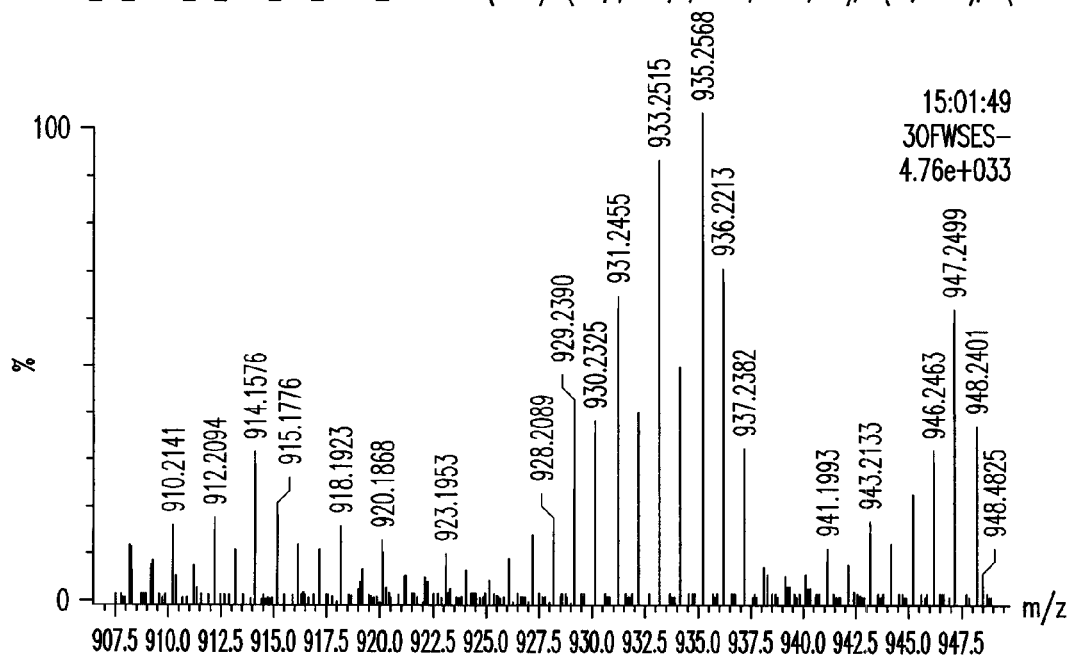
Figure 39:
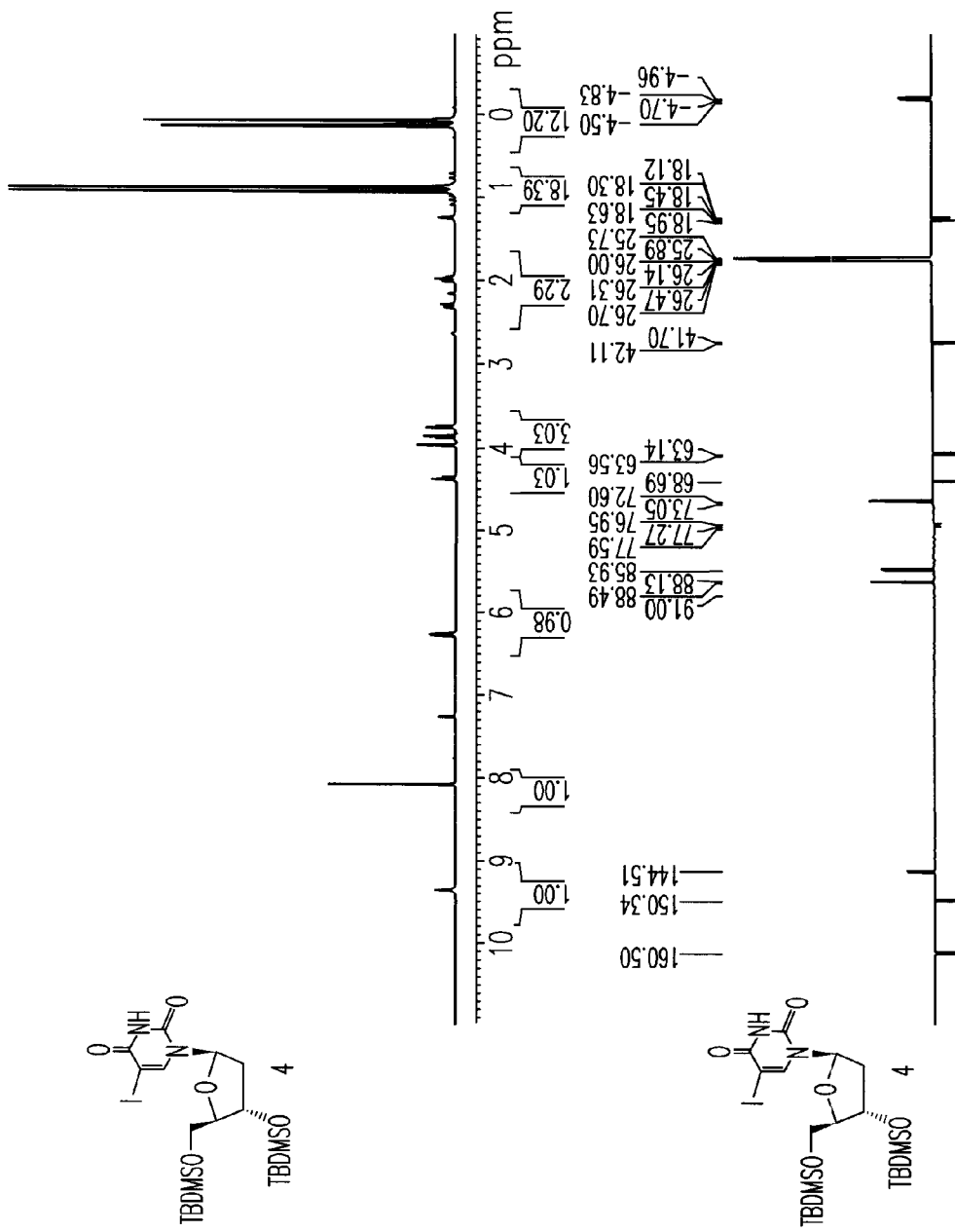
FIG. 39. $^1$H and $^{13}$C NMR spectra of 3',5'-Di-O-tert-butyldimethylsilyl-2'-deoxy-5-iodouridine (4).
Figure 40:
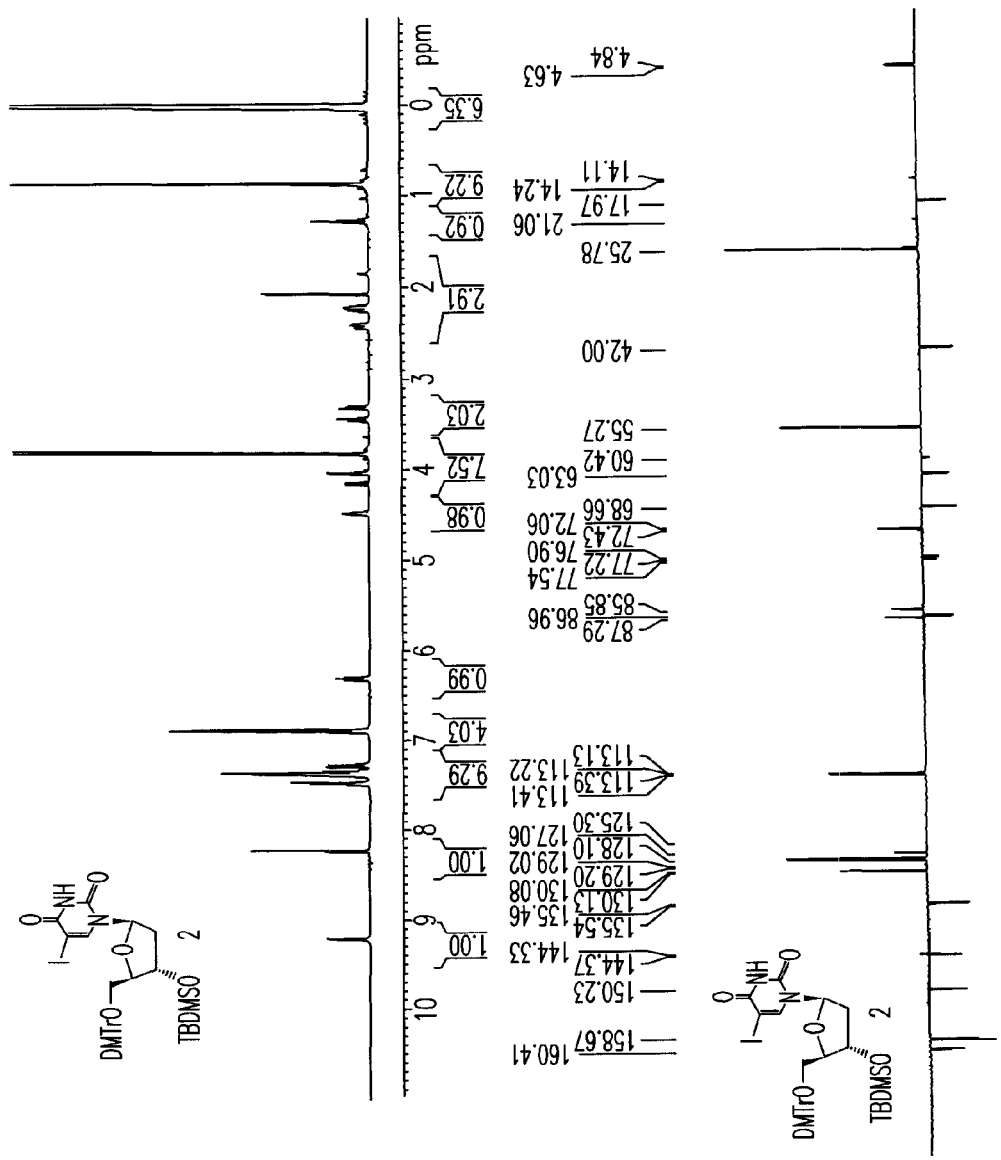
FIG. 40. $^1$H and $^{13}$C NMR spectra of 3'-O-tert-Butyldimethylsilyl-5'-O-(4,4-dimethoxytrityl)-2'-deoxy-5-iodouridine (2).
Figure 41:
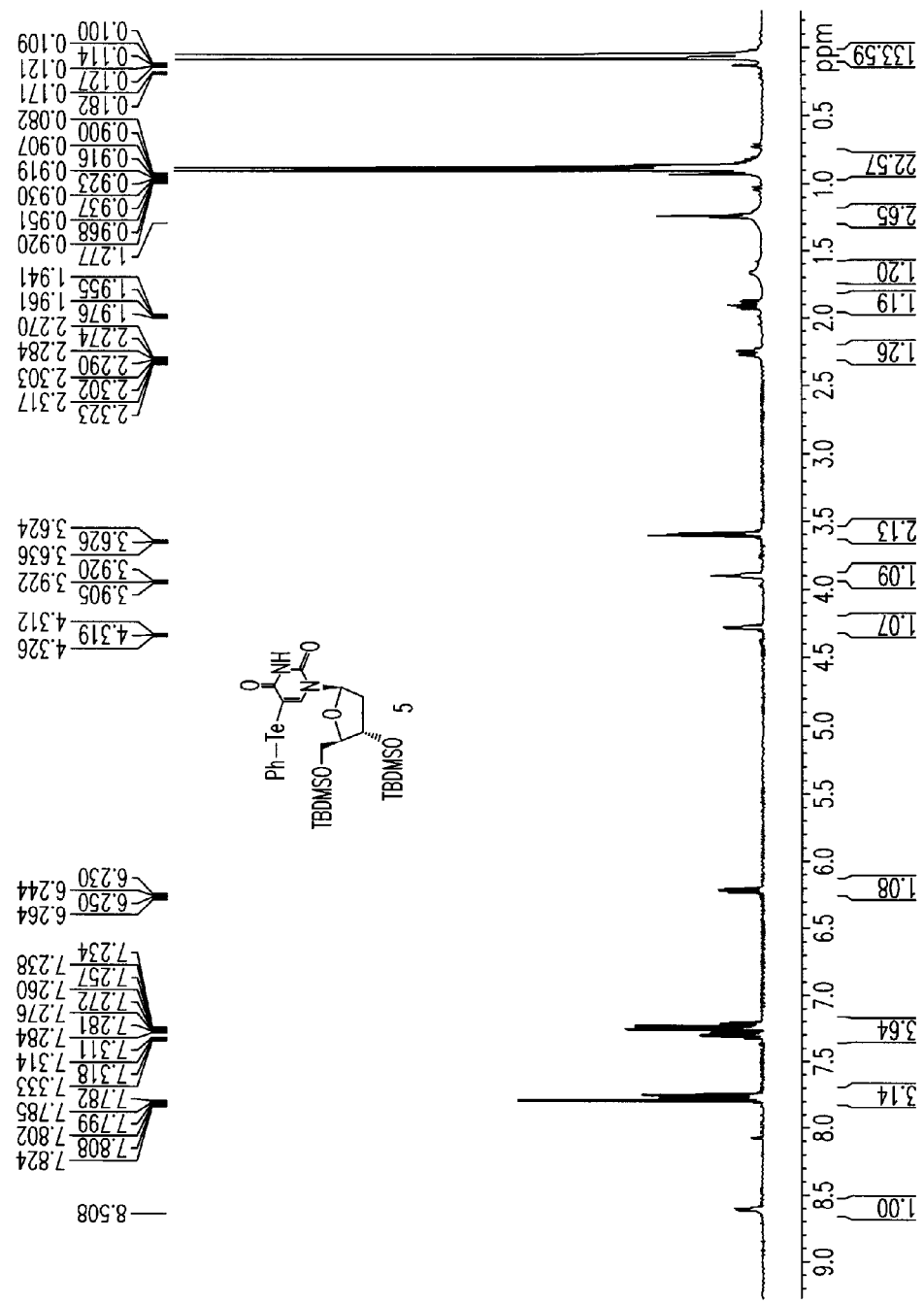
FIG. 41. $^1$H and $^{15}$C NMR spectrum of 3',5'-Di-O-tert-butyldimethylsilyl-2'-deoxy-5-phenyltellurouridine (5).
Figure 41:
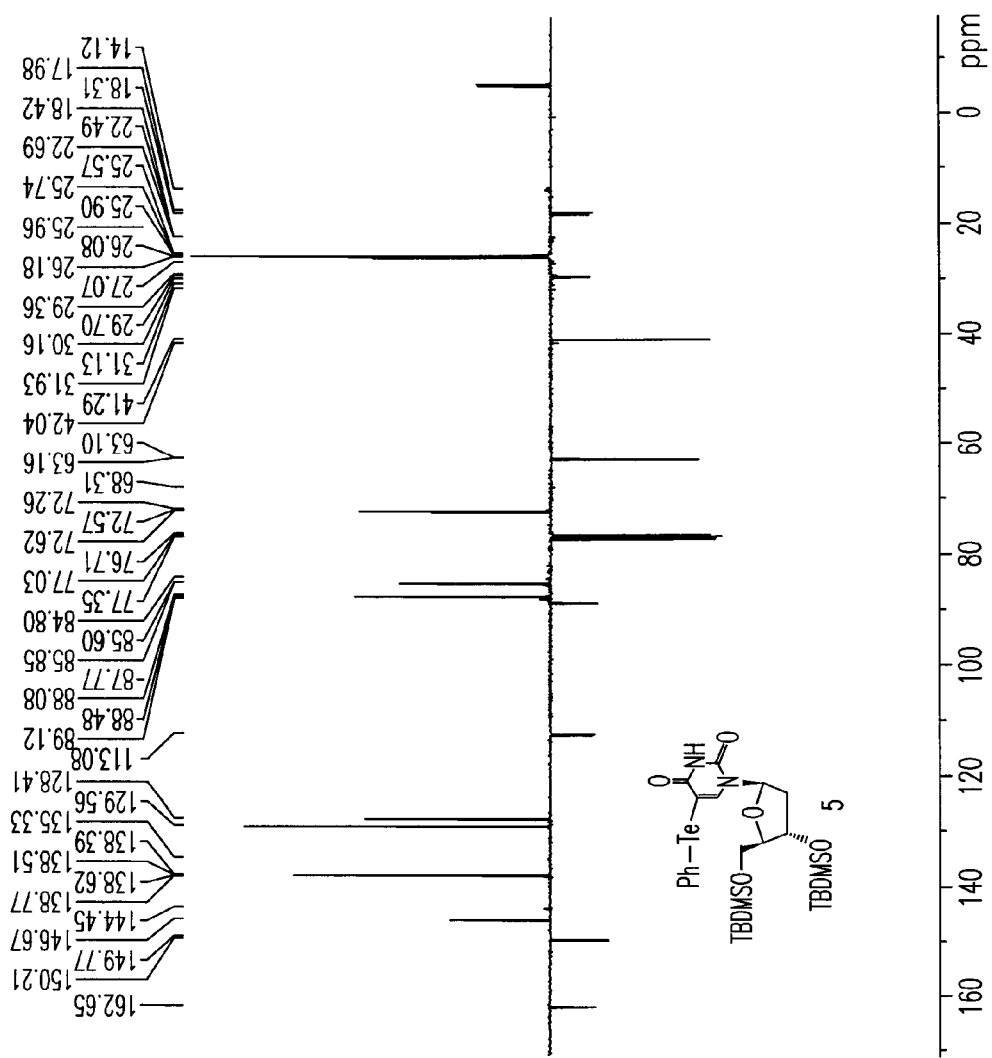
Figure 42:
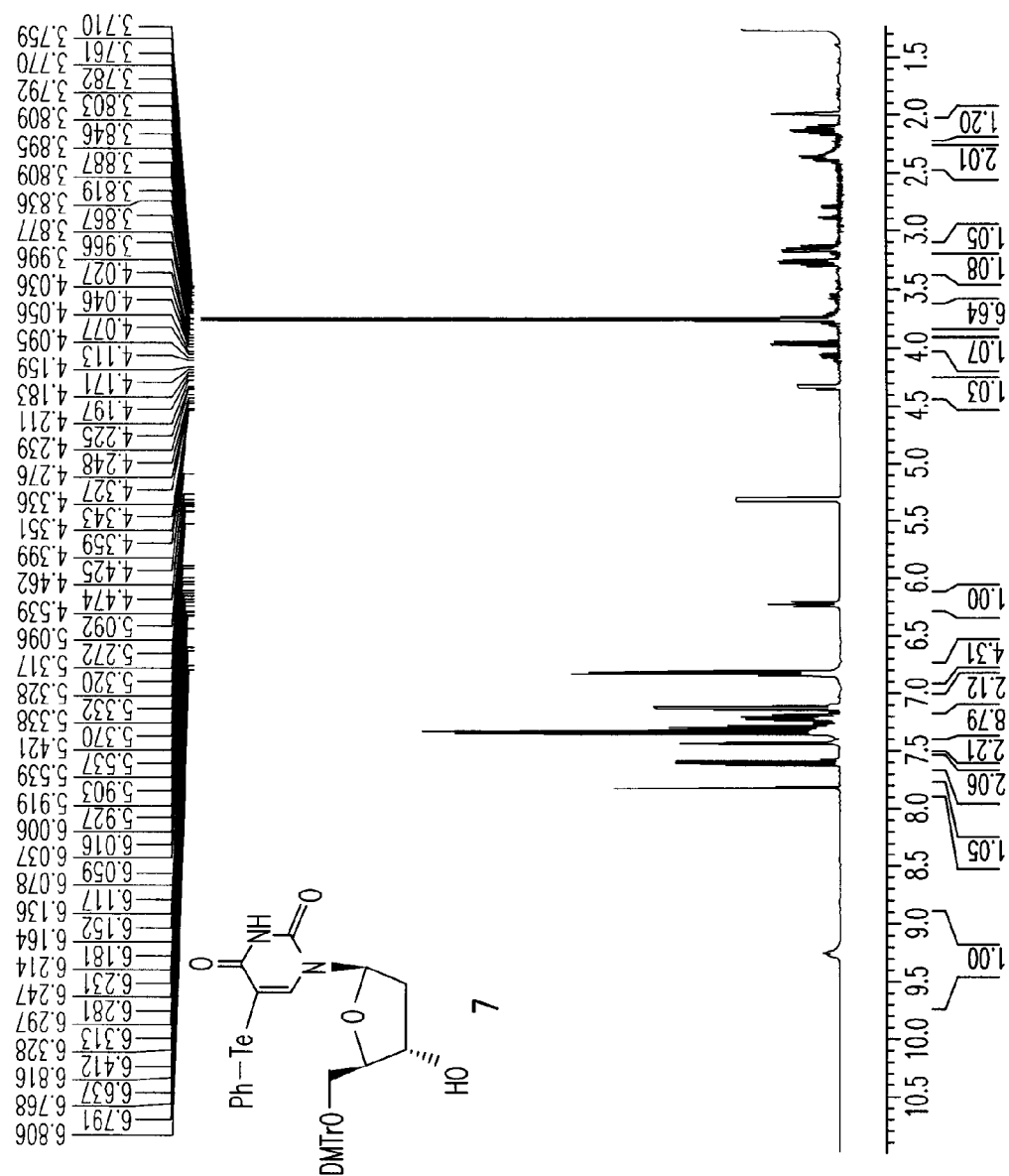
FIG. 42. $^1$H and $^{13}$C NMR spectrum of 5'-O-(4,4-dimethoxytrityl-2'-deoxy-5-phenyltellurouridine (7).
Figure 42:
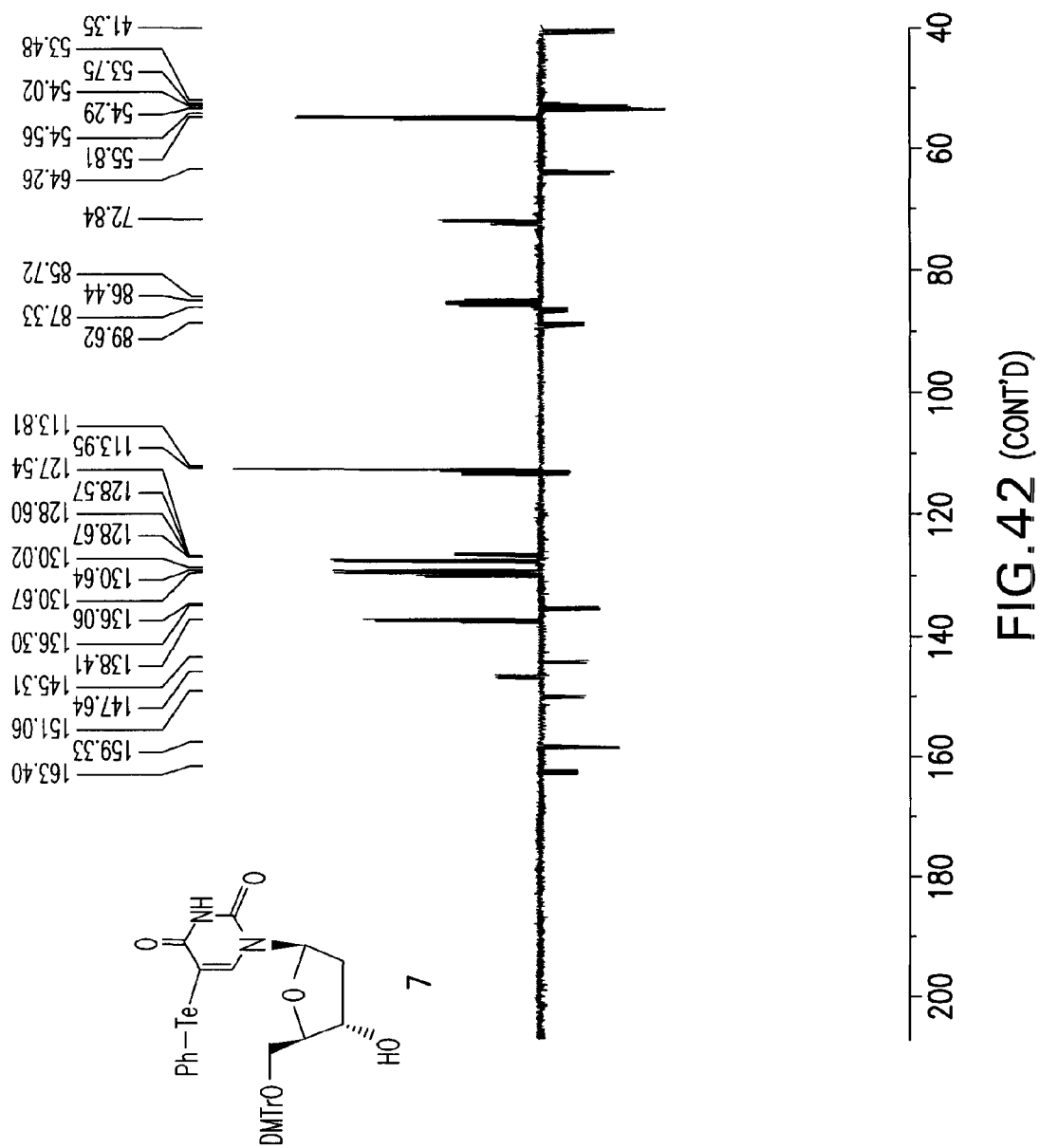
Figure 43:
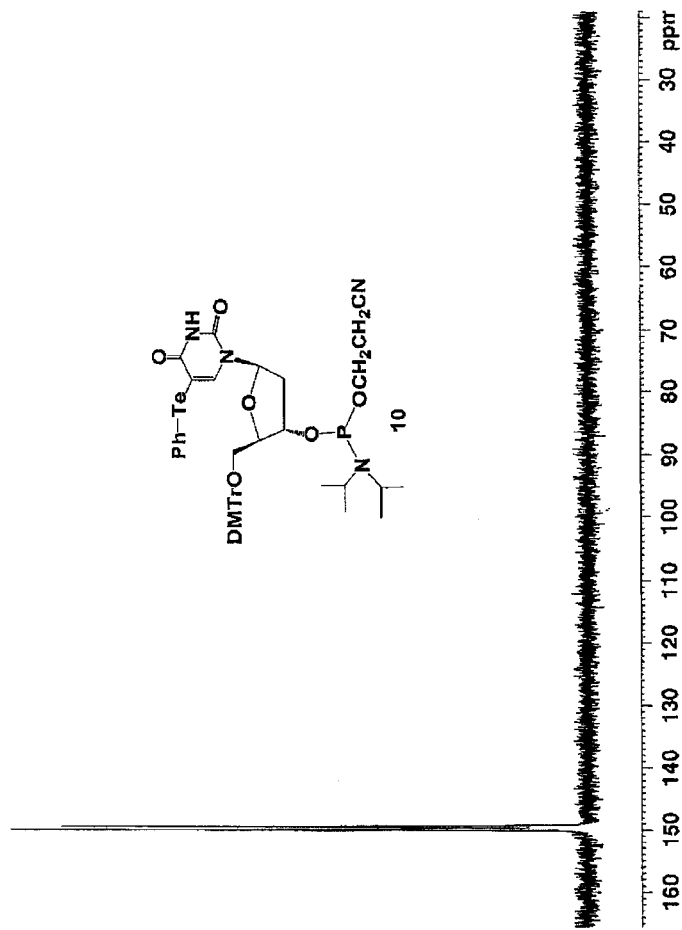
FIG. 43. $^{31}$P spectra of 1-[2'-deoxy-3'-O-(2-cyanoethyl-N,N-diisopropylamino)-phosphoramidite-5'-O-(4,4-dimethoxytrityl-β-D-erythro-ribofuranosyl]-5-phenyltellurouridine (10).

The nuclease resistance experiments shown in FIGS. 33-35 were performed using several enzymes under their standard digestion conditions. Several DNAs are designed for these nuclease-resistant experiments. They are DNA1: 5'-GTGCACTGATCAATTAATGTCGAC-3'; DNA2: 5'-GTGCACTGATCAA$\underline{T}$TAATGTCGAC-3'; DNA3: 5'-GTGCACTGATCAA$\underline{T}$TAATGTCGAC-3'; DNA4: 5'-GTGCACTGATCAATTAA$\underline{T}$GTCGAC-3'; DNA5: 5'-GTGCACTGATCAATTAATG$\underline{T}$CGAC-3'; DNA6: 5'-GTCGACATTAATTGATCAGTGCAC-3'; the underlined nucleotides are the 5-Se-thymidine. AseI, SalI, and Exonuclease III are examined for the nuclease resistance. The experimental results reveal that when the modification is in the enzymatic recognition sequences, the selenium-modified nucleic acids can completely inhibit the nuclease digestion reactions. When the modification is close to the recognition sequences, the selenium-modified nucleic acids show strong nuclease resistance.

FIG. 33 depicts the Se-DNAs resistant to DNase (MeI) digestion. Resistance of the 5-Se-T DNAs against DNase (AseI). In FIG. 33, DNA1: 5' GTGCACTGATCAATTAATGTCGAC-3'; DNA2: 5'-GTGCACTGATCAATTAATGTCGAC-3'; DNA3: 5'-GTGCACTGATCAAT$\underline{T}$AATGTCGAC-3'; DNA4: 5'-GTGCACTGATCAATTAA$\underline{T}$GTCGAC-3'; DNA5: 5'-GTGCACTGATCAATTAATG$\underline{T}$CGAC-3'; DNA6: 5'-GTCGACATTAATTGATCAGTGCAC-3'; wherein the underlined nucleotides above are the 5-Se-thymidine. Lane 1: DNA 1 as the control; Lane 2: DNA 1 and 6 incubated with the enzyme for 0 min; Lane 3: DNA 1 and 6 incubated with the enzyme for 16 hr, Lane 4: DNA 2 and 6 incubated with the enzyme for 0 min; Lane 5: DNA 2 and 6 incubated with the enzyme for 16 hr; Lane 6: DNA 3 and 6 incubated with the enzyme for 0 min; Lane 7: DNA 3 and 6 incubated with the enzyme for 16 hr; Lane 8: DNA 4 and 6 incubated with the enzyme for 0 min; Lane 9: DNA 4 and 6 incubated with the enzyme for 16 hr; Lane 10: DNA 5 and 6 incubated with the enzyme for 0 min; Lane 11: DNA 5 and 6 incubated with the enzyme for 16 hr.

FIG. 34 depicts resistance of certain Se-DNAs embodiments, particularly the 5-Se-T DNAs, against DNase (SalI) digestion. In FIG. 34, DNA1: 5'-GTGCACTGATCAATTAATGTCGAC-3'; DNA2: 5'-GTGCACTGATCAA$\underline{T}$TAATGTCGAC-3'; DNA3: 5'-GTGCACTGATCAAT$\underline{T}$AATGTCGAC-3'; DNA4: 5'-GTGCACTGATCAATTAA$\underline{T}$GTCGAC-3'; DNA5: 5'-GTGCACTGATCAATTAATG$\underline{T}$CGAC-3'; DNA6: 5'-GTCGACATTAATTGATCAGTGCAC-3'; the underlined nucleotides are the 5-Se-thymidine. Lane 1: DNA 1 as the control; Lane 2: DNA 1 and 6 incubated with the enzyme for 0 min; Lane 3: DNA 1 and 6 incubated with the enzyme for 16 hr, Lane 4: DNA 2 and 6 incubated with the enzyme for 0 min; Lane 5: DNA 2 and 6 incubated with the enzyme for 16 hr; Lane 6: DNA 3 and 6 incubated with the enzyme for 0 min; Lane 7: DNA 3 and 6 incubated with the enzyme for 16 hr; Lane 8: DNA 4 and 6 incubated with the enzyme for 0 min; Lane 9: DNA 4 and 6 incubated with the enzyme for 16 hr; Lane 10: DNA 5 and 6 incubated with the enzyme for 0 min; Lane 11: DNA 5 and 6 incubated with the enzyme for 16 hr.

FIG. 35 shows the Se-DNAs resistant to Exonuclease III digestion. In FIG. 35, resistance of the 5-Se-T DNAs against Exonuclease III. DNA1: 5'-GTGCACTGATCAATTAATGTCGAC-3'; DNA2: 5'-GTGCACTGATCAA$\underline{T}$TAATGTCGAC-3'; DNA3: 5'-GTGCACTGATCAAT$\underline{T}$AATGTCGAC-3'; DNA4: 5'-GTGCACTGATCAATTAA$\underline{T}$GTCGAC-3'; DNA5: 5'-GTGCACTGATCAATIAATG$\underline{T}$CGAC-3'; DNA6: 5'-GTCGACATTAATTGATCAGTGCAC-3% the underlined nucleotides are the 5-Se-thymidine. Lane 1: DNA 1 as the control; Lane 2: DNA 1 and 6 incubated with the enzyme for 0 min; Lane 3: DNA 1 and 6 incubated with the enzyme for 15 min; Lane 4: DNA 2 and 6 incubated with the enzyme for 0 min; Lane 5: DNA 2 and 6 incubated with the enzyme for 15 min; Lane 6: DNA 3 and 6 incubated with the enzyme for 0 min; Lane 7: DNA 3 and 6 incubated with the enzyme for 15 min; Lane 8: DNA 4 and 6 incubated with the enzyme for 0 min; Lane 9: DNA 4 and 6 incubated with the enzyme for 15 min; Lane 10: DNA 5 and 6 incubated with the enzyme for 0 min; Lane 11: DNA 5 and 6 incubated with the enzyme for 15 min.

5. UV-Melting Temperature Experiments

Figure 15:
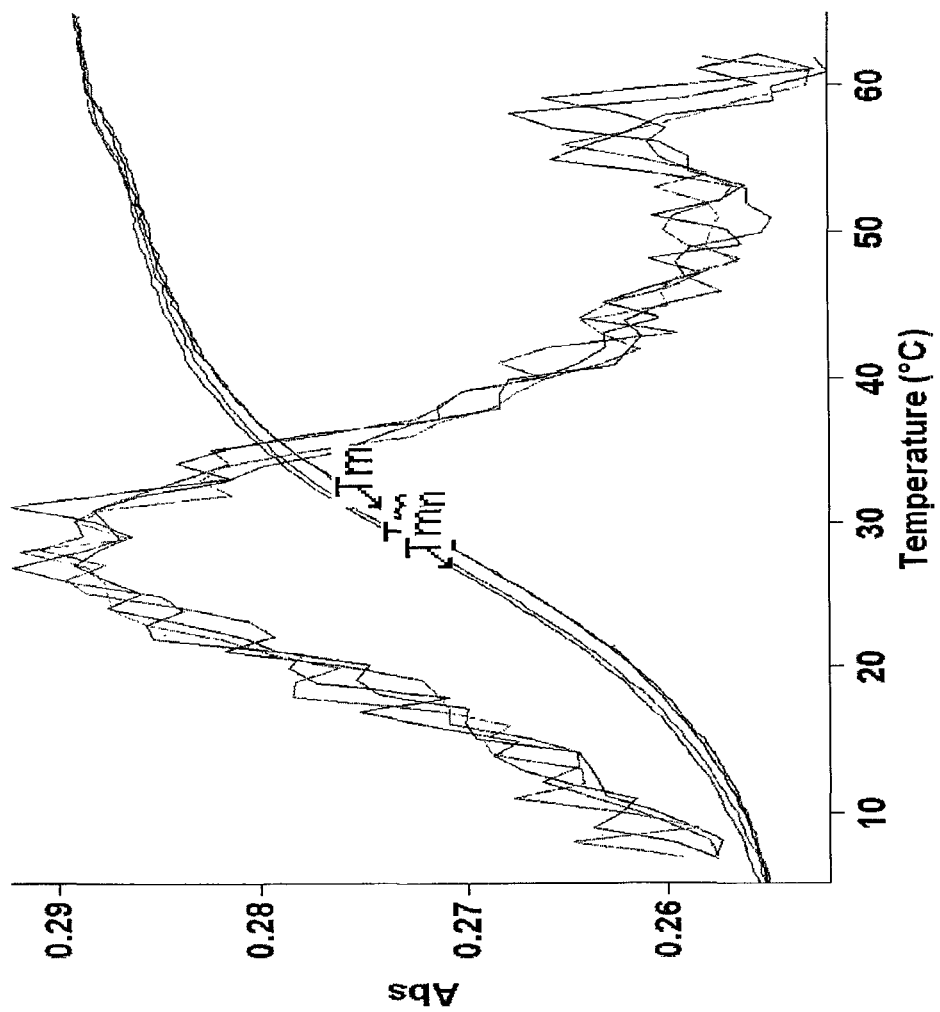
FIG. 15. UV melting curve of DNA according to the disclosure. The corresponding Se-DNA (5'-G-$^{5-So}$T-GTACAC-3'), $T_m$=27.9° C., according to an embodiment of the disclosure that corresponds to the DNA with a UV melting curve shown in FIG. 14.

The experiments were performed using the samples (2 µM DNA duplexes) dissolved in the buffer of 50 mM NaCl, 10 mM $Na_2H2PO_4$—$Na_2HPO_4$ (pH 6.5), 0.1 mM EDTA and 10 mM $MgCl_2$. The samples were heated to 60° C. and allowed to cool down to room temperature slowly. These experiments were carried out by Cary 300 UV-Visible Spectrophotometer with a temperature controller at a heating rate of 0.5° C./min. Typical denaturing curves are shown in FIG. 12 and FIGS. 15A and 15B.

6. Crystallization, Structure Determination and Refinement of the Se-DNA Containing 5-SeMe-dU The 2'-Deoxy-2'-methylselenyluridine moiety ($dU_{2'-SeMe}$) was used to facilitate the crystal growth of the Se-DNA (5'-G-$dU_{2'-Se}$-G-$^{5-Se}$T-ACAC-3', self-complementary) using Nucleic Acid Mini Screen kit (Hampton Research, with 24 diversified crystallization buffers). The crystals grown in buffer #7 [10% (v/v) MPD, 12 mM Spermine tetra-HCl (pH 6.0), 80 mM NaCl, 20 mM $MgCl_2$] were used for diffraction data collection.

7. Diffraction Data Collection

X-ray data were collected at beam line X12C in NSLS of Brookhaven National Laboratory. A number of crystals were scanned to find the one with strong anomalous scattering at the K-edge absorption of selenium. 25% glycerol was used as cryoprotectant while data collection was taken under the liquid nitrogen stream at 99° K. The chosen wavelengths for selenium MAD data are 0.9797, 0.9795, and 0.9400 angstroms. The crystal was exposed 10 seconds per image after one degree rotation, and a total of 180 images were taken for each data set. The additional reference data sets were collected at 1.10 Å wavelength and were used for the final structure refinement. All data were processed using HKL2000 and DENZO/SCALEPACK.

8. Structure Determination and Refinement

Figure 14:
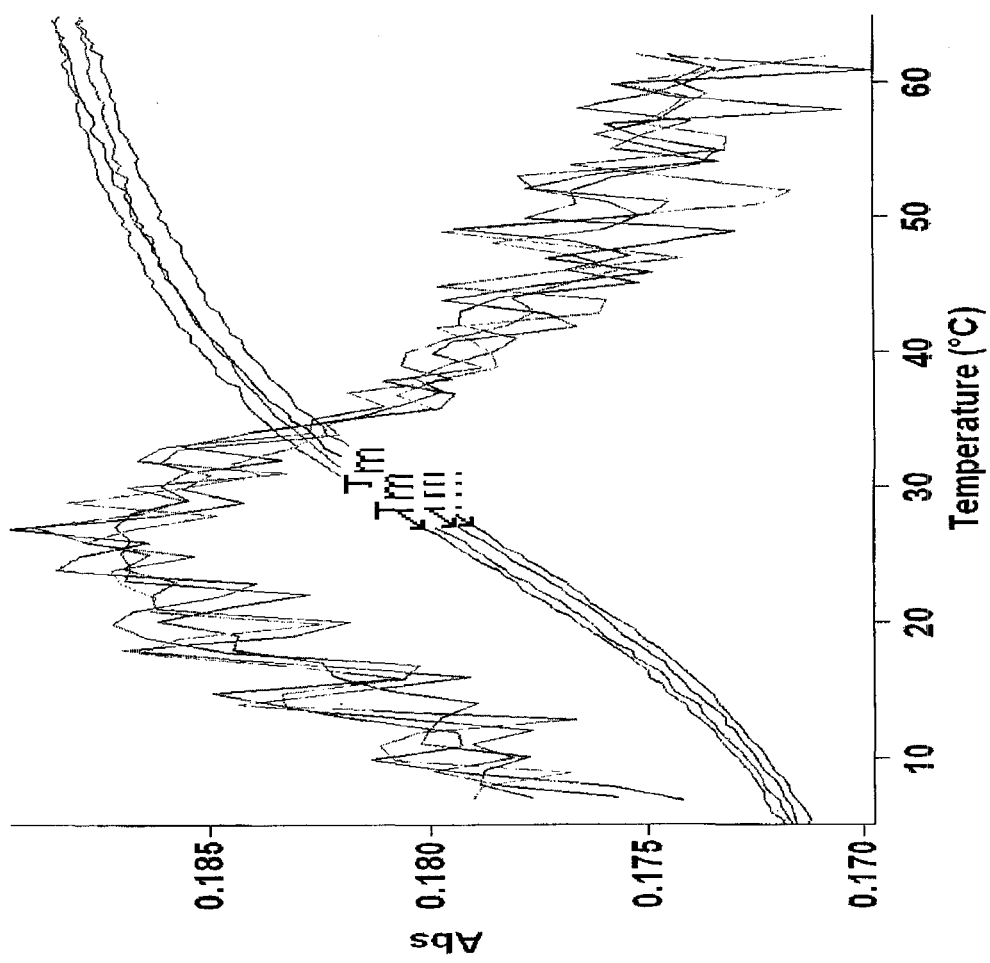
FIG. 14. UV melting curve of the native self-complementary DNA (5'-GTGTACAC-3'), $T_m$=27.5° C.

The two positions of the selenium atoms were identified by the heavy atom search scripts provided by CNS (Brunger, at al., 1998). Following the refinement of the selenium positions, the experimental phases were calculated and extended using the MAD phasing procedures in CNS. The initial phased maps were then improved by the solvent flattening and density modification procedure. The model of single strand of DNA was manually built into the electron density map using O (Jones, 1991), and then the refinement was carried out. The refinement protocol includes simulated annealing, positional refinement, restrained B-factor refinement, and bulk solvent correction. The topologies and parameters for UMS with the selenium at the 2'-position and the modified T (T5S) with the selenium at the 5-position were constructed and applied. After several cycles of refinements and the model rebuilding, a number of highly ordered waters were added. The two selenium atoms are fully occupied. Cross-validation with a 10% test set was monitored during the refinement. The $\sigma_A$-weighted maps of the (2m|Fo|−D|Fc|) and the difference (m|Fo|−D|Fc|) density maps were computed and used throughout the model building. The final R/R-free values are 0.210/0.226 with 28 waters (Table 4 and 5). The Se-modified duplex and single-stand structures are presented in FIG. 14.

TABLE 4

Data collection and Statistics

| Wavelength, Å | 1.1000 |
|---|---|
| Resolution range, Å | 50.0-1.8 |
| (last shell) | (1.86-1.80) |
| Unique reflections | 2087 (209) |
| Completeness, % | 94.9 (99.5) |
| $R_{merge}$, % | 12.9 (44.1) |
| <I/σ(I)> | 10.5 (9.9) |
| Redundancy | 9.7 (8.2) |

TABLE 5

Structure Refinement and Model Statistics

| Structure (PDB ID) | 5-Se-T-DNA(3BM0) |
|---|---|
| Space Group | P4(3)2(1)2 |
| Cell dimensions: a, b, c (Å) | 41.894, 41.894, 23.739 |
| Resolution range, Å | 15.76-1.80 |
| (last shell) | (1.91-1.80) |
| $R_{work}$, % | 21.0 (21.4) |
| $R_{free}$, % | 22.6 (25.2) |
| Number of reflections | 1922 (98) |
| Number of atoms | |
| Nucleic Acid | 161 |
| Heavy Atoms and Ion | 2 Se |
| Water | 28 |
| R.m.s. deviations | |
| Bond length, Å | 0.009 |
| Bond angle, | 1.9 |

TABLE 5-continued

Structure Refinement and Model Statistics

| Structure (PDB ID) | 5-Se-T-DNA(3BM0) |
|---|---|
| Average B-factors, Å$^2$ | |
| All atoms | 33.9 |
| Wilson plot | 25.2 |
| Overall anisotropic B-values | |
| B11/B22/B33/ | −1.91/−1.92/3.84 |
| Bulk solvent correction | |
| Solvent density, e/Å$^3$ | 0.45 |
| B-factors, Å$^2$ | 67.3 |
| Coordinates error (c.-v.), 5 Å | |
| Esd. from Luzzatt plot, Å | 0.19 |
| Esd. from SIGMAA, Å | 0.25 |

9. Testing of Te-Oligonucleotides and Te-DNAs

Figure 48:
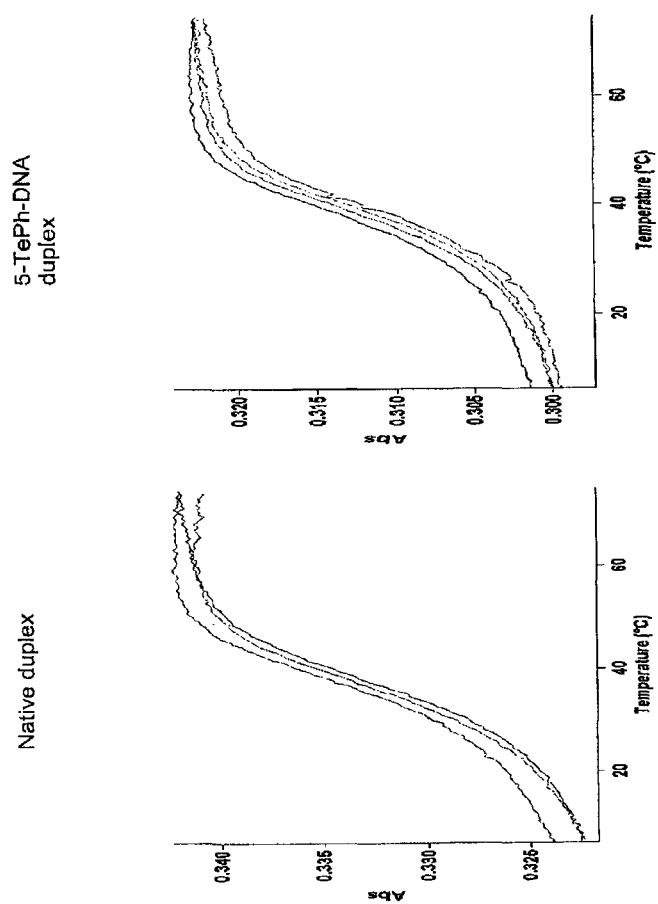
FIG. 48. UV-melting curves of the native and 5-TePh-DNA duplexes: 5'-ATGG(5-TePh-T)GCTC-3' & 3'-TACCAC-GAG-5'
Figure 49:
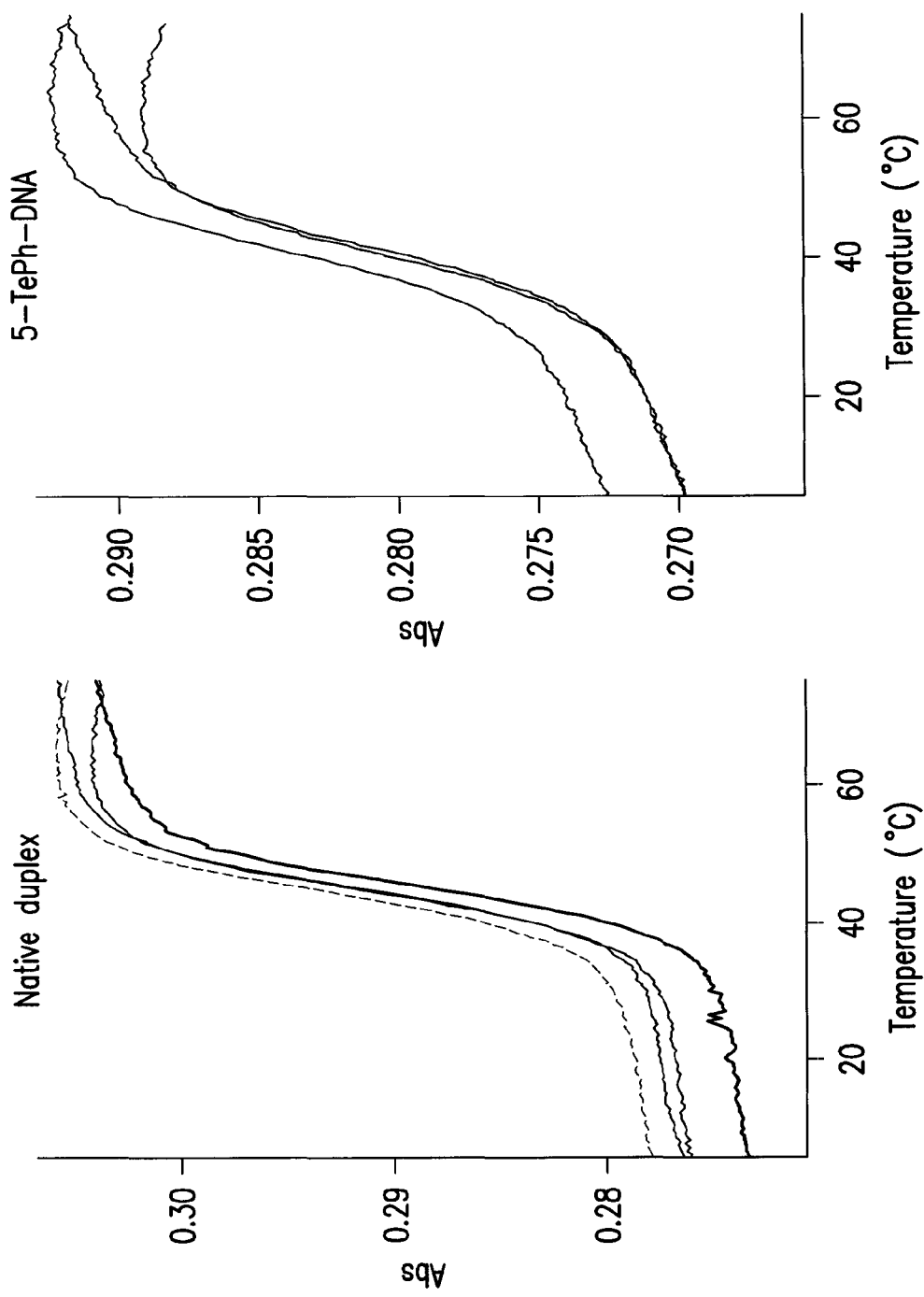
FIG. 49. UV-melting curves of the native and 5-TePh-DNA duplexes: 5'-CT(5-TePh-T)TCTTGTCCG-3' & 5'-CGGA-CAAGAAG-3'
Figure 50:
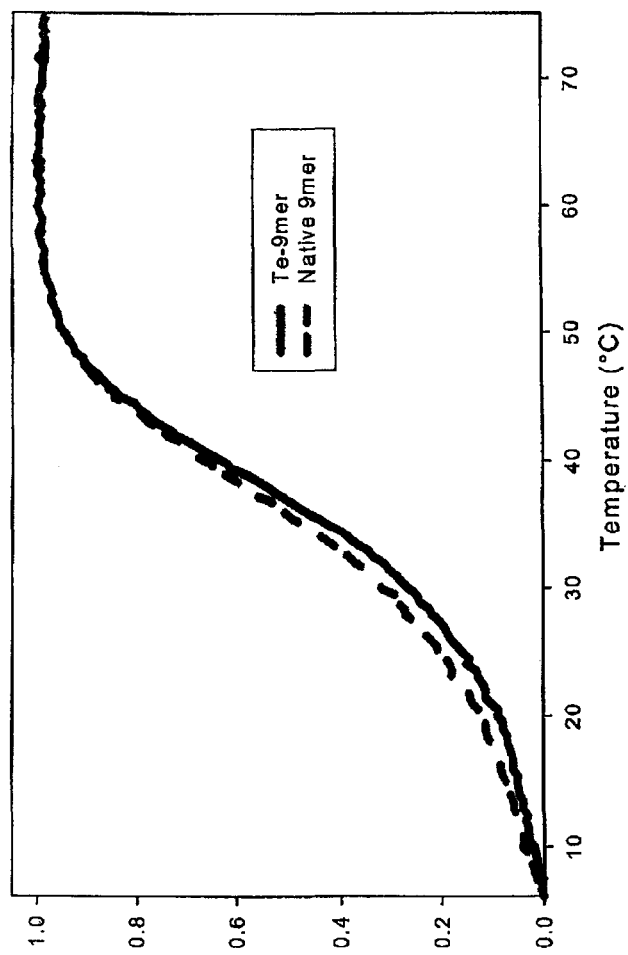
FIG. 50. Normalized thermal-denaturation curves of the native and Te-modified DNA duplexes. The Te-DNA duplex: 5'-ATGG(5-TePh-T)GCTC-3' and 5'-GAGCACCAT-3'. The blue and red curves represent the Te-modified and the corresponding native duplexes with 40.3±0.2° C. and 39.8±0.3° C. as their melting temperatures, respectively.
Figure 51:
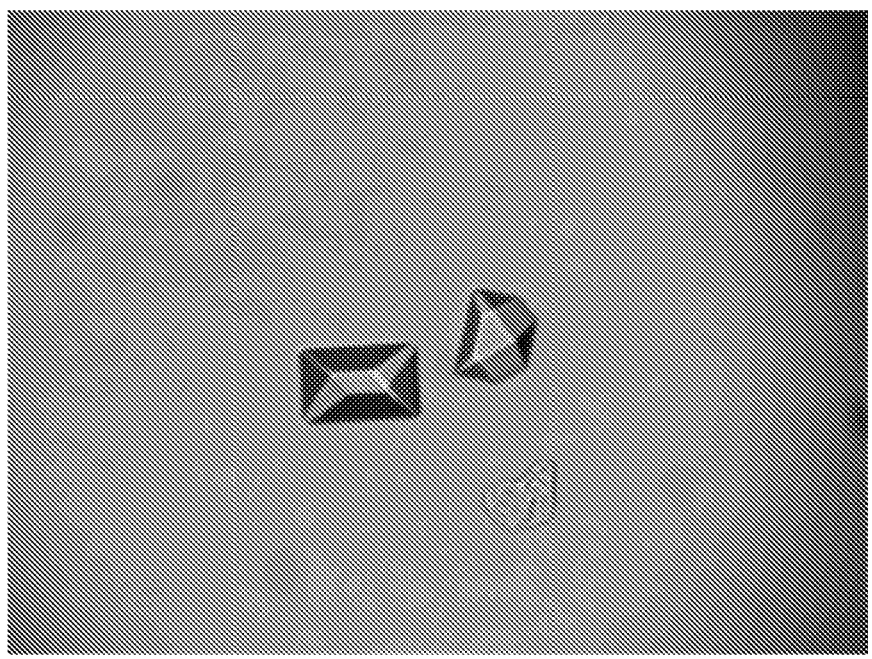
FIG. 51. Photos of Se—Te derivatized DNA octomer crystals.

Thermodenaturization of duplex DNAs: Solutions of the duplex DNAs (2 μM) were prepared by dissolving the DNAs in a buffer containing NaCl (50 mM), sodium phosphate (10 mM, pH 7.2), EDTA (0.1 mM) and MgCl$_2$ (10 mM). The solutions were then heated to 80° C. for 3 min, cooled slowly to room temperature, and stored at 4° C. overnight before measurement. Prior to thermal denaturation, argon was bubbled through the samples. Each denaturizing curves were acquired at 260 nm by heating and cooling for four times in a rate of 0.5° C./min using Cary-300 UV-Visible spectrometer equipped with temperature controller system. See FIGS. 48-50.

Crystallization: The purified oligonucleotides (1 mM) were heated to 70° C. for 2 minute, and cooled slowly to room temperature. Both native buffer and Nucleic Acid Mini Screen Kit (Hampton Research) were applied to screen the crystallization conditions with 1 mM of DNA sample at different temperatures using the hanging drop method by vapor diffusion.

Data Collection: 30% glycerol, PEG 400 or the perfluoropolyether was used as a cryoprotectant during the crystal mounting, and data collection was taken wader the liquid nitrogen stream at 99° K. The Te-DNA-8mer crystal data were collected at beam line X12C in NSLS of Brookhaven National Laboratory. A number of crystals were scanned to find the one with strong anomalous scattering at the K-edge absorption of selenium. The distance of the detector to the crystals was set to 150 mm. The wavelengths of 0.9795 Å was chosen for selenium SAD phasing. The crystals were exposed for 10 to 15 seconds per image with one degree oscillation, and a total of 180 images were taken for each data set. All the data (Table 6) were processed using HKL2000 and DENZO/SCALEPACK [Z. Otwinowski, W. Minor, *Meth. Enzymol.* 1997, 276, 307-326].

TABLE 6

X-ray data collection: the data collected at selenium K-edge (12.66 keV)

| Data Collection | λ = 0.9795 Å |
|---|---|
| Resolution range, Å (last shell) | 18.89-1.50 (1.55-1.50) |
| Unique reflections | 3659 |
| Completeness, % | 94.4 |
| $R_{merge}$, % | 7.5 (42.7) |
| <I/σ(I)> | 14.9 (2.4) |

TABLE 6-continued

X-ray data collection: the data collected at selenium K-edge (12.66 keV)

| Data Collection | $\lambda = 0.9795$ Å |
|---|---|
| Redundancy | 8.63 (5.30) |
| Reduced ChiSquared | 0.93 (0.42) |

$R_{merge} = \Sigma |I - <I>|/\Sigma I$

Structure Determination and Refinement: The crystal structure of this Se—Te-8mer was solved (Table 7) by molecular replacement with Phaser [A. J. McCoy, R. W. Grosse-Kunstleve, P. D. Adams, M. D. Winn, L. C. Storoni, R. J. Read, *J. Appl. Cryst.* 2007, 40, 658-674], followed by the refinement of selenium and tellurium atom positions in both CNS [A. T. Bringer, P. D. Adams, G. M. Clore, W. L. DeLano, P. Gros, R. W. Grosse-Kunstleve, J. S. Jiang, J. Kuszewski, M. Nilges, N. S. Pannu, R. J. Read, L. M. Rice, T. Simonson, G. L. Warren, *Acta. Cryst. D. Biol. Cryst.* 1998, 54, 905-921] and Refmac [G. N. Murshudov, A. A. Vagin, E. J. Dodson, *Acta. Cryst. D. Biol. Cryst.* 1997, 53, 240-255]. The refinement protocol includes simulated annealing, positional refinement, restrained B-factor refinement, and bulk solvent correction. The stereo-chemical topology and geometrical restrain parameters of DNA/RNA [G. Parkinson, J. Vojtechovsky, L. Clowney, A. T. Brunger, H. M. Berman, *Acta. Cryst. D. Biol. Crysta.* 1996, 52, 57-64] have been applied. The topologies and parameters for modified dU with 2'-SeMe (UMS) and 5-tellurium (TTE) were constructed and applied. After several cycles of refinement, a number of highly ordered waters were added. Final, the occupancies of selenium and tellurium were adjusted. Cross-validation [A. T. Brunger, *Nature* 1992, 355, 472-475] with a 5-10% test set was monitored during the refinement. The (TA-weighted maps [R. J. Read, *Acta. Cryst. A.* 1986, 42, 140-149] of the (2m|Fo|−D|Fc|) and the difference (m|Fo|−D|Fc|) density maps were computed and used throughout the model building.

TABLE 7

Refinement statistics for the Te-DNA-8mer by molecular replacement

| Refinement | PDB ID: 3FA1 |
|---|---|
| Resolution range, Å (last shell) | 25-1.50 (1.55-1.5) |
| Number of reflections | 6859 (424) |
| $R_{work}$, % | 19.3 |
| $R_{free}$, % | 21.5 |
| Number of atoms | |
| Nucleic Acid (single) | 162 |
| Heavy atom | 2 (Te, Se) |
| Water | 28 |
| R.m.s. deviations | |
| Bond length, Å | 0.010 |
| Bond angle, | 1.73 |
| Average B-factors, Å | |
| All atoms | 22.3 |
| Wilson plot | 19.6 |
| Overall anisotropic B-values | |
| B11/B22/B33 | 0.6/0.6/−1.2 |
| Bulk solvent correction | |
| Solvent density, e/Å$^3$ | 0.44 |
| B-factors, Å$^2$ | 59.6 |

TABLE 7-continued

Refinement statistics for the Te-DNA-8mer by molecular replacement

| Refinement | PDB ID: 3FA1 |
|---|---|
| Coordinates error (c.-v.), 5 Å | |
| Esd. from Luzzatt plot, Å | 0.17 |
| Esd. from SIGMAA, Å | 0.15 |

Figure 53:
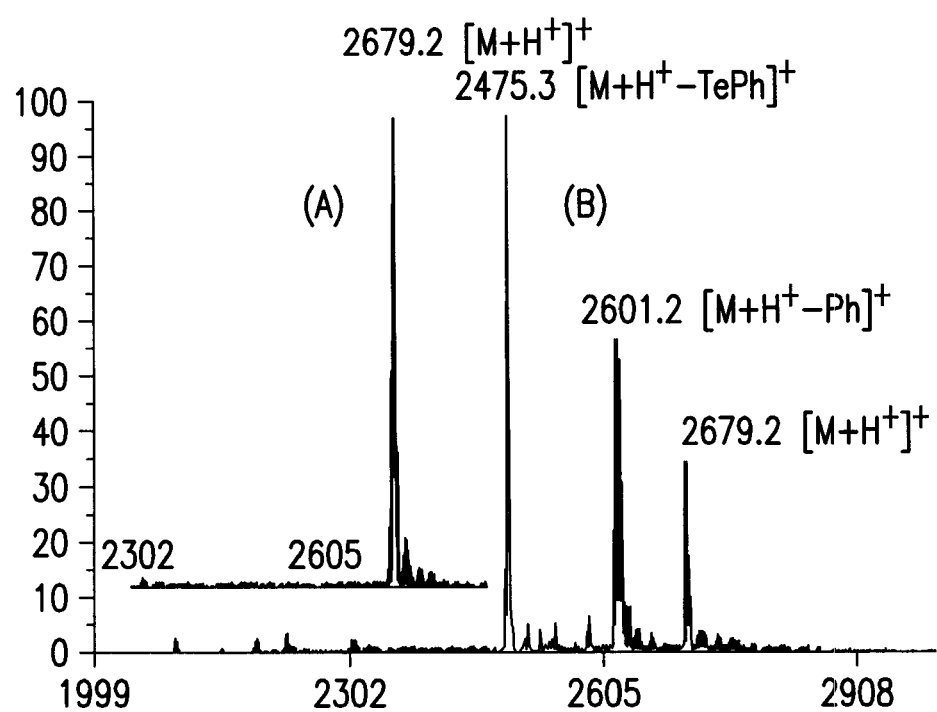
FIG. 53. MALDI-TOF mass spectra of the Te-DNA [5'-G(2'-SeMe-dU)G($^{Te}$T)ACAC-3'; molecular formula: $C_{83}H_{101}N_{30}O_{46}P_7SeTe$; F.W.: 2678.2]. (A) the crystal sample without X-ray irradiation; (B) the crystal sample with X-ray irradiation.
Figure 54:
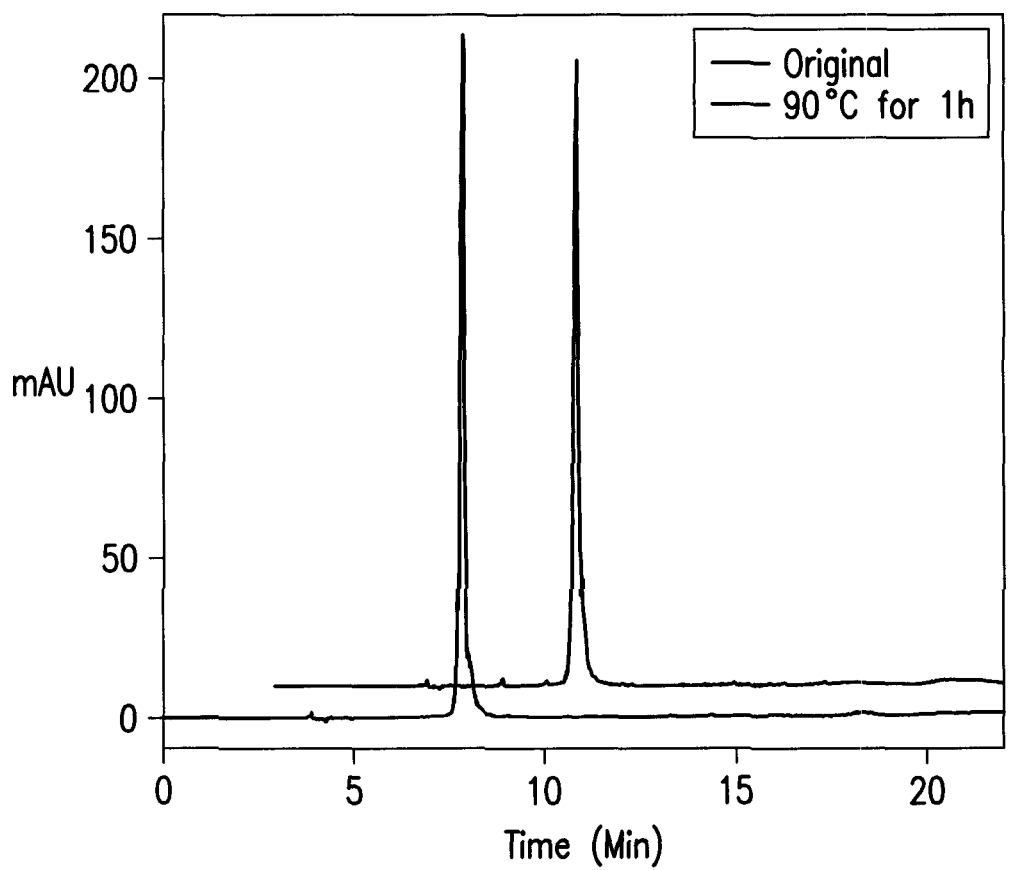
FIG. 54. The Te-DNA thermal stability and HPLC analysis. Buffer A: 20 mM TEAAc; Buffer B: 50% acetonitrile in buffer A. HPLC conditions: Welchrom C18-XB column (4.6× 250 mm, 5☐), 25° C., 1 mL/min, gradient from buffer A to 50% buffer B in 15 min. HPLC profiles of Te-DNA [5'-G(2'-SeMe-dU)G($^{Te}$T)ACAC-3'] thermal analysis: the black one (without heating), the red one (heated in 10 mM Na—PO$_4$ buffer, pH 7.3, at 90° C. for 1 hr).

Mass analysis of Te—C bond breaking caused by X-ray irradiation: In this test, a few fresh crystals were sent to MALDI-TOF mass collection before X-ray irradiation. And as comparison, about 20 crystals were picked to be exposed to X-ray for certain time before re-checking the mass spectrum. Fortunately, the Te-functionality is stable in the absence of X-ray irradiation. Stability of the Te-DNA crystals was investigated by MS analysis after the crystal formation. The MS analysis indicated no significant decomposition of the Te-DNA crystals in the crystallization droplet after 3 weeks (FIG. 53 (A)). Furthermore, the Te-DNA is stable under a higher temperature. As shown by FIG. 54, the Te-DNA was heated at 90° C. for 1 hr without significant decomposition.

Figure 52:
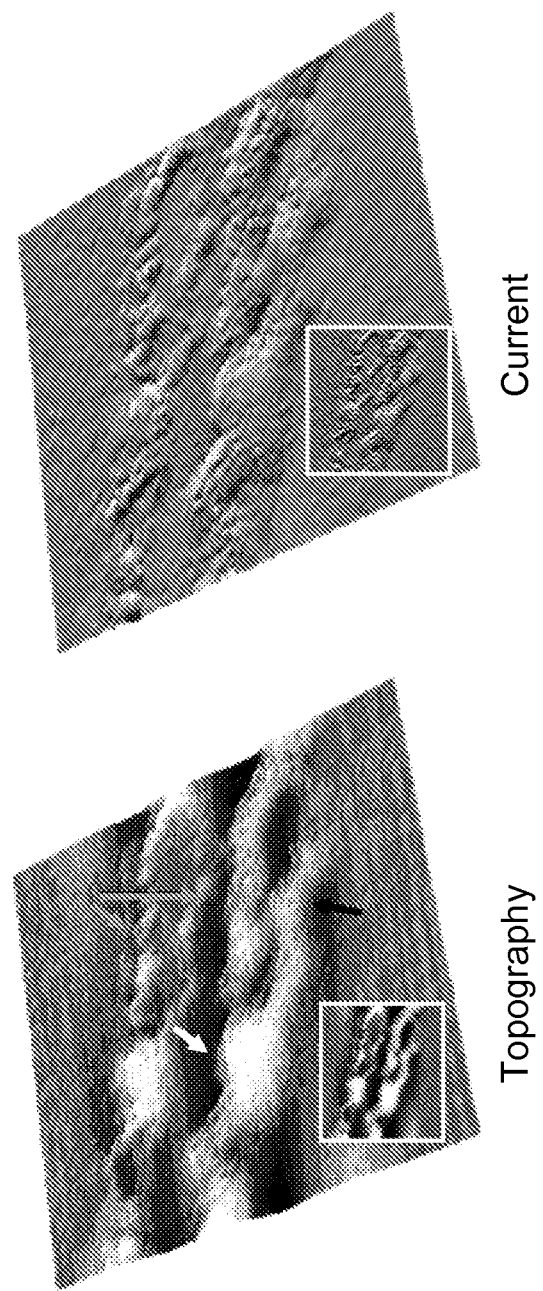
FIG. 52. The 3D topography and current images of native DNA duplex [5'-ATGGTGCTC-3' and 3'-(TACCACGAG)$_6$-5'] without modification on HOPG (35 nm×35 nm). Comparing to the Te-modified DNA duplex, this native sample doesn't show obvious conductivity. The insets are 2D images corresponding to the 3D images. The Sample bias: 0.50V, the current set point: 100pA.

STM Experiment: In this test, highly oriented pyrolytic graphite (HOPG) was used as support substrate to study DNA molecules [F. Rose, P. Martin, H. Fujita, H. Kawakatsu, *Nanotechnology* 2006, 17, 3325-3332]. The HOPG was freshly cleaved with scotch tapes prior to each experiment, and treated with UV Surface Decontamination System (Novascan Technologies Inc.) for 20 min before using to modify the surface of the hydrophobic HOPG to the hydrophilic surface. The bare HOPG surface did not show obvious structure changes even at the atomic level. Both of the native and Te-modified DNA samples (100 μL, 0.03 μM were in PBS solution. The sample solutions were loaded on the HOPG surface. After 20 min, the DNA samples were scanned with STM in the PBS buffer (FIG. 52). To reduce the influence of leakage current, the newly-cut Au STM tip was coated with Apiezon W Wax (SPI Supplies'Division of Structure Probe, Inc.) only to leave the top area of the tip exposed as it was reported by Lindsay [L. A. Naganara, T. Thundat, S. M. Lindsay, *Rev. Sci. Instrum.* 1989, 60, 3128-3130].

UV-thermal denaturation studies: To evaluate the potential structure perturbation caused by this bulky tellurium moiety (Ph-Te), a UV-thermal denaturation studies were conducted. The experimental results indicate that the Te-derivatized duplex structures are as stable as the corresponding natives (Table 8 and FIGS. 48-50). Unlike the corresponding 5-Ph-S substitution, which caused a significant destabilization[11] and decreased the DNA duplex melting-temperature (Tm) by 5° C. per modification, the 5-Ph-Te substitution doesn't significantly alter the duplex Tm. The significant Tm decrease and duplex stability disruption in the case of the 5-Ph-S may be attributed to the bulky and hydrophobic 5-Ph-S functionality, which causes significant perturbation. Comparing the Ph-Te and Ph-S functionalities and according to their effect on the duplex stability, the electron-richer tellurium and its electron delocalization compensate the destabilization effect caused by the bulky and hydrophobic functionality.

TABLE 8

UV-melting study of the Te-DNA duplexes

Figure 56:
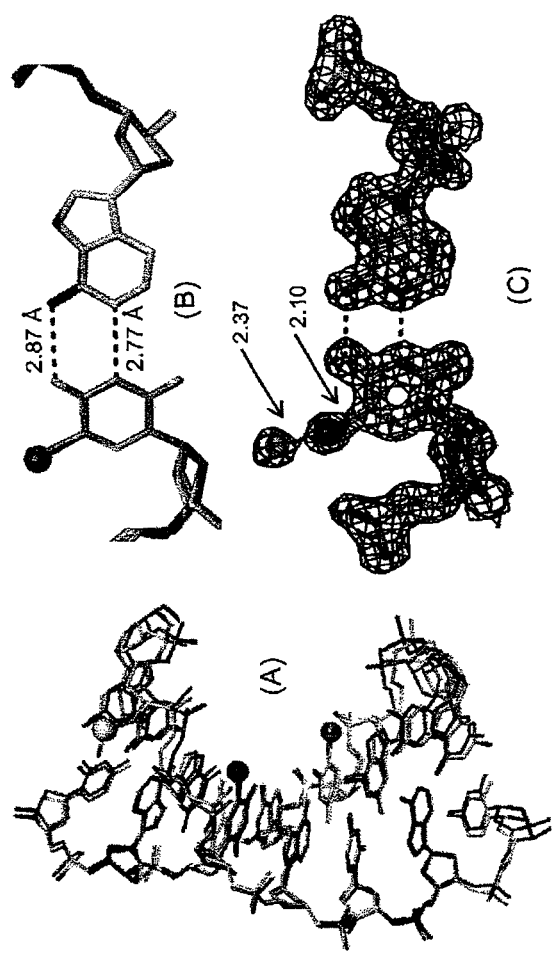
FIG. 56. The global and local structures of the Te-DNA duplex, [5'-G(2'-SeMe-dU)G($^{Te}$T)ACAC-3']$_2$. The red and yellow balls represent Te and Se atoms, respectively. (A) The Te-dsDNA structure (in cyan; 1.50 Å resolution; PDB ID: 3FA1) is superimposed over the native one (in magenta; PDB ID: 1DNS); (B) The local structure of the $^{Te}$T/A base pair (in cyan) is superimposed over the native T/A base pair (in magenta). (C) The experimental electron density of the $^{Te}$T/A base pair (σ=1.0). The green ball represents approximately ⅙ of phenyl group (1 carbon).

| Entry | DNA duplex | Tm (° C.) |
|---|---|---|
| 1 | 5'-ATGG($^{Te}$T)GCTC-3'<br>3'-TACCACGAG-5' | 40.3 ± 0.2 |
| 2 | 5'-ATGGTGCTC-3'<br>3'-TACCACGAG-5' | 39.8 ± 0.3 |
| 3 | 5'-CT($^{Te}$T)CTTGTCCG-3'<br>3'-GAAGAACAGGC-5' | 44.1 ± 0.3 |
| 4 | 5'-CTTCTTGTCCGC-3'<br>3'-GAAGAACAGGC-5' | 44.0 ± 0.2 | crystal structure of the Te-derivatized DNA [5'-G(2'-Se-dU)G($^{Te}$T)ACAC-3']$_2$: the crystal structure of the Te-derivatized DNA [5'-G(2'-Se-dU)G($^{Te}$T)ACAC-3']$_2$ was determined by taking advantage of the 2'-Se-moiety assisted crystallization [a) J. Jiang, J. Sheng, N. Carrasco, Z. Huang, Nucleic Acids Res. 2007, 35, 477-485. b) J. Salon, J. Sheng, J. Gan, Z. Huang, J. Org. Chem. 2010, 75, 637-641. c) J. Sheng, J. Salon, J. Gan,; Z. Huang, Sci. China Chem. 2010, 53, 78-85]. The Te-DNA structure (1.50 Å resolution) revealed that both global and local structures of this Te-DNA are virtually identical to the native one (FIGS. 56 A and B), indicating the Te-moiety does not cause significant perturbation. The structure result is also consistent with our biophysical study, suggesting that $^{Te}$T and A (FIGS. 56 B and C) pair as well as native T and A. Since the Te—C bond is sensitive to X-ray irradiation, the occupancy of tellurium (approximately 40%) in the crystal structure is expected. The low electron density of the phenyl group (approximately 16% of expected density) is consistent with cleavage of these two Te—C bonds [Te-05 and Te—C(Ph)] by the X-ray irradiation. To verify this, the mass analysis of the Te-DNA crystals was carried out by their exposure to X-ray irradiation. The MALDI-MS spectra (FIG. 53) have shown both Te—C bond cleavage before the X-ray irradiation and the loss of 78 (the phenyl group) and 203.9 mass units (the phenyltelluro group) after irradiation, indicating partial cleavage of Te—C bond by irradiation. Fortunately, the Te-functionality is stable in the absence of X-ray irradiation. Stability of the Te-DNA crystals was investigated by MS analysis after the crystal formation. The MS analysis indicated no significant decomposition of the Te-DNA crystals in the crystallization droplet after 3 weeks (FIG. 53A). Furthermore, the Te-DNA is stable under a higher temperature. As shown by FIG. 54, the Te-DNA was heated at 90° C. for 1 hr without significant decomposition.

The STM images of the Te-modified DNA duplex [5'-ATGG($^{Te}$T)-GCTC-3' and 5'-(GAGCACCAT)$_6$-3'] on highly oriented pyrolytic graphite (HOPG): Since tellurium atom has metallic property, it is expected that the Te-modified DNA has higher visibility and conductivity, under STM imaging, than the corresponding native DNA. To investigate this, the Te-DNA was synthesized [9 nt., 5'-ATGG($^{Te}$T)-GCTC-3' FIG. 55] that is complementary to a native DNA [54 nt., 5'-(GAGCACCAT)$_6$-3'] by six repeats, and conducted the STM studies. Interestingly, the experiments revealed that the Te-modified DNA duplexes showed much stronger topographic and current peaks (FIG. 55) than the corresponding native duplexes (FIG. 52). Moreover; the topographic and current images show that the Te-derivatization allows visualization of the 54-bp DNA duplex (calculated length: 18 mu) with approximately 20 nm in measured length. The topographic and current images (or peaks) of the corresponding native duplex are not strong (FIG. 52). The duplexes with the Te-modification assemble together side by side (FIG. 55A). The result also indicates that the current/conductivity imaging of the Te-modified duplex (FIG. 55 B) is sensitive to the duplex assembling while its corresponding topographic imaging (FIG. 55A) is not so sensitive. The Te-DNA duplex performs much better under the current/conductivity imaging than the corresponding native duplex.

REFERENCES

Watson, J. D. & Crick, F. H. (1953) Nature 171, 737-8.
Storz, G. (2002) Science 296, 1260-1263.
Becker, H. F., Motorin, Y., Florentz, C., Giege, R. & Grosjean, H. (1998) Nucleic Acids Res 26, 3991-7.
Sprinzl, M. & Vassilenko, K. S. (2005) Nucleic Acids Res 33, D139-40.
McCloskey, J. A. & Rozenski, J. (2005) Nucleic Acids Res 33, D135-8.
Wang, S. & Kool, E. T. (1995) Biochemistry 34, 4125-32.
Umezawa, Y. & Nishio, M. (2002) Nucleic Acids Res 30, 2183-92.
Chatterjee, S., Pathmasiri, W. & Chattopadhyaya, J. (2005) Org Biomol Chem 3, 3911-5.
Suzuki, M. M. & Bird, A. (2008) Nat Rev Genet 9, 465-76.
Ng, L. J., Cropley, J. E., Pickett, H. A., Reddel, R. R. & Suter, C. M. (2009) Nucleic Acids Res.
Petrovich, M. & Veprintsev, D. B. (2009) J Mol Biol 386, 72-80.
Marinas, M. G. & Casadesus, J. (2009) FEMS Microbiol Rev.
Low, D. A. & Casadesus, J. (2008) Curr Opin Microbiol 11, 106-12.
Gesteland, R. F. C., T. R.; Atkins, J. F., Eds. (2006) The RNA World: The Nature of Modern RNA Suggests a Prebiotic RNA, ed. 3, (Cold Spring Harbor Laboratory Press Cold Spring Harbor, NY,).
Wing, R., Drew, H., Takano, T., Broka, C., Tanaka, S., Itakura, K. & Dickerson, R. E. (1980) Nature 287, 755-8.
Chen, H. & Patel, D. J. (1995) J. Am. Chem. Soc. 117, 5901-5913.
Gyi, J. I., Lane, A. N., Conn, G. L. & Brown, T. (1998) Biochemistry 37, 73-80.
Egli, M., Minasov, G., Tereshko, V., Pallan, P. S., Teplova, M., Inamati, G. B., Lesnik, E. A., Owens, S. R., Ross, B. S., Prakash, T. P. & Manoharan, M. (2005) Biochemistry 44, 9045-57.
Chen, C. Y., Ko, T. P., Lin, T. W., Chou, C. C., Chen, C. J. & Wang, A. H. (2005) Nucleic Acids Res 33, 430-8.
Baird-Titus, J. M., Clark-Baldwin, K., Dave, V., Caperelli, C. A., Ma, J. & Rance, M. (2006) J Mol Biol 356, 1137-51.
Sheng, J., Jiang, J., Salon, J. & Huang, Z. (2007) Org Lett 9, 749-52.
Jiang, J., Sheng, J., Carrasco, N. & Huang, Z. (2007) Nucleic Acids Res 35, 477-85.
Salon, J., Sheng, J., Jiang, J., Chen, G., Caton-Williams, J. & Huang, Z. (2007) J Am Chem Soc 129, 4862-3.
Salon, J., Jiang, J., Sheng, J., Gerlits, O. O. & Huang, Z. (2008) Nucleic Acids Res 36, 7009-18.
Singh, S. K., Babu, M. M. & Balaram, P. (2003) Proteins 51, 167-71.
Uldry, A. C., Griffin, J. M.; Yates, J. R., Perez-Torralba, M., Maria, M. D., Webber, A. L., Beaumont, M. L., Samoson, A., Claramunt, R. M., Pickard, C. J. & Brown, S. P. (2008) J Am Chem Soc 130, 945-54.
Scheiner, S., Kar, T. & Gu, Y. (2001) J Biol Chem 276, 9832-7.

Anbarasu, A., Anand, S. & Sethumadhavan, R. (2007) *Biosystems* 90, 792-801.

Li, Y. & Flood, A. H. (2008) *Angew Chem Int Ed Engl* 47, 2649-52.

Sarkhel, S., Rich, A. & Egli, M. (2003) *J Am Chem Soc* 125, 8998-9.

Tewari, A. K. & Dubey, R. (2008) *Bioorg Med Chem* 16, 126-43.

Caton-Williams, I. & Huang, Z. (2008) *Angew Chem Int Ed Engl* 47, 1723-5.

Caton-Williams, J. & Huang, Z. (2008) *Chem Biodivers* 5, 396-407.

Sheng, J. & Huang, Z. (2008) International Journal of Molecular Sciences 9, 258-271.

Lee, C. H. & Kim, Y. H. (1991) *Tetrahedron Letters* 32, 2401-2404.

Ahmadian, M., Mang, P. M. & Bergstrom, D. E. (1998) *Nucleic Acids Research* 26, 3127-3135.

Carrasco, N., Ginsburg, D., Du, Q. & Huang, Z. (2001) *Nucleosides Nucleotides Nucleic Acids* 20, 1723-34.

Du, Q., Carrasco, N., Teplova, M., Wilds, C. J., Egli, M. & Huang, Z. (2002) *J Am Chem Soc* 124, 24-5.

Wilds, C. J., Pattanayek, R., Pan, C., Wawrzak, Z. & Egli, M. (2002) *J Am Chem Soc* 124, 14910-6.

Carrasco, N., Buzin, Y., Tyson, E., Halpert, E. & Huang, Z. (2004) *Nucleic Acids Res* 32, 1638-46.

Moroder, H., Kreutz, C., Lang, K., Serganov, A. & Micura, R. (2006) *J Am Chem Soc* 128; 9909-18.

Jain, S., Zon, G. & Sundaralingam, M. (1989) *Biochemistry* 28, 2360-4.

Su, X. D., Taddei, N., Stelimi, M., Ramponi, G. & Nordlund, P. (1994) *Nature* 370, 575-8.

Yudushkin, I. A., Schleifenbaum, A., Kinkhabwala, A., Neel, B. G., Schultz, C. & Bastiaens, P. I. (2007) *Science* 315, 115-9.

Z. Otwinowski, W. Minor, *Meth. Enzymol.* 1997, 276, 307-326.

A. J. McCoy, R. W. Grosse-Kunstleve, P. D. Adams, M. D. Winn, L. C. Storoni, R. J. Read, *J. Appl. Cryst.* 2007, 40; 658-674.

A. T. Brunger, P. D. Adams, G. M. Clore, W. L. DeLano, P. Gros, R. W. Grosse-Kunstleve, J. S. Jiang, J. Kuszewski, M. Nilges, N. S. Pannu, R. J. Read, L. M. Rice, T. Simonson, G. L. Warren, *Acta. Cryst. D. Biol. Cryst.* 1998, 54, 905-921.

G. N. Murshudov, A. A. Vagin, E. J. Dodson, *Acta. Cryst. D. Biol. Cryst.* 1997, 53, 240-255.

G. Parkinson; J Vojtechovsky, L. Clowney, A. T. Brunger, H. M. Berman, *Acta. Cryst. D. Biol. Crysta.* 1996, 52, 57-64.

A. T. Brunger, *Nature* 1992, 355, 472-475.

R. J. Read, *Acta. Cryst. A.* 1986, 42, 140-149.

F. Rose, P. Martin, H. Fujita, H. Kawakatsu, *Nanotechnology* 2006, 17, 3325-3332.

L. A. Naganara, T. Thundat, S. M. Lindsay, *Rev. Sci. Instrum.* 1989, 60, 3128-3130.

a) J. Zheng, J. J. Birktoft, Y. Chen, T. Wang, R. Sha, P. E. Constantinou, S. L. Ginell, C. Mao, N. C. Seeman, *Nature* 2009, 461, 74-77. b) E. S. Andersen, M. Doug, M. M. Nielsen, K. Jahn, R. Subramani, W. Mamdouh, M. M. Golas, B. Sander, H. Stark, C. L. Oliveira, J. S. Pedersen, V. Birkedal, F. Besenbacher, K. V. Gothelf J. Kjems, *Nature* 2009, 459, 73-76. c) P. W. Rothemund, *Nature* 2006, 440, 297-302. d) X. Xue, F. Wang, X. Liu, *J. Am. Chem. Soc.* 2008, 130, 3244-3245.

A. Singer, M. Wanunu, W. Morrison, H. Kuhn, M. Frank-Kamenetskii, A. Meller, *Nano. Lett.* 2010, 10, 738-742.

K. Tiemann, J. J. Rossi, *EMBO Mol. Med.* 2009, 1, 142-151.

a) Y. C. Huang, D. Sen, *J. Am. Chem. Soc.* 2010, 132, 2663-2671. b) I. Kratochvilova, K. Kral, M. Buncek, A. Viskova, S. Nespurek, A. Kochalska, T. Todorciuc, M. Weiter, B. Schneider, *Biophys. Chem.* 2008, 138, 3-10. c) T. Ito, S. E. Rokita, *Angew. Chem. Int. Ed.* 2004, 43, 1839-1842. d) R. N. Barnett, C. L. Cleveland, A. Joy, U. Landman, G. B. Schuster, *Science* 2001, 294, 567-571. e) D. Porath, A. Bezryadin, S. de Vries, C. Dekker, *Nature* 2000, 403, 635-638. f) H. W. Fink, C. Schonenberger, *Nature* 1999, 398, 407-410.

a) Z. Yang, F. Chen, S. G. Chamberlin, S. A. Benner, *Angew. Chem. Int. Ed.* 2010, 49, 177-180. b) M. Egli, P. S. Pallas, *Chem. Biodivers.* 2010, 7, 60-89. c) A. E. Hassan, J. Sheng, W. Zhang, Z. Huang, *J. Am. Chem. Soc.* 2010, 132, 2120-2121. d) J. C. Delaney, J. Gao, H. Liu, N. Shrivastav, J. M. Essigmann, E. T. Kool, *Angew. Chem. Int. Ed. Engl.* 2009, 48, 4524-4527. e) M. Ljungman, *Chem. Rev.* 2009, 109, 2929-2950. f) A. M. Sismour, S. A. Benner, *Nucleic Acids Res.* 2005, 33, 5640-5646. g) T. W. Kim, J. C. Delaney, J. M. Essigmann, E. T. Kool, *Proc. Natl. Acad. Sci. USA* 2005, 102, 15803-15808.

a) E. Braun, Y. Eichen, U. Sivan, G. Ben-Yoseph, *Nature* 1998, 391, 775-778. b) J. L. Coffer, S. R. Bigham, X. Li, R. F. Pinizzotto, Y. G. Rho, R. M. Pirtle, I. L. Pirtle, *Appl. Phys. Lett.* 1996, 69, 3851-3853. c) Y. F. Ma, J. M. Zhang, G. J. Zhang, H. X. He, *J. Am. Chem. Soc.* 2004, 126, 7097-7101. d) X. Guo, A. A. Gorodetsky, J. Hone, J. K. Barton, C. Nuckolls, *Nat. Nanotechnol.* 2008, 3, 163-167. e) B. Elias, F. Shao, J. K. Barton, *J. Am. Chem. Soc.* 2008, 130, 1152-1153.

L. Moroder, *J. Pept. Sci.* 2005, 11, 187-214.

J. Sheng, Z. Huang, *Int. J. Mol. Sci.* 2008, 9, 258-271.

J. Sheng, A. E. Hassan, Z. Huang, *J. Org. Chem.* 2008, 73, 3725-3729.

J. Sheng, A. E. Hassan, Z. Huang, *Chem-Eur. J.* 2009, 15, 10210-10216.

M. Ahmadian, P. Zhang, D. E. Bergstrom, *Nucleic Acids Res.* 1998, 26, 3127-3135.

a) J. Jiang, J. Sheng, N. Carrasco, Z. Huang, *Nucleic Acids Res.* 2007, 35, 477-485. b) J. Salon, J. Sheng, J. Gan, Z. Huang, *J. Org. Chem.* 2010, 75, 637-641. c) J. Sheng, J. Salon, J. Gan, Z. Huang, *Sci. China Chem.* 2010, 53, 78-85.

What is claimed is:

1. A compound of formula (I), or a tautomer thereof, or a pharmaceutically acceptable salt of said compound or said tautomer;

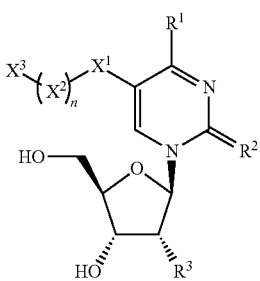

(I)

wherein:

$R^1$ is selected from the group consisting of hydroxyl, thiol, alkylthiol, arylthiol, selenol, alkylseleno, arylseleno, tellurol, alkyltelluro, aryltelluro, amino, alkylamino, arylamino and acylamino;

$R^2$ is selected from the group consisting of oxygen, sulfur, selenium, tellurium, amino, alkylamino, arylamino and acylamino;

$R^3$ is a hydrogen or a hydroxyl group;

$X^1$ is tellurium;

$X^2$ is linear or branched alkyl, or aryl;

$X^3$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino; and n is a subscript selected from 0 to 20.

2. The compound according to claim 1, wherein:

$R^1$ is selenol, alkylseleno, arylseleno, tellurol, alkyltelluro, or aryltelluro;

$R^2$ is selected from the group consisting of oxygen, sulfur, selenium, tellurium, amino, alkylamino, arylamino and acylamino;

$R^3$ is a hydrogen, or hydroxyl group;

$X^1$ is tellurium;

$X^2$ is linear or branched alkyl, or aryl;

$X^3$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino; and n is a subscript selected from 0 to 20.

3. The compound according to claim 1, wherein:
$R^1$ is selected from the group consisting of hydroxyl, thiol, alkylthiol, arylthiol, selenol, alkylseleno, arylseleno, tellurol, alkyltelluro, aryltelluro, amino, alkylamino, arylamino and acylamino;
$R^2$ is selenium or tellurium;
$R^3$ is a hydrogen, or hydroxyl group;
$X^1$ is tellurium;
$X^2$ is linear or branched alkyl, or aryl;
$X^3$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino; and
n is a subscript selected from 0 to 20.

4. The compound according to claim 1, wherein said tautomer is a compound of formula (II):

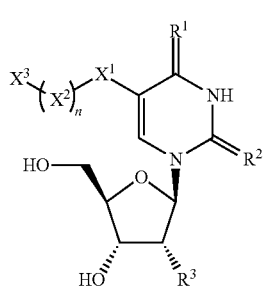

(II)

wherein:
$R^1$ is selected from the group consisting of is oxygen, sulfur, selenium, tellurium, amino, alkylamino, arylamino and acylamino;
$R^2$ is selected from the group consisting of oxygen, sulfur, selenium, tellurium, amino, alkylamino, arylamino and acylamino;
$R^3$ is a hydrogen or a hydroxyl group;
$X^1$ is tellurium;
$X^2$ is linear or branched alkyl, or aryl;
$X^3$ is selected from the group consisting of hydrogen, halogen, alkyl, aryl, hydroxyl, thiol, amino, alkyloxyl, aryloxyl, acyloxyl, alkylthiol, arylthiol, alkylseleno, arylseleno, alkyltelluro, aryltelluro, alkylamino, arylamino and acylamino; and n is a subscript selected from 0 to 20.

5. A compound with the following formula:

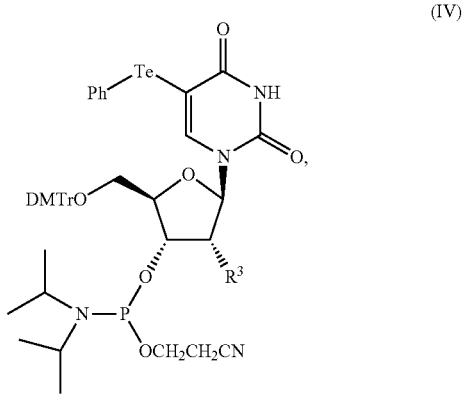

(IV)

wherein DMTr represents dimethoxytrityl and $R^3$ is H or O-TBDMS, wherein O-TBDMS represent Oxy-tert-butyldimethylsilane.

* * * * *

SEQUENCE LISTING

```
<160> NUMBER OF SEQ ID NOS: 5

<210> SEQ ID NO 1
<211> LENGTH: 11
<212> TYPE: DNA
<213> ORGANISM: Unknown
<220> FEATURE:
<223> OTHER INFORMATION: mammal

<400> SEQUENCE: 1
```

```
cttcttgtcc g                                                    11

<210> SEQ ID NO 2
<211> LENGTH: 10
<212> TYPE: DNA
<213> ORGANISM: Unknown
<220> FEATURE:
<223> OTHER INFORMATION: mammal

<400> SEQUENCE: 2
gcgtatacgc                                                      10

<210> SEQ ID NO 3
<211> LENGTH: 11
<212> TYPE: DNA
<213> ORGANISM: Unknown
<220> FEATURE:
<223> OTHER INFORMATION: mammal

<400> SEQUENCE: 3
gaagaacagg c                                                    11

<210> SEQ ID NO 4
<211> LENGTH: 24
<212> TYPE: DNA
<213> ORGANISM: Unknown
<220> FEATURE:
<223> OTHER INFORMATION: mammal

<400> SEQUENCE: 4
gtgcactgat caattaatgt cgac                                      24

<210> SEQ ID NO 5
<211> LENGTH: 24
<212> TYPE: DNA
<213> ORGANISM: Unknown
<220> FEATURE:
<223> OTHER INFORMATION: mammal

<400> SEQUENCE: 5
gtcgacatta attgatcagt gcac                                      24
```